US008008003B2

(12) United States Patent
Baker et al.

(10) Patent No.: US 8,008,003 B2
(45) Date of Patent: Aug. 30, 2011

(54) GENE EXPRESSION PROFILING OF EGFR POSITIVE CANCER

(75) Inventors: Joffre B. Baker, Montara, CA (US);
Maureen T. Cronin, Los Altos, CA (US); Steve Shak, Hillsborough, CA (US); Jose Baselga, Barcelona (ES)

(73) Assignee: Genomic Health, Inc., Redwood City, CA (US)

( * ) Notice: Subject to any disclaimer, the term of this patent is extended or adjusted under 35 U.S.C. 154(b) by 0 days.

(21) Appl. No.: 10/714,195

(22) Filed: Nov. 14, 2003

(65) Prior Publication Data

US 2005/0019785 A1 Jan. 27, 2005

Related U.S. Application Data

(60) Provisional application No. 60/427,090, filed on Nov. 15, 2002.

(51) Int. Cl.
*C12Q 1/68* (2006.01)
*C07H 21/02* (2006.01)
*C07H 21/04* (2006.01)
*C12M 1/34* (2006.01)

(52) U.S. Cl. ...... 435/6; 536/23.1; 536/24.31; 435/287.2

(58) Field of Classification Search .................. None
See application file for complete search history.

(56) References Cited

U.S. PATENT DOCUMENTS

| 4,699,877 | A | 10/1987 | Cline et al. ................. 435/6 |
|---|---|---|---|
| 4,968,603 | A | 11/1990 | Slamon et al. .............. 435/6 |
| 5,015,568 | A | 5/1991 | Tsujimoto et al. ........... 435/5 |
| 5,202,429 | A | 4/1993 | Tsujimoto et al. ......... 536/23.5 |
| 5,459,251 | A | 10/1995 | Tsujimoto et al. ......... 536/23.5 |
| 5,474,796 | A | 12/1995 | Brennan ................ 427/2.13 |
| RE35,491 | E | 4/1997 | Cline et al. ................. 435/6 |
| 5,670,325 | A | 9/1997 | Lapidus et al. .............. 435/6 |
| 5,741,650 | A | 4/1998 | Lapidus et al. .............. 435/6 |
| 5,830,665 | A | 11/1998 | Shuber et al. ............... 435/6 |
| 5,830,753 | A | 11/1998 | Coulie et al. ............. 435/325 |
| 5,858,678 | A | 1/1999 | Chinnadurai ............... 435/7.1 |
| 5,861,278 | A | 1/1999 | Wong et al. .............. 435/69.1 |
| 5,928,870 | A | 7/1999 | Lapidus et al. .............. 435/6 |
| 5,952,178 | A | 9/1999 | Lapidus et al. .............. 435/6 |
| 5,952,179 | A | 9/1999 | Chinnadurai ............... 435/6 |
| 5,962,312 | A | 10/1999 | Plowman et al. ......... 435/320.1 |
| 5,985,553 | A | 11/1999 | King et al. ................. 435/6 |
| 6,020,137 | A | 2/2000 | Lapidus et al. .............. 435/6 |
| 6,100,029 | A | 8/2000 | Lapidus et al. .............. 435/6 |
| 6,143,529 | A | 11/2000 | Lapidus et al. ........... 435/91.2 |
| 6,146,828 | A | 11/2000 | Lapidus et al. .............. 435/6 |
| 6,171,798 | B1 | 1/2001 | Levine et al. ............... 435/6 |
| 6,203,993 | B1 | 3/2001 | Shuber et al. ............... 435/6 |
| 6,207,401 | B1 | 3/2001 | Plowman et al. ............ 435/15 |
| 6,207,452 | B1 | 3/2001 | Govindaswamy ......... 435/330 |
| 6,214,558 | B1 | 4/2001 | Shuber et al. ............... 435/6 |
| 6,245,523 | B1 | 6/2001 | Altieri ................... 435/69.1 |
| 6,248,535 | B1 | 6/2001 | Danenberg et al. .......... 435/6 |
| 6,251,601 | B1 * | 6/2001 | Bao et al. .................. 435/6 |
| 6,271,002 | B1 | 8/2001 | Linsley et al. ............. 435/91.1 |
| 6,322,986 | B1 | 11/2001 | Ross ........................ 435/6 |
| 6,414,134 | B1 | 7/2002 | Reed ..................... 536/24.5 |
| 6,582,919 | B2 | 6/2003 | Danenberg ................. 435/6 |
| 6,602,670 | B2 | 8/2003 | Danenberg ................. 435/6 |
| 6,618,679 | B2 | 9/2003 | Loehrlein et al. ........... 702/20 |
| 6,620,606 | B2 | 9/2003 | Bandman et al. .......... 435/219 |
| 6,696,558 | B2 | 2/2004 | Reed et al. .............. 536/23.5 |
| 6,716,575 | B2 | 4/2004 | Plowman et al. ............ 435/6 |
| 6,750,013 | B2 | 6/2004 | Gish et al. .................. 435/6 |
| 6,800,737 | B2 | 10/2004 | Altieri .................... 530/386 |
| 6,943,150 | B1 | 9/2005 | Altieri .................... 514/21 |
| 2002/0004491 | A1 | 1/2002 | Xu et al. .................. 514/44 |
| 2002/0009736 | A1 | 1/2002 | Wang ....................... 435/6 |
| 2002/0039764 | A1 | 4/2002 | Rosen .................... 435/69.1 |
| 2002/0160395 | A1 | 10/2002 | Altieri et al. ............... 435/6 |
| 2002/0194022 | A1 * | 12/2002 | Comite .................... 705/2 |
| 2003/0073112 | A1 | 4/2003 | Zhang et al. ............... 435/6 |
| 2003/0104499 | A1 | 6/2003 | Pressman et al. ......... 435/7.23 |
| 2003/0165952 | A1 | 9/2003 | Linnarsson et al. .......... 435/6 |
| 2003/0180791 | A1 | 9/2003 | Chinnadurai ............... 435/6 |
| 2003/0198970 | A1 | 10/2003 | Roberts .................... 435/6 |
| 2003/0198972 | A1 | 10/2003 | Erlander et al. ............. 435/6 |
| 2003/0219771 | A1 | 11/2003 | Bevilacqua et al. .......... 435/6 |
| 2003/0229455 | A1 | 12/2003 | Bevilacqua et al. ......... 702/20 |
| 2004/0009489 | A1 | 1/2004 | Golub et al. ............... 435/6 |
| 2004/0126775 | A1 | 7/2004 | Altieri et al. ............... 435/6 |

(Continued)

FOREIGN PATENT DOCUMENTS

EP 0 108 564 B1 5/1988

(Continued)

OTHER PUBLICATIONS

Giaccone et al. EGFR inhibitors: what have we learned from the treatment of lung cancer. Nov. 2005 Nature vol. 2, No. 11 pp. 554-561.*
Filmus, Jorge. Glypicans in growth control and cancer. 2001. Glycobiology. vol. 11, No. 3, pp. 19R-23R.*
Hlubek, Falk et al. Expression of the Invasion Factor LAminin gamma2 in colorectal carcinomas is regulated by beta catenin. Nov. 2001. Cancer Research vol. 61, pp. 8089-8093.*
Wu, Thomas. Analysing gene expression data from DNA microarrys to identify candidate genes. 2001. Journal of Pathology. vol. 195 pp. 53-65.*
Lucentini, Jack. Gene Association Studies Typically Wrong. 2004. The Scientist. vol. 18 pp. 1-4.*

(Continued)

*Primary Examiner* — Amanda Shaw
(74) *Attorney, Agent, or Firm* — Paula A. Borden; Bozicevic Field & Francis LLP.

(57) ABSTRACT

The present invention concerns prognostic markers associated with EGFR positive cancer. In particular, the invention concerns prognostic methods based on the molecular characterization of gene expression in paraffin-embedded, fixed tissue samples of EGFR-expressing cancer, which allow a physician to predict whether a patient is likely to respond well to treatment with an EGFR inhibitor.

15 Claims, 2 Drawing Sheets

U.S. PATENT DOCUMENTS

| | | | |
|---|---|---|---|
| 2004/0133352 A1 | 7/2004 | Bevilacqua et al. | ............ 702/19 |
| 2009/0298701 A1 | 12/2009 | Baker et al. | |

FOREIGN PATENT DOCUMENTS

| | | |
|---|---|---|
| EP | 1 365 034 | 11/2003 |
| WO | WO 99/02714 | 1/1999 |
| WO | WO 00/50595 | 8/2000 |
| WO | WO 00/55173 | 9/2000 |
| WO | WO012227 | 2/2001 |
| WO | WO 01/25250 | 4/2001 |
| WO | WO 01/40466 | 6/2001 |
| WO | WO 01/55320 | 8/2001 |
| WO | WO 01/70979 | 9/2001 |
| WO | WO 02/00677 | 1/2002 |
| WO | WO 02/06526 | 1/2002 |
| WO | WO 02/08260 | 1/2002 |
| WO | WO 02/08261 | 1/2002 |
| WO | WO 02/08282 | 1/2002 |
| WO | WO 02/08765 | 1/2002 |
| WO | WO 02/44413 A2 | 6/2002 |
| WO | WO 02/46467 | 6/2002 |
| WO | WO0244413 A2 | 6/2002 |
| WO | WO 02/017852 | 7/2002 |
| WO | WO 02/055988 | 7/2002 |
| WO | WO 02/059377 | 8/2002 |
| WO | WO 02/068579 | 9/2002 |
| WO | WO 02/068579 A2 | 9/2002 |
| WO | WO 02/103320 | 12/2002 |
| WO | WO 03/011897 | 2/2003 |
| WO | WO 03/078662 | 9/2003 |
| WO | WO 03/083096 | 10/2003 |
| WO | WO 2004/000094 A2 | 12/2003 |

OTHER PUBLICATIONS

Evans, William et al. Moving towards individualized medicine with pharmacogenomics. 2004. Nature vol. 429, pp. 464-468.*

Newton, MA et al. On differentail variablility of expression ratios: improving statistical inference about gene expression changes from microarray data. Journal of Computational Biology 2001. vol. 8, No. 1 pp. 37-52.*

Cheung, Vivian et al. Natural variation in human gene expression assessed in lymphoblastoid cells. 2003 Nature Genetics vol. 33 pp. 422-425.*

Lee, Wooin et al. Cancer pharmacogenomics: powerful tools in cancer chemotherapy and drug development. The Oncologist 2005. vol. 10 pp. 104-111.*

Riese, David et al. Specificity within the EFG family/ErbB receptor family signaling network: BioEssays 1998. vol. 20 pp. 41-48.*

Chun, So Young. The significance of CD44 variants expression in colorectal cancer and its regional lymph nodes. 2000. Journal of Korean Medical Science. vol. 15 pp. 696-700.*

Salomon, Davide et al. Epidermal growth factor related peptides and their receptors in human malignancies. 1995 Critical Reviews in Oncology/Hematology vol. 19 pp. 183-232.*

Notterman, Daniel et al. Transcriptional Gene Expression Profiles of Colorectal Adenoma, Adenocarcinoma, and Normal Tissue Examined by Oligonucleotide Arrays. 2001. Cancer Research vol. 61 pp. 3124-3130.*

Lehmann, Ulrich et al. Real Time PCR Analysis of DNA and RNA Extracted from Formalin Fixed and Paraffin Embedded Biopsies. 2001 Methods. vol. 25 pp. 409-418.*

Affymetrix array finder at www.affymetrix.com accessed online Jul. 16, 2008.*

Airenne, Tomi et al. Differential expression of mouse laminin gamma2 and gamma2* chain transcripts. 2000. Cell Tissue Research. vol. 300 pp. 129-137.*

Solmi, Rossella et al. Displayed correlation between gene expression profiled and submicroscopic alterations in response to cetuximab, gefitinib and EGF in human colon cancer cell lines. 2008 BMC Cancer vol. 8 p. 227.*

Thisted, Ronald. What is a p value?. 1998 The University of Chicago. http://www.stat.uchicago.edu/~thisted.*

Bhattacharjae, Arindam, et al., Proc. Natl. Acad. Sci. USA, vol. 98, No. 24, 2001, pp. 13790-13795.

Golub, T.R., et al., Science, vol. 286, 1999, pp. 531-537.

Martin, Katherine J., et al., Cancer Research. 60, 2000, pp. 2232-2238.

Ramaswamy, Sridhar, et. al., Proc. Natl. Acad. Sci. USA, 2001, vol. 98, pp. 15149-15154.

Rimm, D.L., et al., Molecular Cloning Reveals Alternative Splice Forms of Human a(E) Catenin, Biochemical and Biophysical Research Communications, 1994, vol. 203, pp. 1691-1699.

Sorlie, Therese, et al., Proc. Natl. Acad. Sci. USA, 2001, vol. 98, No. 19, pp. 10869-10874.

West, Mike, et al., Proc. Natl. Acad. Sci. USA, 2001, vol. 98, No. 20, pp. 11462-11467.

Yan, Pearlly S., et al., Cancer Research, 2001, vol. 61, pp. 8375-8380.

Yeung, Chen-Hsiang, et al., Bioinformatics, vol. 17, Suppl. 1, 2001, pp. S316-S322.

Zhao, Renbin, et al., Analysis of p53-Regulated Gene Expression Patterns Using Oligonucleotide Arrays, Genes & Development, 2000, vol. 14, pp. 981-993.

Arteaga, C.L, Journal of Clinical Oncology, vol. 19:(18), Suppl. (2001).

Bishop, P.C. et al., Oncogene, 21: 119-127 (2002).

Busse, D. et al., The Journal of Biological Chemistry, 275:(10) 6987-6995 (2000).

Specht, K. et al., American Journal of Phathology, 158:2 (2001).

Brabender, Jan, et al.; *Epidermal Growth Factor Receptor and HER2-neu mRNA Expression in Non-Small Cell Lung Cancer Is Correlated with Survival*, Clinical Cancer Research; vol. 7, Jul. 2001; pp. 1850-1855.

Ding, Chunming, et al.; *A high-throughput gene expression analysis technique using competitive PCR and matrix-assisted laser desorption ionization time-of-flight MS*, PNAS, vol. 100:6; Mar. 18, 2003; pp. 3059-3064.

Cambridge Healthtech Institute Conference Agenda; "Enabling Molecular Profiling With Cellular Resolution: Microgenomics Using Homogeneous Cell Samples"; Dec. 2002; 5 pgs.

Yang, Li, et al.; *BADGE, BeadsArray for the Detection of Gene Expression, a High-Throughput Diagnostic Bioassay*; Genome Research; vol. 11; 2001; pp. 1888-1898.

Zembutsu, et al. Gene-expression profile analysis of human tumor xemografts in nude mice during oral administration of the EGFR tyrosine kinase inhibitor. Proceedings of the Japanese Cancer Association, vol. 61, p. 166, 1057 (Aug. 2002).

He, et al. Inhibitory effects of EGFR antisense oligodeox ynucleotide in human colorectal cancer cell line. World J Gastroenterol. Oct. 2000;6(5):747-749.

Roberts, et al. Importance of epidermal growth factor receptor signaling in establishment of adenomas and maintenance of carcinomas during intestinal tumorigenesis. Proc Natl Acad Sci U S A. Feb. 5, 2002;99(3):1521-6.

Williams, et al. ZD1839 ('Iressa'), a specific oral epidermal growth factor receptor-tyrosine kinase inhibitor, potentiates radiotherapy in a human colorectal cancer xenograft model. Br J Cancer. Apr. 8, 2002;86(7):1157-61.

Lonardo et al. Evidence for the epidermal growth factor receptor as a target for lung cancer prevention. Clin Cancer Res. Jan. 2002;8(1):54-60.

Bunshi Kokyu Kibyo, vol. 6, pp. 359-367 (Sep. 2002).

Airenne et al. Structure of the human laminin y2 chain gene (LAMC2): alternative splicing with different tissue distribution of two transcripts. 1996, Genomics 32:54.

Albanell et al. Activated extracellular signal-regulated kinases: association with epidermal growth factor receptor/ transforming growth factor alpha expression in head and neck squamous carcinoma and inhibition by anti-epidermal growth factor receptor treatments. 2001, Cancer Research 61:6500-6510.

Baselga. Why the epidermal growth factor receptor? the rationale for cancer therapy. 2002, The Oncologist, suppl 4, pp. 2-8.

Ciardiello and Tortora, "A Novel Approach in the Treatment of Cancer: Targeting the Epidermal Growth Factor Receptor," 2001, Clin. Cancer Res. 7:2958-2970.

Tewes et al., "Results of a Phase I Trial of the Humanized Anti Epidermal Growth Factor Receptor (EGFR) Monoclonal Antibody EMD 72000 in Patients With EGFR Expressing Solid Tumors," Proc. Am. Soc. Clin. Oncol. Abstract 378 (2002).

Arteaga. The epidermal growth factor receptor: from mutant oncogene in nonhuman cancers to therapeutic target in human neoplasia. J Clin Oncol. Sep. 15, 2001;19(18 Suppl):32S-40S.

Bishop, et al. Differential sensitivity of cancer cells to inhibitors of the epidermal growth factor receptor family. Oncogene. Jan. 3, 2002;21(1):119-127.

Bunshi Kokyuki Byo. 2002, Respiratory Molecular Medicine, vol. 6, No. 5, pp. 359-367. (Japanese Reference).

Busse, et al. Reversible G(1) arrest induced by inhibition of the epidermal growth factor receptor tyrosine kinase requires up-regulation of p27(KIP1) independent of MAPK activity. J Biol Chem. Mar. 10, 2000;275(10):6987-6995.

Lonardo, et al. Evidence for the epidermal growth factor receptor as a target for lung cancer prevention. Clin Cancer Res. Jan. 2002;8(1):54-60.

Ball et al., "Neuron-Specific Hel-N1 and HuD as Novel Molecular Markers of Neuroblastoma: A Correlation of HuD Messenger RNA Levels with Favorable Prognostic Features," Clin. Cancer Res. 3:1859-1865 (1997).

Maitra et al., "The RNA Component of Telomerase as a Marker of Biologic Potential and Clinical Outcome in Childhood Neurobastic Tumors," Cancer 85:741-749 (1999).

Chen, et al. Discordant protein and mRNA expression in lung adenocarcinomas. 2001, Mol. Cell Proteomics, vol. 1, pp. 304-313.

Khambata-Ford et al., "Expression of Epiregulin and Amphiregulin and K-ras Mutation Status Predict Disease Control in Metastatic Colorectal Cancer Patients Treated With Cetuximab" Journal of Clinical Oncology, 25 (22):3230-3237 (Aug. 1, 2007).

Lenz et al., "Multicenter Phase II and Translational Study of Cetuximab in Metastatic Colorectal Carcinoma Refractory to Irinotecan, Oxaliplatin, and Fluoropyrimidines" Journal of Clinical Oncology, 24(30):4914-4921 (Oct. 20, 2006).

Saltz et al., "Phase II Trial of Cetuximab in Patients With Refractory Colorectal Cancer That Expresses the Epidermal Growth Factor Receptor" Journal of Clinical Oncology, 22(7):1201-1208 (Apr. 1, 2004).

K. Oda et al. A comprehensive pathway map of epidermal growth factor receptor signaling. Mol Syst Biol. 2005;1:2005.0011.

S. Moulder et al. Epidermal growth factor receptor (HER1) tyrosine kinase inhibitor ZD1839 (Iressa) inhibits HER2/neu (erbB2)-overexpressing breast cancer cells in vitro and in vivo.Cancer Res. Dec. 15, 2001;61(24):8887-8895.

* cited by examiner

SEQUENCE LISTING

<160> NUMBER OF SEQ ID NOS: 372

<210> SEQ ID NO 1
<211> LENGTH: 78
<212> TYPE: DNA
<213> ORGANISM: Homo sapiens

<400> SEQUENCE: 1
cgttccgatc tctatactg catcccaggc atgcctacag caccctgatg tcgcagccta    60

```
taaggccaac agggacct                                                  78

<210> SEQ ID NO 2
<211> LENGTH: 71
<212> TYPE: DNA
<213> ORGANISM: Homo sapiens

<400> SEQUENCE: 2
cgcttctatg gcgctgagat tgtgtcagcc ctggactacc tgcactcgga gaagaacgtg   60
gtgtaccggg a                                                         71

<210> SEQ ID NO 3
<211> LENGTH: 71
<212> TYPE: DNA
<213> ORGANISM: Homo sapiens

<400> SEQUENCE: 3
tcctgccacc cttcaaacct caggtcacgt ccgaggtcga cacaaggtac ttcgatgatg   60
aatttaccgc c                                                         71

<210> SEQ ID NO 4
<211> LENGTH: 69
<212> TYPE: DNA
<213> ORGANISM: Homo sapiens

<400> SEQUENCE: 4
ggacagcagg aatgtgtttc tccatacagg tcacggggag ccaatggttc agaaacaaat   60
cgagtgggt                                                            69

<210> SEQ ID NO 5
<211> LENGTH: 80
<212> TYPE: DNA
<213> ORGANISM: Homo sapiens

<400> SEQUENCE: 5
ggctcttgtg cgtactgtcc ttcgggctgg tgacagggaa gacatcactg agcctgccat   60
ctgtgctctt cgtcatctga                                                80

<210> SEQ ID NO 6
<211> LENGTH: 66
<212> TYPE: DNA
<213> ORGANISM: Homo sapiens

<400> SEQUENCE: 6
ccattcccac cattctacct gaggccagga cgtctggggt gtggggattg gtgggtctat   60
gttccc                                                               66

<210> SEQ ID NO 7
<211> LENGTH: 70
<212> TYPE: DNA
<213> ORGANISM: Homo sapiens

<400> SEQUENCE: 7
ccgccgtgga cacagactcc ccccgagagg tcttttttccg agtggcagct gacatgtttt   60
ctgacggcaa                                                           70

<210> SEQ ID NO 8
<211> LENGTH: 70
<212> TYPE: DNA
<213> ORGANISM: Homo sapiens
```

<400> SEQUENCE: 8
cttttgtgga actctatggg aacaatgcag cagccgagag ccgaaagggc caggaacgct     60
tcaaccgctg                                                            70

<210> SEQ ID NO 9
<211> LENGTH: 82
<212> TYPE: DNA
<213> ORGANISM: Homo sapiens

<400> SEQUENCE: 9
ccttccgacc agcagatgaa gatcatcgaa atcaatttgg gcaacgagac cgatcctcat     60
cagctcccaa tgtgcatata aa                                              82

<210> SEQ ID NO 10
<211> LENGTH: 79
<212> TYPE: DNA
<213> ORGANISM: Homo sapiens

<400> SEQUENCE: 10
gtgcaggaaa ggttcacaaa tgtggagtgt ctgcgtccaa tacacgcgtg tgctcctctc     60
cttactccat cgtgtgtgc                                                  79

<210> SEQ ID NO 11
<211> LENGTH: 81
<212> TYPE: DNA
<213> ORGANISM: Homo sapiens

<400> SEQUENCE: 11
agggagatgc cgcttcgtgg tggccgagca gacgccctcc tgtgtctgtg atgaaggcta     60
cattggagca aggtgtgaga g                                               81

<210> SEQ ID NO 12
<211> LENGTH: 72
<212> TYPE: DNA
<213> ORGANISM: Homo sapiens

<400> SEQUENCE: 12
atcctagccc tggttttggg cctccttttt gctgtcacca gcgtcgcgtt ccttgtgcag     60
atgagaaggc ag                                                         72

<210> SEQ ID NO 13
<211> LENGTH: 77
<212> TYPE: DNA
<213> ORGANISM: Homo sapiens

<400> SEQUENCE: 13
gaaggccaag aaccgagtca aattatattc cagtttaagg ccaatcctcc tgctgtgact     60
tttgaactaa ctgggga                                                    77

<210> SEQ ID NO 14
<211> LENGTH: 79
<212> TYPE: DNA
<213> ORGANISM: Homo sapiens

<400> SEQUENCE: 14
ccatacctca agtatttgcc atcagttatt gctggagctg cctttcattt agcactctac     60
acagtcacgg gacaaagct                                                  79

```
<210> SEQ ID NO 15
<211> LENGTH: 76
<212> TYPE: DNA
<213> ORGANISM: Homo sapiens

<400> SEQUENCE: 15
cctctgtgct acagattata cctttgccat gtacccgcca tccatgatcg ccacgggcag      60
cattggggct gcagtg                                                     76

<210> SEQ ID NO 16
<211> LENGTH: 71
<212> TYPE: DNA
<213> ORGANISM: Homo sapiens

<400> SEQUENCE: 16
aaagaagatg atgaccgggt tacccaaac tcaacgtgca agcctcggat tattgcacca      60
tccagaggct c                                                          71

<210> SEQ ID NO 17
<211> LENGTH: 82
<212> TYPE: DNA
<213> ORGANISM: Homo sapiens

<400> SEQUENCE: 17
atgctgtggc tccttcctaa ctggggcttt cttgacatgt aggttgcttg gtaataacct     60
ttttgtatat cacaatttgg gt                                              82

<210> SEQ ID NO 18
<211> LENGTH: 75
<212> TYPE: DNA
<213> ORGANISM: Homo sapiens

<400> SEQUENCE: 18
gcaggtgtca gcaagtatga tcagcaatga ggcggtggtc aatatcctgt cgagctcatc     60
accacagcgg aaaaa                                                      75

<210> SEQ ID NO 19
<211> LENGTH: 72
<212> TYPE: DNA
<213> ORGANISM: Homo sapiens

<400> SEQUENCE: 19
gcccagtgcg gagaacaggt ccagcttgat tctcgtctct gcacttaagc tgttctccag     60
gtgcgtgtga tt                                                         72

<210> SEQ ID NO 20
<211> LENGTH: 90
<212> TYPE: DNA
<213> ORGANISM: Homo sapiens

<400> SEQUENCE: 20
atcaccgaca gcacagacag aatccctgct accaatatgg actccagtca tagtacaacg     60
cttcagccta ctgcaaatcc aaacacaggt                                      90

<210> SEQ ID NO 21
<211> LENGTH: 78
<212> TYPE: DNA
<213> ORGANISM: Homo sapiens

<400> SEQUENCE: 21
gacgaagaca gtccctggat caccgacagc acagacagaa tccctgctac cagagaccaa     60
```

```
gacacattcc accccagt                                              78
```

<210> SEQ ID NO 22
<211> LENGTH: 69
<212> TYPE: DNA
<213> ORGANISM: Homo sapiens

<400> SEQUENCE: 22

```
cacacaaaac agaaccagga ctggacccag tggaacccaa gccattcaaa tccggaagtg   60
ctacttcag                                                         69
```

<210> SEQ ID NO 23
<211> LENGTH: 78
<212> TYPE: DNA
<213> ORGANISM: Homo sapiens

<400> SEQUENCE: 23

```
ctcataccag ccatccaatg caaggaagga caacaccaag cccagaggac agttcctgga   60
ctgatttctt caacccaa                                               78
```

<210> SEQ ID NO 24
<211> LENGTH: 74
<212> TYPE: DNA
<213> ORGANISM: Homo sapiens

<400> SEQUENCE: 24

```
tggttcccag ccctgtgtcc acctccaagc ccagattcag attcgagtca tgtacacaac   60
ccagggtgga ggag                                                   74
```

<210> SEQ ID NO 25
<211> LENGTH: 84
<212> TYPE: DNA
<213> ORGANISM: Homo sapiens

<400> SEQUENCE: 25

```
gtgcaggctc aggtgaagtg ctgcggctgg gtcagcttct acaactggac agacaacgct   60
gagctcatga atcgccctga ggtc                                        84
```

<210> SEQ ID NO 26
<211> LENGTH: 64
<212> TYPE: DNA
<213> ORGANISM: Homo sapiens

<400> SEQUENCE: 26

```
gggcgtggaa cagtttatct cagacatctg ccccaagaag gacgtactcg aaaccttcac   60
cgtg                                                              64
```

<210> SEQ ID NO 27
<211> LENGTH: 85
<212> TYPE: DNA
<213> ORGANISM: Homo sapiens

<400> SEQUENCE: 27

```
aaacgagcag tttgccatca gacgcttcca gtctatgccg gtgaggctgc tgggccacag   60
ccccgtgctt cggaacatca ccaac                                       85
```

<210> SEQ ID NO 28
<211> LENGTH: 72
<212> TYPE: DNA
<213> ORGANISM: Homo sapiens

```
<400> SEQUENCE: 28
cacagcctca cttctaacct tctggaaccc acccaccact gccaagctca ctattgaatc    60
cacgccattc aa                                                       72

<210> SEQ ID NO 29
<211> LENGTH: 76
<212> TYPE: DNA
<213> ORGANISM: Homo sapiens

<400> SEQUENCE: 29
ctgaaggagc tccaagacct cgctctccaa ggcgccaagg agagggcaca tcagcagaag    60
aaacacagcg gttttg                                                   76

<210> SEQ ID NO 30
<211> LENGTH: 78
<212> TYPE: DNA
<213> ORGANISM: Homo sapiens

<400> SEQUENCE: 30
atgtggaacc cccacctact tggcgcctga agttcttgtt tctgttggga ctgctgggta    60
taaccgtgct gtggactg                                                 78

<210> SEQ ID NO 31
<211> LENGTH: 86
<212> TYPE: DNA
<213> ORGANISM: Homo sapiens

<400> SEQUENCE: 31
gacatttcca gtcctgcagt caatgcctct ctgccccacc ctttgttcag tgtggctggt    60
gccacgacaa atgtgtgcga tcggag                                        86

<210> SEQ ID NO 32
<211> LENGTH: 79
<212> TYPE: DNA
<213> ORGANISM: Homo sapiens

<400> SEQUENCE: 32
tctgcagagt tggaagcact ctatggtgac atcgatgctg tggagctgta tcctgccctt    60
ctggtagaaa agcctcggc                                                79

<210> SEQ ID NO 33
<211> LENGTH: 65
<212> TYPE: DNA
<213> ORGANISM: Homo sapiens

<400> SEQUENCE: 33
gggtctgtgc cccatgacac ctggctgccc aagaagtgtt ccctgtgtaa atgctggcac    60
ggtca                                                               65

<210> SEQ ID NO 34
<211> LENGTH: 74
<212> TYPE: DNA
<213> ORGANISM: Homo sapiens

<400> SEQUENCE: 34
gggaggctta tctcactgag tgagcagaat ctggtagact gctctgggcc tcaaggcaat    60
gaaggctgca atgg                                                     74
```

```
<210> SEQ ID NO 35
<211> LENGTH: 72
<212> TYPE: DNA
<213> ORGANISM: Homo sapiens

<400> SEQUENCE: 35
gaccaaggtc ctggaatgtc tgcagcagaa ggtgaatggc atcctggaga gccctacggg    60
tacagggaag ac                                                        72

<210> SEQ ID NO 36
<211> LENGTH: 73
<212> TYPE: DNA
<213> ORGANISM: Homo sapiens

<400> SEQUENCE: 36
cacaatggcg gctctgaaga gttggctgtc gcgcagcgta acttcattct tcaggtacag    60
acagtgtttg tgt                                                       73

<210> SEQ ID NO 37
<211> LENGTH: 87
<212> TYPE: DNA
<213> ORGANISM: Homo sapiens

<400> SEQUENCE: 37
aggacgcaag gagggtttgt cactggcaga ctcgagactg taggcactgc catggcccct    60
gtgctcagta aggactcggc ggacatc                                        87

<210> SEQ ID NO 38
<211> LENGTH: 84
<212> TYPE: DNA
<213> ORGANISM: Homo sapiens

<400> SEQUENCE: 38
ctctgagaca gtgcttcgat gactttgcag acttggtgcc ctttgactcc tgggagccgc    60
tcatgaggaa gttgggcctc atgg                                           84

<210> SEQ ID NO 39
<211> LENGTH: 73
<212> TYPE: DNA
<213> ORGANISM: Homo sapiens

<400> SEQUENCE: 39
tgccacctgg acatcatttg ggtcaacact cccgagcacg ttgttccgta tggacttgga    60
agccctaggt cca                                                       73

<210> SEQ ID NO 40
<211> LENGTH: 62
<212> TYPE: DNA
<213> ORGANISM: Homo sapiens

<400> SEQUENCE: 40
tgtcgatgga cttccagaac cacctgggca gctgccaaaa gtgtgatcca agctgtccca    60
at                                                                   62

<210> SEQ ID NO 41
<211> LENGTH: 72
<212> TYPE: DNA
<213> ORGANISM: Homo sapiens

<400> SEQUENCE: 41
gagtcgggct ctggaggaaa agaaaggtaa ttatgtggtg acagatcacg gctcgtgcgt    60
```

```
ccgagcctgt gg                                                          72

<210> SEQ ID NO 42
<211> LENGTH: 82
<212> TYPE: DNA
<213> ORGANISM: Homo sapiens

<400> SEQUENCE: 42
gatctaagat ggcgactgtc gaaccggaaa ccaccccctac tcctaatccc ccgactacag    60
aagaggagaa aacggaatct aa                                              82

<210> SEQ ID NO 43
<211> LENGTH: 81
<212> TYPE: DNA
<213> ORGANISM: Homo sapiens

<400> SEQUENCE: 43
cggttatgtc atgccagata cacacctcaa aggtactccc tcctcccggg aaggcaccct    60
ttcttcagtg ggtctcagtt c                                               81

<210> SEQ ID NO 44
<211> LENGTH: 86
<212> TYPE: DNA
<213> ORGANISM: Homo sapiens

<400> SEQUENCE: 44
tggctcttaa tcagtttcgt tacctgcctc tggagaattt acgcattatt cgtgggacaa    60
aactttatga ggatcgatat gccttg                                          86

<210> SEQ ID NO 45
<211> LENGTH: 91
<212> TYPE: DNA
<213> ORGANISM: Homo sapiens

<400> SEQUENCE: 45
ataacaaagt gtagctctga catgaatggc tattgtttgc atggacagtg catctatctg    60
gtggacatga gtcaaaacta ctgcaggtgt g                                    91

<210> SEQ ID NO 46
<211> LENGTH: 67
<212> TYPE: DNA
<213> ORGANISM: Homo sapiens

<400> SEQUENCE: 46
acggatcaca gtggaggaag cgctggctca cccctacctg gagcagtact atgacccgac    60
ggatgag                                                               67

<210> SEQ ID NO 47
<211> LENGTH: 91
<212> TYPE: DNA
<213> ORGANISM: Homo sapiens

<400> SEQUENCE: 47
ggattgctca acaaccatgc tgggcatctg gaccctccta cctctggttc ttacgtctgt    60
tgctagatta tcgtccaaaa gtgttaatgc c                                    91

<210> SEQ ID NO 48
<211> LENGTH: 75
<212> TYPE: DNA
<213> ORGANISM: Homo sapiens
```

```
<400> SEQUENCE: 48
ttggtacctg tgggttagca tcaagttctc cccagggtag aattcaatca gagctccagt    60
ttgcatttgg atgtg                                                     75

<210> SEQ ID NO 49
<211> LENGTH: 68
<212> TYPE: DNA
<213> ORGANISM: Homo sapiens

<400> SEQUENCE: 49
tgatgcgcct ggaaacagtc agcaggcaac tccgaaggac aacgagataa gcacctttca    60
caacctcg                                                             68

<210> SEQ ID NO 50
<211> LENGTH: 73
<212> TYPE: DNA
<213> ORGANISM: Homo sapiens

<400> SEQUENCE: 50
cgaaaagatg ctgaacagtg acaaatccaa ctgaccagaa gggaggagga agctcactgg    60
tggctgttcc tga                                                       73

<210> SEQ ID NO 51
<211> LENGTH: 73
<212> TYPE: DNA
<213> ORGANISM: Homo sapiens

<400> SEQUENCE: 51
cccactcagt agccaagtca caatgtttgg aaaacagccc gtttacttga gcaagactga    60
taccacctgc gtg                                                       73

<210> SEQ ID NO 52
<211> LENGTH: 80
<212> TYPE: DNA
<213> ORGANISM: Homo sapiens

<400> SEQUENCE: 52
gactccttcg tccccagttg ccgtctagga ttgggcctcc cataattgct ttgccaaaat    60
accagagcct tcaagtgcca                                                80

<210> SEQ ID NO 53
<211> LENGTH: 70
<212> TYPE: DNA
<213> ORGANISM: Homo sapiens

<400> SEQUENCE: 53
cggtgtgaga agtgcagcaa gccctgtgcc cgagtgtgct atggtctggg catggagcac    60
ttgcgagagg                                                           70

<210> SEQ ID NO 54
<211> LENGTH: 65
<212> TYPE: DNA
<213> ORGANISM: Homo sapiens

<400> SEQUENCE: 54
ccgaaatcca gatgatgatg ctcatggacc ctggtgctac acgggaaatc cactcattcc    60
ttggg                                                                65
```

```
<210> SEQ ID NO 55
<211> LENGTH: 70
<212> TYPE: DNA
<213> ORGANISM: Homo sapiens

<400> SEQUENCE: 55
agaaccgcaa ggtgagcaag gtggagattc tccagcacgt catcgactac atcagggacc    60
ttcagttgga                                                           70

<210> SEQ ID NO 56
<211> LENGTH: 83
<212> TYPE: DNA
<213> ORGANISM: Homo sapiens

<400> SEQUENCE: 56
gcatggtagc cgaagatttc acagtcaaaa tcggagattt tggtatgacg cgagatatct    60
atgagacaga ctattaccgg aaa                                            83

<210> SEQ ID NO 57
<211> LENGTH: 68
<212> TYPE: DNA
<213> ORGANISM: Homo sapiens

<400> SEQUENCE: 57
acgcaccggg tgtctgatcc caagttccac ccctccatt caaagataat catcatcaag     60
aaagggca                                                             68

<210> SEQ ID NO 58
<211> LENGTH: 74
<212> TYPE: DNA
<213> ORGANISM: Homo sapiens

<400> SEQUENCE: 58
ccacagctca ccttctgtca ggtgtccatc ccagctccag ccagctccca gagaggaaga    60
gactggcact gagg                                                      74

<210> SEQ ID NO 59
<211> LENGTH: 77
<212> TYPE: DNA
<213> ORGANISM: Homo sapiens

<400> SEQUENCE: 59
ccatgatcct cactctgctg gtggactata cactccagac ctcgcttagc atggtaaatc    60
accggctaca aagcttc                                                   77

<210> SEQ ID NO 60
<211> LENGTH: 78
<212> TYPE: DNA
<213> ORGANISM: Homo sapiens

<400> SEQUENCE: 60
accgggagcc ctacatgacc gaaaatacct gcaaccgtta ctgccgtgac gagattgagt    60
cagtgaaaga gcttaagg                                                  78

<210> SEQ ID NO 61
<211> LENGTH: 73
<212> TYPE: DNA
<213> ORGANISM: Homo sapiens

<400> SEQUENCE: 61
cgaggattgg ttcttcagca agacagagga actgaaccgc gaggtggcca ccaacagtga    60
```

```
gctggtgcag agt                                                           73

<210> SEQ ID NO 62
<211> LENGTH: 80
<212> TYPE: DNA
<213> ORGANISM: Homo sapiens

<400> SEQUENCE: 62
actcaagcgg aaattgaagc agataggtct tatcagcaca gtctccgcct cctggattca        60
gtgtctcggc ttcagggagt                                                    80

<210> SEQ ID NO 63
<211> LENGTH: 77
<212> TYPE: DNA
<213> ORGANISM: Homo sapiens

<400> SEQUENCE: 63
ccgccctcac ctgaagagaa acgcgctcct tggcggacac tgggggagga gaggaagaag        60
cgcggctaac ttattcc                                                       77

<210> SEQ ID NO 64
<211> LENGTH: 78
<212> TYPE: DNA
<213> ORGANISM: Homo sapiens

<400> SEQUENCE: 64
tgagcgtcgc agaaaccaca acatcctgga gcgccagcgc cgcaacgacc ttcggtccag        60
ctttctcacg ctcaggga                                                      78

<210> SEQ ID NO 65
<211> LENGTH: 70
<212> TYPE: DNA
<213> ORGANISM: Homo sapiens

<400> SEQUENCE: 65
gcggaaggtc cctcagacat ccccgattga aagaaccaga gaggctctga gaaacctcgg        60
gaaacttaga                                                               70

<210> SEQ ID NO 66
<211> LENGTH: 66
<212> TYPE: DNA
<213> ORGANISM: Homo sapiens

<400> SEQUENCE: 66
cggtggacca cgaagagtta acccgggact tggagaagca ctgcagagac atggaagagg        60
cgagcc                                                                   66

<210> SEQ ID NO 67
<211> LENGTH: 68
<212> TYPE: DNA
<213> ORGANISM: Homo sapiens

<400> SEQUENCE: 67
ctttgaaccc ttgcttgcaa taggtgtgcg tcagaagcac ccaggacttc catttgcttt        60
gtcccggg                                                                 68

<210> SEQ ID NO 68
<211> LENGTH: 81
<212> TYPE: DNA
<213> ORGANISM: Homo sapiens
```

<400> SEQUENCE: 68
ccgcaacgtg gttttctcac cctatggggt ggcctcggtg ttggccatgc tccagctgac    60
aacaggagga gaaacccagc a                                              81

<210> SEQ ID NO 69
<211> LENGTH: 67
<212> TYPE: DNA
<213> ORGANISM: Homo sapiens

<400> SEQUENCE: 69
ttgttggtgt gccctggtgc cgtggtggcg gtcactccct ctgctgccag tgtttggaca    60
gaaccca                                                              67

<210> SEQ ID NO 70
<211> LENGTH: 62
<212> TYPE: DNA
<213> ORGANISM: Homo sapiens

<400> SEQUENCE: 70
actgaaggag acccttggag cctaggggca tcggcaggag agtgtgtggg cagggttatt    60
ta                                                                   62

<210> SEQ ID NO 71
<211> LENGTH: 74
<212> TYPE: DNA
<213> ORGANISM: Homo sapiens

<400> SEQUENCE: 71
agagccagtt gctgtagaac tcaaatctct gctgggcaag gatgttctgt tcttgaagga    60
ctgtgtaggc ccag                                                      74

<210> SEQ ID NO 72
<211> LENGTH: 76
<212> TYPE: DNA
<213> ORGANISM: Homo sapiens

<400> SEQUENCE: 72
cccatggatg ctcctctgaa gagactttcc tcattgactg ccgaggcccc atgaatcaat    60
gtctggtagc caccgg                                                    76

<210> SEQ ID NO 73
<211> LENGTH: 72
<212> TYPE: DNA
<213> ORGANISM: Homo sapiens

<400> SEQUENCE: 73
tgactttatg gagcccaagt ttgagtttgc tgtgaagttc aatgcactgg aattagatga    60
cagcgacttg gc                                                        72

<210> SEQ ID NO 74
<211> LENGTH: 81
<212> TYPE: DNA
<213> ORGANISM: Homo sapiens

<400> SEQUENCE: 74
cgcttgccta actcatactt tcccgttgac acttgatcca cgcagcgtgg cactgggacg    60
taagtggcgc agtctgaatg g                                              81

```
<210> SEQ ID NO 75
<211> LENGTH: 73
<212> TYPE: DNA
<213> ORGANISM: Homo sapiens

<400> SEQUENCE: 75
tccttcagct ttcacactgg gctcagaaat gaagttgcat gactcttctg gaagtcaggt    60
gggaacagga ttt                                                      73

<210> SEQ ID NO 76
<211> LENGTH: 69
<212> TYPE: DNA
<213> ORGANISM: Homo sapiens

<400> SEQUENCE: 76
agtgggagac acctgacctt tctcaagctg agattgagca aagatcaag gagtacaatg     60 cccagatca                                                           69

<210> SEQ ID NO 77
<211> LENGTH: 77
<212> TYPE: DNA
<213> ORGANISM: Homo sapiens

<400> SEQUENCE: 77
cgaagccctt acaagtttcc tagttcaccc ttacggattc ctggagggaa catctatatt   60
tcacccctga agagtcc                                                  77

<210> SEQ ID NO 78
<211> LENGTH: 74
<212> TYPE: DNA
<213> ORGANISM: Homo sapiens

<400> SEQUENCE: 78
ccagacgagc gattagaagc ggcagcttgt gaggtgaatg atttggggga agaggaggag   60
gaggaagagg agga                                                     74

<210> SEQ ID NO 79
<211> LENGTH: 75
<212> TYPE: DNA
<213> ORGANISM: Homo sapiens

<400> SEQUENCE: 79
ccattctatc atcaacgggt acaaacgagt cctggccttg tctgtggaga cggattacac   60
cttcccactt gctga                                                    75

<210> SEQ ID NO 80
<211> LENGTH: 66
<212> TYPE: DNA
<213> ORGANISM: Homo sapiens

<400> SEQUENCE: 80
tgtggcaagt gcaaatgtaa ggagtgcacc tacccaaggc ctctgccatc agactggatc   60
tgcgac                                                              66

<210> SEQ ID NO 81
<211> LENGTH: 64
<212> TYPE: DNA
<213> ORGANISM: Homo sapiens

<400> SEQUENCE: 81
cctgaacatg aaggagctga agctgctgca gaccatcggg aagggggagt tcggagacgt   60
``` gatg                                                                    64

<210> SEQ ID NO 82
<211> LENGTH: 69
<212> TYPE: DNA
<213> ORGANISM: Homo sapiens

<400> SEQUENCE: 82
catcttccag gaggaccact ctctgtggca ccctggacta cctgccccct gaaatgattg      60
aaggtcgga                                                              69

<210> SEQ ID NO 83
<211> LENGTH: 80
<212> TYPE: DNA
<213> ORGANISM: Homo sapiens

<400> SEQUENCE: 83
tgttttgatt cccgggctta ccaggtgaga agtgagggag gaagaaggca gtgtcccttt      60
tgctagagct gacagctttg                                                  80

<210> SEQ ID NO 84
<211> LENGTH: 79
<212> TYPE: DNA
<213> ORGANISM: Homo sapiens

<400> SEQUENCE: 84
aagaggaacg gagcgagtcc ccgcgcgcgg cgcgattccc tgagctgtgg gacgtgcacc      60
caggactcgg ctcacacat                                                   79

<210> SEQ ID NO 85
<211> LENGTH: 68
<212> TYPE: DNA
<213> ORGANISM: Homo sapiens

<400> SEQUENCE: 85
gccaactgct ttcatttgtg agggatctga accaatacag agcagacata aaggaaatgg      60
gcctgagt                                                               68

<210> SEQ ID NO 86
<211> LENGTH: 66
<212> TYPE: DNA
<213> ORGANISM: Homo sapiens

<400> SEQUENCE: 86
aacaccaatg ggttccatct ttctgggctc ctgattgctc aagcacagtt tggcctgatg      60
aagagg                                                                 66

<210> SEQ ID NO 87
<211> LENGTH: 69
<212> TYPE: DNA
<213> ORGANISM: Homo sapiens

<400> SEQUENCE: 87
tcaccctctg tgacttcatc gtgccctggg acaccctgag caccacccag aagaagagcc      60
tgaaccaca                                                              69

<210> SEQ ID NO 88
<211> LENGTH: 70
<212> TYPE: DNA
<213> ORGANISM: Homo sapiens

```
<400> SEQUENCE: 88
cgactccgtt ctcagtgtct gacatcttga gtcccctgga ggaaagctac aagaaagtgg      60
gcatggaggg                                                            70

<210> SEQ ID NO 89
<211> LENGTH: 74
<212> TYPE: DNA
<213> ORGANISM: Homo sapiens

<400> SEQUENCE: 89
tgctgttgct gagtctgttg ccagtcccca gaagaccatg tctgtgttga gctgtatctg      60
tgaagccagg caag                                                       74

<210> SEQ ID NO 90
<211> LENGTH: 70
<212> TYPE: DNA
<213> ORGANISM: Homo sapiens

<400> SEQUENCE: 90
gtggatgtgc cctgaaggac aagccaggcg tctacacgag agtctcacac ttcttaccct      60
ggatccgcag                                                            70

<210> SEQ ID NO 91
<211> LENGTH: 83
<212> TYPE: DNA
<213> ORGANISM: Homo sapiens

<400> SEQUENCE: 91
cctcagcaag acgttatttg aaattacagt gcctctctct caaggcccca aaccagtaac      60
aatcagtttt gccaatcaca ctt                                             83

<210> SEQ ID NO 92
<211> LENGTH: 77
<212> TYPE: DNA
<213> ORGANISM: Homo sapiens

<400> SEQUENCE: 92
gcagttggaa gacacaggaa agtatcccca aattgcagat ttatcaacgg cttttatctt      60
gaaaatagtg ccacgca                                                    77

<210> SEQ ID NO 93
<211> LENGTH: 76
<212> TYPE: DNA
<213> ORGANISM: Homo sapiens

<400> SEQUENCE: 93
agactgtgga gtttgatgtt gttgaaggag aaaagggtgc ggaggcagca aatgttacag      60
gtcctggtgg tgttcc                                                     76

<210> SEQ ID NO 94
<211> LENGTH: 23
<212> TYPE: DNA
<213> ORGANISM: Artificial Sequence
<220> FEATURE:
<223> OTHER INFORMATION: primer

<400> SEQUENCE: 94
cgttccgatc tctctatactg cat                                            23
```

```
<210> SEQ ID NO 95
<211> LENGTH: 22
<212> TYPE: DNA
<213> ORGANISM: Artificial Sequence
<220> FEATURE:
<223> OTHER INFORMATION: primer

<400> SEQUENCE: 95
aggtccctgt tggccttata gg                                          22

<210> SEQ ID NO 96
<211> LENGTH: 25
<212> TYPE: DNA
<213> ORGANISM: Artificial Sequence
<220> FEATURE:
<223> OTHER INFORMATION: primer

<400> SEQUENCE: 96
atgcctacag caccctgatg tcgca                                       25

<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
cgcttctatg gcgctgagat                                             20

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
tcccggtaca ccacgttctt                                             20

<210> SEQ ID NO 99
<211> LENGTH: 24
<212> TYPE: DNA
<213> ORGANISM: Artificial Sequence
<220> FEATURE:
<223> OTHER INFORMATION: primer

<400> SEQUENCE: 99
cagccctgga ctacctgcac tcgg                                        24

<210> SEQ ID NO 100
<211> LENGTH: 19
<212> TYPE: DNA
<213> ORGANISM: Artificial Sequence
<220> FEATURE:
<223> OTHER INFORMATION: primer

<400> SEQUENCE: 100
tcctgccacc cttcaaacc                                              19

<210> SEQ ID NO 101
<211> LENGTH: 21
<212> TYPE: DNA
<213> ORGANISM: Artificial Sequence
<220> FEATURE:
<223> OTHER INFORMATION: primer

<400> SEQUENCE: 101
```

-continued

```
ggcggtaaat tcatcatcga a                                              21

<210> SEQ ID NO 102
<211> LENGTH: 24
<212> TYPE: DNA
<213> ORGANISM: Artificial Sequence
<220> FEATURE:
<223> OTHER INFORMATION: primer

<400> SEQUENCE: 102
caggtcacgt ccgaggtcga caca                                           24

<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103
ggacagcagg aatgtgtttc                                                20

<210> SEQ ID NO 104
<211> LENGTH: 20
<212> TYPE: DNA
<213> ORGANISM: Artificial Sequence
<220> FEATURE:
<223> OTHER INFORMATION: primer

<400> SEQUENCE: 104
acccactcga tttgtttctg                                                20

<210> SEQ ID NO 105
<211> LENGTH: 22
<212> TYPE: DNA
<213> ORGANISM: Artificial Sequence
<220> FEATURE:
<223> OTHER INFORMATION: primer

<400> SEQUENCE: 105
cattggctcc ccgtgacctg ta                                             22

<210> SEQ ID NO 106
<211> LENGTH: 22
<212> TYPE: DNA
<213> ORGANISM: Artificial Sequence
<220> FEATURE:
<223> OTHER INFORMATION: primer

<400> SEQUENCE: 106
ggctcttgtg cgtactgtcc tt                                             22

<210> SEQ ID NO 107
<211> LENGTH: 23
<212> TYPE: DNA
<213> ORGANISM: Artificial Sequence
<220> FEATURE:
<223> OTHER INFORMATION: primer

<400> SEQUENCE: 107
tcagatgacg aagagcacag atg                                            23

<210> SEQ ID NO 108
<211> LENGTH: 29
<212> TYPE: DNA
<213> ORGANISM: Artificial Sequence
```

```
<220> FEATURE:
<223> OTHER INFORMATION: primer

<400> SEQUENCE: 108
aggctcagtg atgtcttccc tgtcaccag                                   29

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
ccattcccac cattctacct                                             20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
gggaacatag acccaccaat                                             20

<210> SEQ ID NO 111
<211> LENGTH: 21
<212> TYPE: DNA
<213> ORGANISM: Artificial Sequence
<220> FEATURE:
<223> OTHER INFORMATION: primer

<400> SEQUENCE: 111
acaccccaga cgtcctggcc t                                           21

<210> SEQ ID NO 112
<211> LENGTH: 18
<212> TYPE: DNA
<213> ORGANISM: Artificial Sequence
<220> FEATURE:
<223> OTHER INFORMATION: primer

<400> SEQUENCE: 112
ccgccgtgga cacagact                                               18

<210> SEQ ID NO 113
<211> LENGTH: 21
<212> TYPE: DNA
<213> ORGANISM: Artificial Sequence
<220> FEATURE:
<223> OTHER INFORMATION: primer

<400> SEQUENCE: 113
ttgccgtcag aaaacatgtc a                                           21

<210> SEQ ID NO 114
<211> LENGTH: 25
<212> TYPE: DNA
<213> ORGANISM: Artificial Sequence
<220> FEATURE:
<223> OTHER INFORMATION: primer

<400> SEQUENCE: 114
tgccactcgg aaaaagacct ctcgg                                       25
```

```
<210> SEQ ID NO 115
<211> LENGTH: 24
<212> TYPE: DNA
<213> ORGANISM: Artificial Sequence
<220> FEATURE:
<223> OTHER INFORMATION: primer

<400> SEQUENCE: 115
cttttgtgga actctatggg aaca                                         24

<210> SEQ ID NO 116
<211> LENGTH: 19
<212> TYPE: DNA
<213> ORGANISM: Artificial Sequence
<220> FEATURE:
<223> OTHER INFORMATION: primer

<400> SEQUENCE: 116
cagcggttga agcgttcct                                               19

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
ttcggctctc ggctgctgca                                              20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
ccttccgacc agcagatgaa                                              20

<210> SEQ ID NO 119
<211> LENGTH: 24
<212> TYPE: DNA
<213> ORGANISM: Artificial Sequence
<220> FEATURE:
<223> OTHER INFORMATION: primer

<400> SEQUENCE: 119
tttatatgca cattgggagc tgat                                         24

<210> SEQ ID NO 120
<211> LENGTH: 25
<212> TYPE: DNA
<213> ORGANISM: Artificial Sequence
<220> FEATURE:
<223> OTHER INFORMATION: primer

<400> SEQUENCE: 120
caatttgggc aacgagaccg atcct                                        25

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
```
gtgcaggaaa ggttcacaaa                                              20

<210> SEQ ID NO 122
<211> LENGTH: 20
<212> TYPE: DNA
<213> ORGANISM: Artificial Sequence
<220> FEATURE:
<223> OTHER INFORMATION: primer

<400> SEQUENCE: 122
gcacacacga tggagtaagg                                              20

<210> SEQ ID NO 123
<211> LENGTH: 24
<212> TYPE: DNA
<213> ORGANISM: Artificial Sequence
<220> FEATURE:
<223> OTHER INFORMATION: primer

<400> SEQUENCE: 123
agtgtctgcg tccaatacac gcgt                                         24

<210> SEQ ID NO 124
<211> LENGTH: 18
<212> TYPE: DNA
<213> ORGANISM: Artificial Sequence
<220> FEATURE:
<223> OTHER INFORMATION: primer

<400> SEQUENCE: 124
agggagatgc cgcttcgt                                                18

<210> SEQ ID NO 125
<211> LENGTH: 23
<212> TYPE: DNA
<213> ORGANISM: Artificial Sequence
<220> FEATURE:
<223> OTHER INFORMATION: primer

<400> SEQUENCE: 125
ctctcacacc ttgctccaat gta                                          23

<210> SEQ ID NO 126
<211> LENGTH: 25
<212> TYPE: DNA
<213> ORGANISM: Artificial Sequence
<220> FEATURE:
<223> OTHER INFORMATION: primer

<400> SEQUENCE: 126
ccttcatcac agacacagga gggcg                                        25

<210> SEQ ID NO 127
<211> LENGTH: 20
<212> TYPE: DNA
<213> ORGANISM: Artificial Sequence
<220> FEATURE:
<223> OTHER INFORMATION: primer

<400> SEQUENCE: 127
atcctagccc tggtttttgg                                              20

<210> SEQ ID NO 128
<211> LENGTH: 20
<212> TYPE: DNA
<213> ORGANISM: Artificial Sequence

```
<220> FEATURE:
<223> OTHER INFORMATION: primer

<400> SEQUENCE: 128
ctgccttctc atctgcacaa                                              20

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
tttgctgtca ccagcgtcgc                                              20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
gaaggccaag aaccgagtca                                              20

<210> SEQ ID NO 131
<211> LENGTH: 24
<212> TYPE: DNA
<213> ORGANISM: Artificial Sequence
<220> FEATURE:
<223> OTHER INFORMATION: primer

<400> SEQUENCE: 131
tccccagtta gttcaaaagt caca                                         24

<210> SEQ ID NO 132
<211> LENGTH: 27
<212> TYPE: DNA
<213> ORGANISM: Artificial Sequence
<220> FEATURE:
<223> OTHER INFORMATION: primer

<400> SEQUENCE: 132
ttatattcca gtttaaggcc aatcctc                                      27

<210> SEQ ID NO 133
<211> LENGTH: 25
<212> TYPE: DNA
<213> ORGANISM: Artificial Sequence
<220> FEATURE:
<223> OTHER INFORMATION: primer

<400> SEQUENCE: 133
ccatacctca agtatttgcc atcag                                        25

<210> SEQ ID NO 134
<211> LENGTH: 22
<212> TYPE: DNA
<213> ORGANISM: Artificial Sequence
<220> FEATURE:
<223> OTHER INFORMATION: primer

<400> SEQUENCE: 134
agctttgtcc cgtgactgtg ta                                           22
```

```
<210> SEQ ID NO 135
<211> LENGTH: 29
<212> TYPE: DNA
<213> ORGANISM: Artificial Sequence
<220> FEATURE:
<223> OTHER INFORMATION: primer

<400> SEQUENCE: 135
attgctggag ctgcctttca tttagcact                              29

<210> SEQ ID NO 136
<211> LENGTH: 27
<212> TYPE: DNA
<213> ORGANISM: Artificial Sequence
<220> FEATURE:
<223> OTHER INFORMATION: primer

<400> SEQUENCE: 136
cctctgtgct acagattata cctttgc                                27

<210> SEQ ID NO 137
<211> LENGTH: 18
<212> TYPE: DNA
<213> ORGANISM: Artificial Sequence
<220> FEATURE:
<223> OTHER INFORMATION: primer

<400> SEQUENCE: 137
cactgcagcc ccaatgct                                          18

<210> SEQ ID NO 138
<211> LENGTH: 22
<212> TYPE: DNA
<213> ORGANISM: Artificial Sequence
<220> FEATURE:
<223> OTHER INFORMATION: primer

<400> SEQUENCE: 138
tacccgccat ccatgatcgc ca                                     22

<210> SEQ ID NO 139
<211> LENGTH: 24
<212> TYPE: DNA
<213> ORGANISM: Artificial Sequence
<220> FEATURE:
<223> OTHER INFORMATION: primer

<400> SEQUENCE: 139
aaagaagatg atgaccgggt ttac                                   24

<210> SEQ ID NO 140
<211> LENGTH: 20
<212> TYPE: DNA
<213> ORGANISM: Artificial Sequence
<220> FEATURE:
<223> OTHER INFORMATION: primer

<400> SEQUENCE: 140
gagcctctgg atggtgcaat                                        20

<210> SEQ ID NO 141
<211> LENGTH: 24
<212> TYPE: DNA
<213> ORGANISM: Artificial Sequence
<220> FEATURE:
<223> OTHER INFORMATION: primer

<400> SEQUENCE: 141
```

```
caaactcaac gtgcaagcct cgga                                          24

<210> SEQ ID NO 142
<211> LENGTH: 22
<212> TYPE: DNA
<213> ORGANISM: Artificial Sequence
<220> FEATURE:
<223> OTHER INFORMATION: primer

<400> SEQUENCE: 142
atgctgtggc tccttcctaa ct                                            22

<210> SEQ ID NO 143
<211> LENGTH: 27
<212> TYPE: DNA
<213> ORGANISM: Artificial Sequence
<220> FEATURE:
<223> OTHER INFORMATION: primer

<400> SEQUENCE: 143
acccaaattg tgatatacaa aaaggtt                                       27

<210> SEQ ID NO 144
<211> LENGTH: 30
<212> TYPE: DNA
<213> ORGANISM: Artificial Sequence
<220> FEATURE:
<223> OTHER INFORMATION: primer

<400> SEQUENCE: 144
taccaagcaa cctacatgtc aagaaagccc                                    30

<210> SEQ ID NO 145
<211> LENGTH: 24
<212> TYPE: DNA
<213> ORGANISM: Artificial Sequence
<220> FEATURE:
<223> OTHER INFORMATION: primer

<400> SEQUENCE: 145
gcaggtgtca gcaagtatga tcag                                          24

<210> SEQ ID NO 146
<211> LENGTH: 20
<212> TYPE: DNA
<213> ORGANISM: Artificial Sequence
<220> FEATURE:
<223> OTHER INFORMATION: primer

<400> SEQUENCE: 146
tttttccgct gtggtgatga                                               20

<210> SEQ ID NO 147
<211> LENGTH: 27
<212> TYPE: DNA
<213> ORGANISM: Artificial Sequence
<220> FEATURE:
<223> OTHER INFORMATION: primer

<400> SEQUENCE: 147
cgacaggata ttgaccaccg cctcatt                                       27

<210> SEQ ID NO 148
<211> LENGTH: 18
<212> TYPE: DNA
<213> ORGANISM: Artificial Sequence
```

```
<220> FEATURE:
<223> OTHER INFORMATION: primer

<400> SEQUENCE: 148
gcccagtgcg gagaacag                                                    18

<210> SEQ ID NO 149
<211> LENGTH: 21
<212> TYPE: DNA
<213> ORGANISM: Artificial Sequence
<220> FEATURE:
<223> OTHER INFORMATION: primer

<400> SEQUENCE: 149
aatcacacgc acctggagaa c                                                21

<210> SEQ ID NO 150
<211> LENGTH: 30
<212> TYPE: DNA
<213> ORGANISM: Artificial Sequence
<220> FEATURE:
<223> OTHER INFORMATION: primer

<400> SEQUENCE: 150
ccagcttgat tctcgtctct gcacttaagc                                       30

<210> SEQ ID NO 151
<211> LENGTH: 19
<212> TYPE: DNA
<213> ORGANISM: Artificial Sequence
<220> FEATURE:
<223> OTHER INFORMATION: primer

<400> SEQUENCE: 151
atcaccgaca gcacagaca                                                   19

<210> SEQ ID NO 152
<211> LENGTH: 20
<212> TYPE: DNA
<213> ORGANISM: Artificial Sequence
<220> FEATURE:
<223> OTHER INFORMATION: primer

<400> SEQUENCE: 152
acctgtgttt ggatttgcag                                                  20

<210> SEQ ID NO 153
<211> LENGTH: 27
<212> TYPE: DNA
<213> ORGANISM: Artificial Sequence
<220> FEATURE:
<223> OTHER INFORMATION: primer

<400> SEQUENCE: 153
ccctgctacc aatatggact ccagtca                                          27

<210> SEQ ID NO 154
<211> LENGTH: 20
<212> TYPE: DNA
<213> ORGANISM: Artificial Sequence
<220> FEATURE:
<223> OTHER INFORMATION: primer

<400> SEQUENCE: 154
gacgaagaca gtccctggat                                                  20
```

```
<210> SEQ ID NO 155
<211> LENGTH: 20
<212> TYPE: DNA
<213> ORGANISM: Artificial Sequence
<220> FEATURE:
<223> OTHER INFORMATION: primer

<400> SEQUENCE: 155
actggggtgg aatgtgtctt                                               20

<210> SEQ ID NO 156
<211> LENGTH: 24
<212> TYPE: DNA
<213> ORGANISM: Artificial Sequence
<220> FEATURE:
<223> OTHER INFORMATION: primer

<400> SEQUENCE: 156
caccgacagc acagacagaa tccc                                          24

<210> SEQ ID NO 157
<211> LENGTH: 22
<212> TYPE: DNA
<213> ORGANISM: Artificial Sequence
<220> FEATURE:
<223> OTHER INFORMATION: primer

<400> SEQUENCE: 157
cacacaaaac agaaccagga ct                                            22

<210> SEQ ID NO 158
<211> LENGTH: 21
<212> TYPE: DNA
<213> ORGANISM: Artificial Sequence
<220> FEATURE:
<223> OTHER INFORMATION: primer

<400> SEQUENCE: 158
ctgaagtagc acttccggat t                                             21

<210> SEQ ID NO 159
<211> LENGTH: 23
<212> TYPE: DNA
<213> ORGANISM: Artificial Sequence
<220> FEATURE:
<223> OTHER INFORMATION: primer

<400> SEQUENCE: 159
acccagtgga acccaagcca ttc                                           23

<210> SEQ ID NO 160
<211> LENGTH: 20
<212> TYPE: DNA
<213> ORGANISM: Artificial Sequence
<220> FEATURE:
<223> OTHER INFORMATION: primer

<400> SEQUENCE: 160
ctcataccag ccatccaatg                                               20

<210> SEQ ID NO 161
<211> LENGTH: 21
<212> TYPE: DNA
<213> ORGANISM: Artificial Sequence
<220> FEATURE:
<223> OTHER INFORMATION: primer

<400> SEQUENCE: 161
```

```
ttgggttgaa gaaatcagtc c                                          21
```

<210> SEQ ID NO 162
<211> LENGTH: 24
<212> TYPE: DNA
<213> ORGANISM: Artificial Sequence
<220> FEATURE:
<223> OTHER INFORMATION: primer

<400> SEQUENCE: 162

```
caccaagccc agaggacagt tcct                                       24
```

<210> SEQ ID NO 163
<211> LENGTH: 18
<212> TYPE: DNA
<213> ORGANISM: Artificial Sequence
<220> FEATURE:
<223> OTHER INFORMATION: primer

<400> SEQUENCE: 163

```
tggttcccag ccctgtgt                                              18
```

<210> SEQ ID NO 164
<211> LENGTH: 19
<212> TYPE: DNA
<213> ORGANISM: Artificial Sequence
<220> FEATURE:
<223> OTHER INFORMATION: primer

<400> SEQUENCE: 164

```
ctcctccacc ctgggttgt                                             19
```

<210> SEQ ID NO 165
<211> LENGTH: 28
<212> TYPE: DNA
<213> ORGANISM: Artificial Sequence
<220> FEATURE:
<223> OTHER INFORMATION: primer

<400> SEQUENCE: 165

```
ctccaagccc agattcagat tcgagtca                                   28
```

<210> SEQ ID NO 166
<211> LENGTH: 20
<212> TYPE: DNA
<213> ORGANISM: Artificial Sequence
<220> FEATURE:
<223> OTHER INFORMATION: primer

<400> SEQUENCE: 166

```
gtgcaggctc aggtgaagtg                                            20
```

<210> SEQ ID NO 167
<211> LENGTH: 20
<212> TYPE: DNA
<213> ORGANISM: Artificial Sequence
<220> FEATURE:
<223> OTHER INFORMATION: primer

<400> SEQUENCE: 167

```
gacctcaggg cgattcatga                                            20
```

<210> SEQ ID NO 168
<211> LENGTH: 30
<212> TYPE: DNA
<213> ORGANISM: Artificial Sequence

```
<220> FEATURE:
<223> OTHER INFORMATION: primer

<400> SEQUENCE: 168
tcagcttcta caactggaca gacaacgctg                                          30

<210> SEQ ID NO 169
<211> LENGTH: 20
<212> TYPE: DNA
<213> ORGANISM: Artificial Sequence
<220> FEATURE:
<223> OTHER INFORMATION: primer

<400> SEQUENCE: 169
gggcgtggaa cagtttatct                                                     20

<210> SEQ ID NO 170
<211> LENGTH: 19
<212> TYPE: DNA
<213> ORGANISM: Artificial Sequence
<220> FEATURE:
<223> OTHER INFORMATION: primer

<400> SEQUENCE: 170
cacggtgaag gtttcgagt                                                      19

<210> SEQ ID NO 171
<211> LENGTH: 24
<212> TYPE: DNA
<213> ORGANISM: Artificial Sequence
<220> FEATURE:
<223> OTHER INFORMATION: primer

<400> SEQUENCE: 171
agacatctgc cccaagaagg acgt                                                24

<210> SEQ ID NO 172
<211> LENGTH: 21
<212> TYPE: DNA
<213> ORGANISM: Artificial Sequence
<220> FEATURE:
<223> OTHER INFORMATION: primer

<400> SEQUENCE: 172
aaacgagcag tttgccatca g                                                   21

<210> SEQ ID NO 173
<211> LENGTH: 20
<212> TYPE: DNA
<213> ORGANISM: Artificial Sequence
<220> FEATURE:
<223> OTHER INFORMATION: primer

<400> SEQUENCE: 173
gttggtgatg ttccgaagca                                                     20

<210> SEQ ID NO 174
<211> LENGTH: 24
<212> TYPE: DNA
<213> ORGANISM: Artificial Sequence
<220> FEATURE:
<223> OTHER INFORMATION: primer

<400> SEQUENCE: 174
cctcaccggc atagactgga agcg                                                24
```

```
<210> SEQ ID NO 175
<211> LENGTH: 24
<212> TYPE: DNA
<213> ORGANISM: Artificial Sequence
<220> FEATURE:
<223> OTHER INFORMATION: primer

<400> SEQUENCE: 175
cacagcctca cttctaacct tctg                                          24

<210> SEQ ID NO 176
<211> LENGTH: 22
<212> TYPE: DNA
<213> ORGANISM: Artificial Sequence
<220> FEATURE:
<223> OTHER INFORMATION: primer

<400> SEQUENCE: 176
ttgaatggcg tggattcaat ag                                            22

<210> SEQ ID NO 177
<211> LENGTH: 23
<212> TYPE: DNA
<213> ORGANISM: Artificial Sequence
<220> FEATURE:
<223> OTHER INFORMATION: primer

<400> SEQUENCE: 177
acccacccac cactgccaag ctc                                           23

<210> SEQ ID NO 178
<211> LENGTH: 20
<212> TYPE: DNA
<213> ORGANISM: Artificial Sequence
<220> FEATURE:
<223> OTHER INFORMATION: primer

<400> SEQUENCE: 178
ctgaaggagc tccaagacct                                               20

<210> SEQ ID NO 179
<211> LENGTH: 20
<212> TYPE: DNA
<213> ORGANISM: Artificial Sequence
<220> FEATURE:
<223> OTHER INFORMATION: primer

<400> SEQUENCE: 179
caaaaccgct gtgtttcttc                                               20

<210> SEQ ID NO 180
<211> LENGTH: 22
<212> TYPE: DNA
<213> ORGANISM: Artificial Sequence
<220> FEATURE:
<223> OTHER INFORMATION: primer

<400> SEQUENCE: 180
tgctgatgtg ccctctcctt gg                                            22

<210> SEQ ID NO 181
<211> LENGTH: 21
<212> TYPE: DNA
<213> ORGANISM: Artificial Sequence
<220> FEATURE:
<223> OTHER INFORMATION: primer

<400> SEQUENCE: 181
```
atgtggaacc cccacctact t                               21

<210> SEQ ID NO 182
<211> LENGTH: 22
<212> TYPE: DNA
<213> ORGANISM: Artificial Sequence
<220> FEATURE:
<223> OTHER INFORMATION: primer

<400> SEQUENCE: 182
cagtccacag cacggttata cc                              22

<210> SEQ ID NO 183
<211> LENGTH: 29
<212> TYPE: DNA
<213> ORGANISM: Artificial Sequence
<220> FEATURE:
<223> OTHER INFORMATION: primer

<400> SEQUENCE: 183
agtcccaaca gaaacaagaa cttcaggcg                       29

<210> SEQ ID NO 184
<211> LENGTH: 22
<212> TYPE: DNA
<213> ORGANISM: Artificial Sequence
<220> FEATURE:
<223> OTHER INFORMATION: primer

<400> SEQUENCE: 184
gacatttcca gtcctgcagt ca                              22

<210> SEQ ID NO 185
<211> LENGTH: 20
<212> TYPE: DNA
<213> ORGANISM: Artificial Sequence
<220> FEATURE:
<223> OTHER INFORMATION: primer

<400> SEQUENCE: 185
ctccgatcgc acacatttgt                                 20

<210> SEQ ID NO 186
<211> LENGTH: 23
<212> TYPE: DNA
<213> ORGANISM: Artificial Sequence
<220> FEATURE:
<223> OTHER INFORMATION: primer

<400> SEQUENCE: 186
tgcctctctg ccccaccctt tgt                             23

<210> SEQ ID NO 187
<211> LENGTH: 23
<212> TYPE: DNA
<213> ORGANISM: Artificial Sequence
<220> FEATURE:
<223> OTHER INFORMATION: primer

<400> SEQUENCE: 187
tctgcagagt tggaagcact cta                             23

<210> SEQ ID NO 188
<211> LENGTH: 21
<212> TYPE: DNA
<213> ORGANISM: Artificial Sequence

```
<220> FEATURE:
<223> OTHER INFORMATION: primer

<400> SEQUENCE: 188
gccgaggctt ttctaccaga a                                         21

<210> SEQ ID NO 189
<211> LENGTH: 28
<212> TYPE: DNA
<213> ORGANISM: Artificial Sequence
<220> FEATURE:
<223> OTHER INFORMATION: primer

<400> SEQUENCE: 189
caggatacag ctccacagca tcgatgtc                                  28

<210> SEQ ID NO 190
<211> LENGTH: 18
<212> TYPE: DNA
<213> ORGANISM: Artificial Sequence
<220> FEATURE:
<223> OTHER INFORMATION: primer

<400> SEQUENCE: 190
gggtctgtgc cccatgac                                             18

<210> SEQ ID NO 191
<211> LENGTH: 20
<212> TYPE: DNA
<213> ORGANISM: Artificial Sequence
<220> FEATURE:
<223> OTHER INFORMATION: primer

<400> SEQUENCE: 191
tgaccgtgcc agcatttaca                                           20

<210> SEQ ID NO 192
<211> LENGTH: 25
<212> TYPE: DNA
<213> ORGANISM: Artificial Sequence
<220> FEATURE:
<223> OTHER INFORMATION: primer

<400> SEQUENCE: 192
cctggctgcc caagaagtgt tccct                                     25

<210> SEQ ID NO 193
<211> LENGTH: 23
<212> TYPE: DNA
<213> ORGANISM: Artificial Sequence
<220> FEATURE:
<223> OTHER INFORMATION: primer

<400> SEQUENCE: 193
gggaggctta tctcactgag tga                                       23

<210> SEQ ID NO 194
<211> LENGTH: 19
<212> TYPE: DNA
<213> ORGANISM: Artificial Sequence
<220> FEATURE:
<223> OTHER INFORMATION: primer

<400> SEQUENCE: 194
ccattgcagc cttcattgc                                            19
```

```
<210> SEQ ID NO 195
<211> LENGTH: 29
<212> TYPE: DNA
<213> ORGANISM: Artificial Sequence
<220> FEATURE:
<223> OTHER INFORMATION: primer

<400> SEQUENCE: 195
ttgaggccca gagcagtcta ccagattct                              29

<210> SEQ ID NO 196
<211> LENGTH: 20
<212> TYPE: DNA
<213> ORGANISM: Artificial Sequence
<220> FEATURE:
<223> OTHER INFORMATION: primer

<400> SEQUENCE: 196
gaccaaggtc ctggaatgtc                                        20

<210> SEQ ID NO 197
<211> LENGTH: 20
<212> TYPE: DNA
<213> ORGANISM: Artificial Sequence
<220> FEATURE:
<223> OTHER INFORMATION: primer

<400> SEQUENCE: 197
gtcttccctg tacccgtagg                                        20

<210> SEQ ID NO 198
<211> LENGTH: 24
<212> TYPE: DNA
<213> ORGANISM: Artificial Sequence
<220> FEATURE:
<223> OTHER INFORMATION: primer

<400> SEQUENCE: 198
caggatgcca ttcaccttct gctg                                   24

<210> SEQ ID NO 199
<211> LENGTH: 19
<212> TYPE: DNA
<213> ORGANISM: Artificial Sequence
<220> FEATURE:
<223> OTHER INFORMATION: primer

<400> SEQUENCE: 199
cacaatggcg gctctgaag                                         19

<210> SEQ ID NO 200
<211> LENGTH: 26
<212> TYPE: DNA
<213> ORGANISM: Artificial Sequence
<220> FEATURE:
<223> OTHER INFORMATION: primer

<400> SEQUENCE: 200
acacaaacac tgtctgtacc tgaaga                                 26

<210> SEQ ID NO 201
<211> LENGTH: 23
<212> TYPE: DNA
<213> ORGANISM: Artificial Sequence
<220> FEATURE:
<223> OTHER INFORMATION: primer

<400> SEQUENCE: 201
```
aagttacgct gcgcgacagc caa 23

<210> SEQ ID NO 202
<211> LENGTH: 19
<212> TYPE: DNA
<213> ORGANISM: Artificial Sequence
<220> FEATURE:
<223> OTHER INFORMATION: primer

<400> SEQUENCE: 202
aggacgcaag gagggtttg 19

<210> SEQ ID NO 203
<211> LENGTH: 21
<212> TYPE: DNA
<213> ORGANISM: Artificial Sequence
<220> FEATURE:
<223> OTHER INFORMATION: primer

<400> SEQUENCE: 203
gatgtccgcc gagtccttac t 21

<210> SEQ ID NO 204
<211> LENGTH: 29
<212> TYPE: DNA
<213> ORGANISM: Artificial Sequence
<220> FEATURE:
<223> OTHER INFORMATION: primer

<400> SEQUENCE: 204
cagtgcctac agtctcgagt ctgccagtg 29

<210> SEQ ID NO 205
<211> LENGTH: 24
<212> TYPE: DNA
<213> ORGANISM: Artificial Sequence
<220> FEATURE:
<223> OTHER INFORMATION: primer

<400> SEQUENCE: 205
ctctgagaca gtgcttcgat gact 24

<210> SEQ ID NO 206
<211> LENGTH: 19
<212> TYPE: DNA
<213> ORGANISM: Artificial Sequence
<220> FEATURE:
<223> OTHER INFORMATION: primer

<400> SEQUENCE: 206
ccatgaggcc caacttcct 19

<210> SEQ ID NO 207
<211> LENGTH: 23
<212> TYPE: DNA
<213> ORGANISM: Artificial Sequence
<220> FEATURE:
<223> OTHER INFORMATION: primer

<400> SEQUENCE: 207
cagacttggt gccctttgac tcc 23

<210> SEQ ID NO 208
<211> LENGTH: 20
<212> TYPE: DNA
<213> ORGANISM: Artificial Sequence -continued

```
<220> FEATURE:
<223> OTHER INFORMATION: primer

<400> SEQUENCE: 208
tgccacctgg acatcatttg                                           20

<210> SEQ ID NO 209
<211> LENGTH: 21
<212> TYPE: DNA
<213> ORGANISM: Artificial Sequence
<220> FEATURE:
<223> OTHER INFORMATION: primer

<400> SEQUENCE: 209
tggacctagg gcttccaagt c                                         21

<210> SEQ ID NO 210
<211> LENGTH: 23
<212> TYPE: DNA
<213> ORGANISM: Artificial Sequence
<220> FEATURE:
<223> OTHER INFORMATION: primer

<400> SEQUENCE: 210
cactcccgag cacgttgttc cgt                                       23

<210> SEQ ID NO 211
<211> LENGTH: 20
<212> TYPE: DNA
<213> ORGANISM: Artificial Sequence
<220> FEATURE:
<223> OTHER INFORMATION: primer

<400> SEQUENCE: 211
tgtcgatgga cttccagaac                                           20

<210> SEQ ID NO 212
<211> LENGTH: 19
<212> TYPE: DNA
<213> ORGANISM: Artificial Sequence
<220> FEATURE:
<223> OTHER INFORMATION: primer

<400> SEQUENCE: 212
attgggacag cttggatca                                            19

<210> SEQ ID NO 213
<211> LENGTH: 18
<212> TYPE: DNA
<213> ORGANISM: Artificial Sequence
<220> FEATURE:
<223> OTHER INFORMATION: primer

<400> SEQUENCE: 213
cacctgggca gctgccaa                                             18

<210> SEQ ID NO 214
<211> LENGTH: 22
<212> TYPE: DNA
<213> ORGANISM: Artificial Sequence
<220> FEATURE:
<223> OTHER INFORMATION: primer

<400> SEQUENCE: 214
gagtcgggct ctggaggaaa ag                                        22
```

```
<210> SEQ ID NO 215
<211> LENGTH: 18
<212> TYPE: DNA
<213> ORGANISM: Artificial Sequence
<220> FEATURE:
<223> OTHER INFORMATION: primer

<400> SEQUENCE: 215
ccacaggctc ggacgcac                                                   18

<210> SEQ ID NO 216
<211> LENGTH: 28
<212> TYPE: DNA
<213> ORGANISM: Artificial Sequence
<220> FEATURE:
<223> OTHER INFORMATION: primer

<400> SEQUENCE: 216
agccgtgatc tgtcaccaca taattacc                                        28

<210> SEQ ID NO 217
<211> LENGTH: 23
<212> TYPE: DNA
<213> ORGANISM: Artificial Sequence
<220> FEATURE:
<223> OTHER INFORMATION: primer

<400> SEQUENCE: 217
gatctaagat ggcgactgtc gaa                                             23

<210> SEQ ID NO 218
<211> LENGTH: 25
<212> TYPE: DNA
<213> ORGANISM: Artificial Sequence
<220> FEATURE:
<223> OTHER INFORMATION: primer

<400> SEQUENCE: 218
ttagattccg ttttctcctc ttctg                                           25

<210> SEQ ID NO 219
<211> LENGTH: 27
<212> TYPE: DNA
<213> ORGANISM: Artificial Sequence
<220> FEATURE:
<223> OTHER INFORMATION: primer

<400> SEQUENCE: 219
accaccccta ctcctaatcc cccgact                                         27

<210> SEQ ID NO 220
<211> LENGTH: 23
<212> TYPE: DNA
<213> ORGANISM: Artificial Sequence
<220> FEATURE:
<223> OTHER INFORMATION: primer

<400> SEQUENCE: 220
cggttatgtc atgccagata cac                                             23

<210> SEQ ID NO 221
<211> LENGTH: 24
<212> TYPE: DNA
<213> ORGANISM: Artificial Sequence
<220> FEATURE:
<223> OTHER INFORMATION: primer

<400> SEQUENCE: 221
```

```
gaactgagac ccactgaaga aagg                                          24
```

<210> SEQ ID NO 222
<211> LENGTH: 25
<212> TYPE: DNA
<213> ORGANISM: Artificial Sequence
<220> FEATURE:
<223> OTHER INFORMATION: primer

<400> SEQUENCE: 222

```
cctcaaaggt actccctcct cccgg                                         25
```

<210> SEQ ID NO 223
<211> LENGTH: 25
<212> TYPE: DNA
<213> ORGANISM: Artificial Sequence
<220> FEATURE:
<223> OTHER INFORMATION: primer

<400> SEQUENCE: 223

```
tggctcttaa tcagtttcgt tacct                                         25
```

<210> SEQ ID NO 224
<211> LENGTH: 25
<212> TYPE: DNA
<213> ORGANISM: Artificial Sequence
<220> FEATURE:
<223> OTHER INFORMATION: primer

<400> SEQUENCE: 224

```
caaggcatat cgatcctcat aaagt                                         25
```

<210> SEQ ID NO 225
<211> LENGTH: 30
<212> TYPE: DNA
<213> ORGANISM: Artificial Sequence
<220> FEATURE:
<223> OTHER INFORMATION: primer

<400> SEQUENCE: 225

```
tgtcccacga ataatgcgta aattctccag                                    30
```

<210> SEQ ID NO 226
<211> LENGTH: 28
<212> TYPE: DNA
<213> ORGANISM: Artificial Sequence
<220> FEATURE:
<223> OTHER INFORMATION: primer

<400> SEQUENCE: 226

```
ataacaaagt gtagctctga catgaatg                                      28
```

<210> SEQ ID NO 227
<211> LENGTH: 24
<212> TYPE: DNA
<213> ORGANISM: Artificial Sequence
<220> FEATURE:
<223> OTHER INFORMATION: primer

<400> SEQUENCE: 227

```
cacacctgca gtagttttga ctca                                          24
```

<210> SEQ ID NO 228
<211> LENGTH: 30
<212> TYPE: DNA
<213> ORGANISM: Artificial Sequence

```
<220> FEATURE:
<223> OTHER INFORMATION: primer

<400> SEQUENCE: 228
ttgtttgcat ggacagtgca tctatctggt                                              30

<210> SEQ ID NO 229
<211> LENGTH: 20
<212> TYPE: DNA
<213> ORGANISM: Artificial Sequence
<220> FEATURE:
<223> OTHER INFORMATION: primer

<400> SEQUENCE: 229
acggatcaca gtggaggaag                                                         20

<210> SEQ ID NO 230
<211> LENGTH: 20
<212> TYPE: DNA
<213> ORGANISM: Artificial Sequence
<220> FEATURE:
<223> OTHER INFORMATION: primer

<400> SEQUENCE: 230
ctcatccgtc gggtcatagt                                                         20

<210> SEQ ID NO 231
<211> LENGTH: 20
<212> TYPE: DNA
<213> ORGANISM: Artificial Sequence
<220> FEATURE:
<223> OTHER INFORMATION: primer

<400> SEQUENCE: 231
cgctggctca cccctacctg                                                         20

<210> SEQ ID NO 232
<211> LENGTH: 21
<212> TYPE: DNA
<213> ORGANISM: Artificial Sequence
<220> FEATURE:
<223> OTHER INFORMATION: primer

<400> SEQUENCE: 232
ggattgctca acaaccatgc t                                                       21

<210> SEQ ID NO 233
<211> LENGTH: 24
<212> TYPE: DNA
<213> ORGANISM: Artificial Sequence
<220> FEATURE:
<223> OTHER INFORMATION: primer

<400> SEQUENCE: 233
ggcattaaca cttttggacg ataa                                                    24

<210> SEQ ID NO 234
<211> LENGTH: 30
<212> TYPE: DNA
<213> ORGANISM: Artificial Sequence
<220> FEATURE:
<223> OTHER INFORMATION: primer

<400> SEQUENCE: 234
tctggaccct cctacctctg gttcttacgt                                              30
```

```
<210> SEQ ID NO 235
<211> LENGTH: 20
<212> TYPE: DNA
<213> ORGANISM: Artificial Sequence
<220> FEATURE:
<223> OTHER INFORMATION: primer

<400> SEQUENCE: 235
ttggtacctg tgggttagca                                          20

<210> SEQ ID NO 236
<211> LENGTH: 20
<212> TYPE: DNA
<213> ORGANISM: Artificial Sequence
<220> FEATURE:
<223> OTHER INFORMATION: primer

<400> SEQUENCE: 236
cacatccaaa tgcaaactgg                                          20

<210> SEQ ID NO 237
<211> LENGTH: 26
<212> TYPE: DNA
<213> ORGANISM: Artificial Sequence
<220> FEATURE:
<223> OTHER INFORMATION: primer

<400> SEQUENCE: 237
tccccagggt agaattcaat cagagc                                   26

<210> SEQ ID NO 238
<211> LENGTH: 19
<212> TYPE: DNA
<213> ORGANISM: Artificial Sequence
<220> FEATURE:
<223> OTHER INFORMATION: primer

<400> SEQUENCE: 238
tgatgcgcct ggaaacagt                                           19

<210> SEQ ID NO 239
<211> LENGTH: 23
<212> TYPE: DNA
<213> ORGANISM: Artificial Sequence
<220> FEATURE:
<223> OTHER INFORMATION: primer

<400> SEQUENCE: 239
cgaggttgtg aaaggtgctt atc                                      23

<210> SEQ ID NO 240
<211> LENGTH: 24
<212> TYPE: DNA
<213> ORGANISM: Artificial Sequence
<220> FEATURE:
<223> OTHER INFORMATION: primer

<400> SEQUENCE: 240
agcaggcaac tccgaaggac aacg                                     24

<210> SEQ ID NO 241
<211> LENGTH: 23
<212> TYPE: DNA
<213> ORGANISM: Artificial Sequence
<220> FEATURE:
<223> OTHER INFORMATION: primer

<400> SEQUENCE: 241
```
cgaaaagatg ctgaacagtg aca                                       23

<210> SEQ ID NO 242
<211> LENGTH: 20
<212> TYPE: DNA
<213> ORGANISM: Artificial Sequence
<220> FEATURE:
<223> OTHER INFORMATION: primer

<400> SEQUENCE: 242
tcaggaacag ccaccagtga                                           20

<210> SEQ ID NO 243
<211> LENGTH: 28
<212> TYPE: DNA
<213> ORGANISM: Artificial Sequence
<220> FEATURE:
<223> OTHER INFORMATION: primer

<400> SEQUENCE: 243
cttcctcctc ccttctggtc agttggat                                  28

<210> SEQ ID NO 244
<211> LENGTH: 20
<212> TYPE: DNA
<213> ORGANISM: Artificial Sequence
<220> FEATURE:
<223> OTHER INFORMATION: primer

<400> SEQUENCE: 244
cccactcagt agccaagtca                                           20

<210> SEQ ID NO 245
<211> LENGTH: 20
<212> TYPE: DNA
<213> ORGANISM: Artificial Sequence
<220> FEATURE:
<223> OTHER INFORMATION: primer

<400> SEQUENCE: 245
cacgcaggtg gtatcagtct                                           20

<210> SEQ ID NO 246
<211> LENGTH: 27
<212> TYPE: DNA
<213> ORGANISM: Artificial Sequence
<220> FEATURE:
<223> OTHER INFORMATION: primer

<400> SEQUENCE: 246
tcaagtaaac gggctgtttt ccaaaca                                   27

<210> SEQ ID NO 247
<211> LENGTH: 20
<212> TYPE: DNA
<213> ORGANISM: Artificial Sequence
<220> FEATURE:
<223> OTHER INFORMATION: primer

<400> SEQUENCE: 247
gactccttcg tccccagttg                                           20

<210> SEQ ID NO 248
<211> LENGTH: 21
<212> TYPE: DNA
<213> ORGANISM: Artificial Sequence

```
<220> FEATURE:
<223> OTHER INFORMATION: primer

<400> SEQUENCE: 248
tggcacttga aggctctggt a                                        21

<210> SEQ ID NO 249
<211> LENGTH: 25
<212> TYPE: DNA
<213> ORGANISM: Artificial Sequence
<220> FEATURE:
<223> OTHER INFORMATION: primer

<400> SEQUENCE: 249
ttgggcctcc cataattgct ttgcc                                    25

<210> SEQ ID NO 250
<211> LENGTH: 20
<212> TYPE: DNA
<213> ORGANISM: Artificial Sequence
<220> FEATURE:
<223> OTHER INFORMATION: primer

<400> SEQUENCE: 250
cggtgtgaga agtgcagcaa                                          20

<210> SEQ ID NO 251
<211> LENGTH: 19
<212> TYPE: DNA
<213> ORGANISM: Artificial Sequence
<220> FEATURE:
<223> OTHER INFORMATION: primer

<400> SEQUENCE: 251
cctctcgcaa gtgctccat                                           19

<210> SEQ ID NO 252
<211> LENGTH: 24
<212> TYPE: DNA
<213> ORGANISM: Artificial Sequence
<220> FEATURE:
<223> OTHER INFORMATION: primer

<400> SEQUENCE: 252
ccagaccata gcacactcgg gcac                                     24

<210> SEQ ID NO 253
<211> LENGTH: 20
<212> TYPE: DNA
<213> ORGANISM: Artificial Sequence
<220> FEATURE:
<223> OTHER INFORMATION: primer

<400> SEQUENCE: 253
ccgaaatcca gatgatgatg                                          20

<210> SEQ ID NO 254
<211> LENGTH: 20
<212> TYPE: DNA
<213> ORGANISM: Artificial Sequence
<220> FEATURE:
<223> OTHER INFORMATION: primer

<400> SEQUENCE: 254
cccaaggaat gagtggattt                                          20
```

<210> SEQ ID NO 255
<211> LENGTH: 23
<212> TYPE: DNA
<213> ORGANISM: Artificial Sequence
<220> FEATURE:
<223> OTHER INFORMATION: primer

<400> SEQUENCE: 255
ctcatggacc ctggtgctac acg                                           23

<210> SEQ ID NO 256
<211> LENGTH: 19
<212> TYPE: DNA
<213> ORGANISM: Artificial Sequence
<220> FEATURE:
<223> OTHER INFORMATION: primer

<400> SEQUENCE: 256
agaaccgcaa ggtgagcaa                                                19

<210> SEQ ID NO 257
<211> LENGTH: 21
<212> TYPE: DNA
<213> ORGANISM: Artificial Sequence
<220> FEATURE:
<223> OTHER INFORMATION: primer

<400> SEQUENCE: 257
tccaactgaa ggtccctgat g                                             21

<210> SEQ ID NO 258
<211> LENGTH: 26
<212> TYPE: DNA
<213> ORGANISM: Artificial Sequence
<220> FEATURE:
<223> OTHER INFORMATION: primer

<400> SEQUENCE: 258
tggagattct ccagcacgtc atcgac                                        26

<210> SEQ ID NO 259
<211> LENGTH: 21
<212> TYPE: DNA
<213> ORGANISM: Artificial Sequence
<220> FEATURE:
<223> OTHER INFORMATION: primer

<400> SEQUENCE: 259
gcatggtagc cgaagatttc a                                             21

<210> SEQ ID NO 260
<211> LENGTH: 30
<212> TYPE: DNA
<213> ORGANISM: Artificial Sequence
<220> FEATURE:
<223> OTHER INFORMATION: primer

<400> SEQUENCE: 260
tttccggtaa tagtctgtct catagatatc                                    30

<210> SEQ ID NO 261
<211> LENGTH: 28
<212> TYPE: DNA
<213> ORGANISM: Artificial Sequence
<220> FEATURE:
<223> OTHER INFORMATION: primer

<400> SEQUENCE: 261
cgcgtcatac caaaatctcc gattttga                                               28

<210> SEQ ID NO 262
<211> LENGTH: 17
<212> TYPE: DNA
<213> ORGANISM: Artificial Sequence
<220> FEATURE:
<223> OTHER INFORMATION: primer

<400> SEQUENCE: 262
acgcaccggg tgtctga                                                            17

<210> SEQ ID NO 263
<211> LENGTH: 24
<212> TYPE: DNA
<213> ORGANISM: Artificial Sequence
<220> FEATURE:
<223> OTHER INFORMATION: primer

<400> SEQUENCE: 263
tgcccttcct tgatgatgat tatc                                                    24

<210> SEQ ID NO 264
<211> LENGTH: 24
<212> TYPE: DNA
<213> ORGANISM: Artificial Sequence
<220> FEATURE:
<223> OTHER INFORMATION: primer

<400> SEQUENCE: 264
cccaagttcc accccctcca ttca                                                    24

<210> SEQ ID NO 265
<211> LENGTH: 20
<212> TYPE: DNA
<213> ORGANISM: Artificial Sequence
<220> FEATURE:
<223> OTHER INFORMATION: primer

<400> SEQUENCE: 265
ccacagctca ccttctgtca                                                         20

<210> SEQ ID NO 266
<211> LENGTH: 20
<212> TYPE: DNA
<213> ORGANISM: Artificial Sequence
<220> FEATURE:
<223> OTHER INFORMATION: primer

<400> SEQUENCE: 266
cctcagtgcc agtctcttcc                                                         20

<210> SEQ ID NO 267
<211> LENGTH: 20
<212> TYPE: DNA
<213> ORGANISM: Artificial Sequence
<220> FEATURE:
<223> OTHER INFORMATION: primer

<400> SEQUENCE: 267
tccatcccag ctccagccag                                                         20

<210> SEQ ID NO 268
<211> LENGTH: 20
<212> TYPE: DNA
<213> ORGANISM: Artificial Sequence

```
<220> FEATURE:
<223> OTHER INFORMATION: primer

<400> SEQUENCE: 268
ccatgatcct cactctgctg                                              20

<210> SEQ ID NO 269
<211> LENGTH: 20
<212> TYPE: DNA
<213> ORGANISM: Artificial Sequence
<220> FEATURE:
<223> OTHER INFORMATION: primer

<400> SEQUENCE: 269
gaagctttgt agccggtgat                                              20

<210> SEQ ID NO 270
<211> LENGTH: 24
<212> TYPE: DNA
<213> ORGANISM: Artificial Sequence
<220> FEATURE:
<223> OTHER INFORMATION: primer

<400> SEQUENCE: 270
cactccagac ctcgcttagc atgg                                         24

<210> SEQ ID NO 271
<211> LENGTH: 19
<212> TYPE: DNA
<213> ORGANISM: Artificial Sequence
<220> FEATURE:
<223> OTHER INFORMATION: primer

<400> SEQUENCE: 271
accgggagcc ctacatgac                                               19

<210> SEQ ID NO 272
<211> LENGTH: 27
<212> TYPE: DNA
<213> ORGANISM: Artificial Sequence
<220> FEATURE:
<223> OTHER INFORMATION: primer

<400> SEQUENCE: 272
ccttaagctc tttcactgac tcaatct                                      27

<210> SEQ ID NO 273
<211> LENGTH: 28
<212> TYPE: DNA
<213> ORGANISM: Artificial Sequence
<220> FEATURE:
<223> OTHER INFORMATION: primer

<400> SEQUENCE: 273
aaatacctgc aaccgttact gccgtgac                                     28

<210> SEQ ID NO 274
<211> LENGTH: 21
<212> TYPE: DNA
<213> ORGANISM: Artificial Sequence
<220> FEATURE:
<223> OTHER INFORMATION: primer

<400> SEQUENCE: 274
cgaggattgg ttcttcagca a                                            21
```

```
<210> SEQ ID NO 275
<211> LENGTH: 22
<212> TYPE: DNA
<213> ORGANISM: Artificial Sequence
<220> FEATURE:
<223> OTHER INFORMATION: primer

<400> SEQUENCE: 275
actctgcacc agctcactgt tg                                              22

<210> SEQ ID NO 276
<211> LENGTH: 24
<212> TYPE: DNA
<213> ORGANISM: Artificial Sequence
<220> FEATURE:
<223> OTHER INFORMATION: primer

<400> SEQUENCE: 276
cacctcgcgg ttcagttcct ctgt                                            24

<210> SEQ ID NO 277
<211> LENGTH: 21
<212> TYPE: DNA
<213> ORGANISM: Artificial Sequence
<220> FEATURE:
<223> OTHER INFORMATION: primer

<400> SEQUENCE: 277
actcaagcgg aaattgaagc a                                               21

<210> SEQ ID NO 278
<211> LENGTH: 21
<212> TYPE: DNA
<213> ORGANISM: Artificial Sequence
<220> FEATURE:
<223> OTHER INFORMATION: primer

<400> SEQUENCE: 278
actccctgaa gccgagacac t                                               21

<210> SEQ ID NO 279
<211> LENGTH: 28
<212> TYPE: DNA
<213> ORGANISM: Artificial Sequence
<220> FEATURE:
<223> OTHER INFORMATION: primer

<400> SEQUENCE: 279
aggtcttatc agcacagtct ccgcctcc                                        28

<210> SEQ ID NO 280
<211> LENGTH: 19
<212> TYPE: DNA
<213> ORGANISM: Artificial Sequence
<220> FEATURE:
<223> OTHER INFORMATION: primer

<400> SEQUENCE: 280
ccgccctcac ctgaagaga                                                  19

<210> SEQ ID NO 281
<211> LENGTH: 22
<212> TYPE: DNA
<213> ORGANISM: Artificial Sequence
<220> FEATURE:
<223> OTHER INFORMATION: primer

<400> SEQUENCE: 281
```
ggaataagtt agccgcgctt ct    22

<210> SEQ ID NO 282
<211> LENGTH: 21
<212> TYPE: DNA
<213> ORGANISM: Artificial Sequence
<220> FEATURE:
<223> OTHER INFORMATION: primer

<400> SEQUENCE: 282
cccagtgtcc gccaaggagc g    21

<210> SEQ ID NO 283
<211> LENGTH: 18
<212> TYPE: DNA
<213> ORGANISM: Artificial Sequence
<220> FEATURE:
<223> OTHER INFORMATION: primer

<400> SEQUENCE: 283
tgagcgtcgc agaaacca    18

<210> SEQ ID NO 284
<211> LENGTH: 20
<212> TYPE: DNA
<213> ORGANISM: Artificial Sequence
<220> FEATURE:
<223> OTHER INFORMATION: primer

<400> SEQUENCE: 284
tccctgagcg tgagaaagct    20

<210> SEQ ID NO 285
<211> LENGTH: 20
<212> TYPE: DNA
<213> ORGANISM: Artificial Sequence
<220> FEATURE:
<223> OTHER INFORMATION: primer

<400> SEQUENCE: 285
ccagcgccgc aacgaccttc    20

<210> SEQ ID NO 286
<211> LENGTH: 19
<212> TYPE: DNA
<213> ORGANISM: Artificial Sequence
<220> FEATURE:
<223> OTHER INFORMATION: primer

<400> SEQUENCE: 286
gcggaaggtc cctcagaca    19

<210> SEQ ID NO 287
<211> LENGTH: 23
<212> TYPE: DNA
<213> ORGANISM: Artificial Sequence
<220> FEATURE:
<223> OTHER INFORMATION: primer

<400> SEQUENCE: 287
tctaagtttc ccgaggtttc tca    23

<210> SEQ ID NO 288
<211> LENGTH: 26
<212> TYPE: DNA
<213> ORGANISM: Artificial Sequence

```
<220> FEATURE:
<223> OTHER INFORMATION: primer

<400> SEQUENCE: 288
ccccgattga agaaccaga gaggct                                              26

<210> SEQ ID NO 289
<211> LENGTH: 21
<212> TYPE: DNA
<213> ORGANISM: Artificial Sequence
<220> FEATURE:
<223> OTHER INFORMATION: primer

<400> SEQUENCE: 289
cggtggacca cgaagagtta a                                                  21

<210> SEQ ID NO 290
<211> LENGTH: 19
<212> TYPE: DNA
<213> ORGANISM: Artificial Sequence
<220> FEATURE:
<223> OTHER INFORMATION: primer

<400> SEQUENCE: 290
ggctcgcctc ttccatgtc                                                     19

<210> SEQ ID NO 291
<211> LENGTH: 23
<212> TYPE: DNA
<213> ORGANISM: Artificial Sequence
<220> FEATURE:
<223> OTHER INFORMATION: primer

<400> SEQUENCE: 291
ccgggacttg gagaagcact gca                                                23

<210> SEQ ID NO 292
<211> LENGTH: 20
<212> TYPE: DNA
<213> ORGANISM: Artificial Sequence
<220> FEATURE:
<223> OTHER INFORMATION: primer

<400> SEQUENCE: 292
ctttgaaccc ttgcttgcaa                                                    20

<210> SEQ ID NO 293
<211> LENGTH: 18
<212> TYPE: DNA
<213> ORGANISM: Artificial Sequence
<220> FEATURE:
<223> OTHER INFORMATION: primer

<400> SEQUENCE: 293
cccgggacaa agcaaatg                                                      18

<210> SEQ ID NO 294
<211> LENGTH: 25
<212> TYPE: DNA
<213> ORGANISM: Artificial Sequence
<220> FEATURE:
<223> OTHER INFORMATION: primer

<400> SEQUENCE: 294
aagtcctggg tgcttctgac gcaca                                              25
```

```
<210> SEQ ID NO 295
<211> LENGTH: 19
<212> TYPE: DNA
<213> ORGANISM: Artificial Sequence
<220> FEATURE:
<223> OTHER INFORMATION: primer

<400> SEQUENCE: 295
ccgcaacgtg gttttctca                                                   19

<210> SEQ ID NO 296
<211> LENGTH: 21
<212> TYPE: DNA
<213> ORGANISM: Artificial Sequence
<220> FEATURE:
<223> OTHER INFORMATION: primer

<400> SEQUENCE: 296
tgctgggttt ctcctcctgt t                                                21

<210> SEQ ID NO 297
<211> LENGTH: 22
<212> TYPE: DNA
<213> ORGANISM: Artificial Sequence
<220> FEATURE:
<223> OTHER INFORMATION: primer

<400> SEQUENCE: 297
ctcggtgttg gccatgctcc ag                                               22

<210> SEQ ID NO 298
<211> LENGTH: 19
<212> TYPE: DNA
<213> ORGANISM: Artificial Sequence
<220> FEATURE:
<223> OTHER INFORMATION: primer

<400> SEQUENCE: 298
ttgttggtgt gccctggtg                                                   19

<210> SEQ ID NO 299
<211> LENGTH: 21
<212> TYPE: DNA
<213> ORGANISM: Artificial Sequence
<220> FEATURE:
<223> OTHER INFORMATION: primer

<400> SEQUENCE: 299
tgggttctgt ccaaacactg g                                                21

<210> SEQ ID NO 300
<211> LENGTH: 22
<212> TYPE: DNA
<213> ORGANISM: Artificial Sequence
<220> FEATURE:
<223> OTHER INFORMATION: primer

<400> SEQUENCE: 300
tggtggcggt cactccctct gc                                               22

<210> SEQ ID NO 301
<211> LENGTH: 20
<212> TYPE: DNA
<213> ORGANISM: Artificial Sequence
<220> FEATURE:
<223> OTHER INFORMATION: primer

<400> SEQUENCE: 301
```
actgaaggag acccttggag                                                    20

<210> SEQ ID NO 302
<211> LENGTH: 20
<212> TYPE: DNA
<213> ORGANISM: Artificial Sequence
<220> FEATURE:
<223> OTHER INFORMATION: primer

<400> SEQUENCE: 302
taaataaccc tgcccacaca                                                    20

<210> SEQ ID NO 303
<211> LENGTH: 21
<212> TYPE: DNA
<213> ORGANISM: Artificial Sequence
<220> FEATURE:
<223> OTHER INFORMATION: primer

<400> SEQUENCE: 303
tctcctgccg atgcccctag g                                                  21

<210> SEQ ID NO 304
<211> LENGTH: 24
<212> TYPE: DNA
<213> ORGANISM: Artificial Sequence
<220> FEATURE:
<223> OTHER INFORMATION: primer

<400> SEQUENCE: 304
agagccagtt gctgtagaac tcaa                                               24

<210> SEQ ID NO 305
<211> LENGTH: 21
<212> TYPE: DNA
<213> ORGANISM: Artificial Sequence
<220> FEATURE:
<223> OTHER INFORMATION: primer

<400> SEQUENCE: 305
ctgggcctac acagtccttc a                                                  21

<210> SEQ ID NO 306
<211> LENGTH: 27
<212> TYPE: DNA
<213> ORGANISM: Artificial Sequence
<220> FEATURE:
<223> OTHER INFORMATION: primer

<400> SEQUENCE: 306
tctctgctgg gcaaggatgt tctgttc                                            27

<210> SEQ ID NO 307
<211> LENGTH: 20
<212> TYPE: DNA
<213> ORGANISM: Artificial Sequence
<220> FEATURE:
<223> OTHER INFORMATION: primer

<400> SEQUENCE: 307
cccatggatg ctcctctgaa                                                    20

<210> SEQ ID NO 308
<211> LENGTH: 20
<212> TYPE: DNA
<213> ORGANISM: Artificial Sequence

```
<220> FEATURE:
<223> OTHER INFORMATION: primer

<400> SEQUENCE: 308
ccggtggcta ccagacattg                                               20

<210> SEQ ID NO 309
<211> LENGTH: 22
<212> TYPE: DNA
<213> ORGANISM: Artificial Sequence
<220> FEATURE:
<223> OTHER INFORMATION: primer

<400> SEQUENCE: 309
cattgactgc cgaggcccca tg                                            22

<210> SEQ ID NO 310
<211> LENGTH: 21
<212> TYPE: DNA
<213> ORGANISM: Artificial Sequence
<220> FEATURE:
<223> OTHER INFORMATION: primer

<400> SEQUENCE: 310
tgactttatg gagcccaagt t                                             21

<210> SEQ ID NO 311
<211> LENGTH: 20
<212> TYPE: DNA
<213> ORGANISM: Artificial Sequence
<220> FEATURE:
<223> OTHER INFORMATION: primer

<400> SEQUENCE: 311
gccaagtcgc tgtcatctaa                                               20

<210> SEQ ID NO 312
<211> LENGTH: 25
<212> TYPE: DNA
<213> ORGANISM: Artificial Sequence
<220> FEATURE:
<223> OTHER INFORMATION: primer

<400> SEQUENCE: 312
ttccagtgca ttgaacttca cagca                                         25

<210> SEQ ID NO 313
<211> LENGTH: 23
<212> TYPE: DNA
<213> ORGANISM: Artificial Sequence
<220> FEATURE:
<223> OTHER INFORMATION: primer

<400> SEQUENCE: 313
cgcttgccta actcatactt tcc                                           23

<210> SEQ ID NO 314
<211> LENGTH: 20
<212> TYPE: DNA
<213> ORGANISM: Artificial Sequence
<220> FEATURE:
<223> OTHER INFORMATION: primer

<400> SEQUENCE: 314
ccattcagac tgcgccactt                                               20
```

```
<210> SEQ ID NO 315
<211> LENGTH: 19
<212> TYPE: DNA
<213> ORGANISM: Artificial Sequence
<220> FEATURE:
<223> OTHER INFORMATION: primer

<400> SEQUENCE: 315
tccacgcagc gtggcactg                                                   19

<210> SEQ ID NO 316
<211> LENGTH: 20
<212> TYPE: DNA
<213> ORGANISM: Artificial Sequence
<220> FEATURE:
<223> OTHER INFORMATION: primer

<400> SEQUENCE: 316
tccttcagct ttcacactgg                                                  20

<210> SEQ ID NO 317
<211> LENGTH: 20
<212> TYPE: DNA
<213> ORGANISM: Artificial Sequence
<220> FEATURE:
<223> OTHER INFORMATION: primer

<400> SEQUENCE: 317
aaatcctgtt cccacctgac                                                  20

<210> SEQ ID NO 318
<211> LENGTH: 29
<212> TYPE: DNA
<213> ORGANISM: Artificial Sequence
<220> FEATURE:
<223> OTHER INFORMATION: primer

<400> SEQUENCE: 318
tccagaagag tcatgcaact tcatttctg                                        29

<210> SEQ ID NO 319
<211> LENGTH: 20
<212> TYPE: DNA
<213> ORGANISM: Artificial Sequence
<220> FEATURE:
<223> OTHER INFORMATION: primer

<400> SEQUENCE: 319
agtgggagac acctgacctt                                                  20

<210> SEQ ID NO 320
<211> LENGTH: 20
<212> TYPE: DNA
<213> ORGANISM: Artificial Sequence
<220> FEATURE:
<223> OTHER INFORMATION: primer

<400> SEQUENCE: 320
tgatctgggc attgtactcc                                                  20

<210> SEQ ID NO 321
<211> LENGTH: 29
<212> TYPE: DNA
<213> ORGANISM: Artificial Sequence
<220> FEATURE:
<223> OTHER INFORMATION: primer

<400> SEQUENCE: 321
```
ttgatcttct gctcaatctc agcttgaga 29

<210> SEQ ID NO 322
<211> LENGTH: 20
<212> TYPE: DNA
<213> ORGANISM: Artificial Sequence
<220> FEATURE:
<223> OTHER INFORMATION: primer

<400> SEQUENCE: 322
cgaagccctt acaagtttcc 20

<210> SEQ ID NO 323
<211> LENGTH: 20
<212> TYPE: DNA
<213> ORGANISM: Artificial Sequence
<220> FEATURE:
<223> OTHER INFORMATION: primer

<400> SEQUENCE: 323
ggactcttca ggggtgaaat 20

<210> SEQ ID NO 324
<211> LENGTH: 24
<212> TYPE: DNA
<213> ORGANISM: Artificial Sequence
<220> FEATURE:
<223> OTHER INFORMATION: primer

<400> SEQUENCE: 324
cccttacgga ttcctggagg gaac 24

<210> SEQ ID NO 325
<211> LENGTH: 20
<212> TYPE: DNA
<213> ORGANISM: Artificial Sequence
<220> FEATURE:
<223> OTHER INFORMATION: primer

<400> SEQUENCE: 325
ccagacgagc gattagaagc 20

<210> SEQ ID NO 326
<211> LENGTH: 20
<212> TYPE: DNA
<213> ORGANISM: Artificial Sequence
<220> FEATURE:
<223> OTHER INFORMATION: primer

<400> SEQUENCE: 326
tcctcctctt cctcctcctc 20

<210> SEQ ID NO 327
<211> LENGTH: 23
<212> TYPE: DNA
<213> ORGANISM: Artificial Sequence
<220> FEATURE:
<223> OTHER INFORMATION: primer

<400> SEQUENCE: 327
tgtgaggtga atgatttggg gga 23

<210> SEQ ID NO 328
<211> LENGTH: 24
<212> TYPE: DNA
<213> ORGANISM: Artificial Sequence

```
<220> FEATURE:
<223> OTHER INFORMATION: primer

<400> SEQUENCE: 328
ccattctatc atcaacgggt acaa                                          24

<210> SEQ ID NO 329
<211> LENGTH: 23
<212> TYPE: DNA
<213> ORGANISM: Artificial Sequence
<220> FEATURE:
<223> OTHER INFORMATION: primer

<400> SEQUENCE: 329
tcagcaagtg ggaaggtgta atc                                           23

<210> SEQ ID NO 330
<211> LENGTH: 25
<212> TYPE: DNA
<213> ORGANISM: Artificial Sequence
<220> FEATURE:
<223> OTHER INFORMATION: primer

<400> SEQUENCE: 330
tctccacaga caaggccagg actcg                                         25

<210> SEQ ID NO 331
<211> LENGTH: 20
<212> TYPE: DNA
<213> ORGANISM: Artificial Sequence
<220> FEATURE:
<223> OTHER INFORMATION: primer

<400> SEQUENCE: 331
tgtggcaagt gcaaatgtaa                                               20

<210> SEQ ID NO 332
<211> LENGTH: 20
<212> TYPE: DNA
<213> ORGANISM: Artificial Sequence
<220> FEATURE:
<223> OTHER INFORMATION: primer

<400> SEQUENCE: 332
gtcgcagatc cagtctgatg                                               20

<210> SEQ ID NO 333
<211> LENGTH: 24
<212> TYPE: DNA
<213> ORGANISM: Artificial Sequence
<220> FEATURE:
<223> OTHER INFORMATION: primer

<400> SEQUENCE: 333
cagaggcctt gggtaggtgc actc                                          24

<210> SEQ ID NO 334
<211> LENGTH: 40
<212> TYPE: DNA
<213> ORGANISM: Artificial Sequence
<220> FEATURE:
<223> OTHER INFORMATION: primer

<400> SEQUENCE: 334
cctgaacatg aaggagctga cctgaacatg aaggagctga                         40
```

```
<210> SEQ ID NO 335
<211> LENGTH: 19
<212> TYPE: DNA
<213> ORGANISM: Artificial Sequence
<220> FEATURE:
<223> OTHER INFORMATION: primer

<400> SEQUENCE: 335
catcacgtct ccgaactcc                                               19

<210> SEQ ID NO 336
<211> LENGTH: 21
<212> TYPE: DNA
<213> ORGANISM: Artificial Sequence
<220> FEATURE:
<223> OTHER INFORMATION: primer

<400> SEQUENCE: 336
tcccgatggt ctgcagcagc t                                            21

<210> SEQ ID NO 337
<211> LENGTH: 20
<212> TYPE: DNA
<213> ORGANISM: Artificial Sequence
<220> FEATURE:
<223> OTHER INFORMATION: primer

<400> SEQUENCE: 337
catcttccag gaggaccact                                              20

<210> SEQ ID NO 338
<211> LENGTH: 20
<212> TYPE: DNA
<213> ORGANISM: Artificial Sequence
<220> FEATURE:
<223> OTHER INFORMATION: primer

<400> SEQUENCE: 338
tccgaccttc aatcatttca                                              20

<210> SEQ ID NO 339
<211> LENGTH: 24
<212> TYPE: DNA
<213> ORGANISM: Artificial Sequence
<220> FEATURE:
<223> OTHER INFORMATION: primer

<400> SEQUENCE: 339
ctctgtggca ccctggacta cctg                                         24

<210> SEQ ID NO 340
<211> LENGTH: 20
<212> TYPE: DNA
<213> ORGANISM: Artificial Sequence
<220> FEATURE:
<223> OTHER INFORMATION: primer

<400> SEQUENCE: 340
tgttttgatt cccgggctta                                              20

<210> SEQ ID NO 341
<211> LENGTH: 24
<212> TYPE: DNA
<213> ORGANISM: Artificial Sequence
<220> FEATURE:
<223> OTHER INFORMATION: primer

<400> SEQUENCE: 341
```
caaagctgtc agctctagca aaag 24

<210> SEQ ID NO 342
<211> LENGTH: 28
<212> TYPE: DNA
<213> ORGANISM: Artificial Sequence
<220> FEATURE:
<223> OTHER INFORMATION: primer

<400> SEQUENCE: 342
tgccttcttc ctccctcact tctcacct 28

<210> SEQ ID NO 343
<211> LENGTH: 19
<212> TYPE: DNA
<213> ORGANISM: Artificial Sequence
<220> FEATURE:
<223> OTHER INFORMATION: primer

<400> SEQUENCE: 343
aagaggaacg gagcgagtc 19

<210> SEQ ID NO 344
<211> LENGTH: 19
<212> TYPE: DNA
<213> ORGANISM: Artificial Sequence
<220> FEATURE:
<223> OTHER INFORMATION: primer

<400> SEQUENCE: 344
atgtgtgagc cgagtcctg 19

<210> SEQ ID NO 345
<211> LENGTH: 23
<212> TYPE: DNA
<213> ORGANISM: Artificial Sequence
<220> FEATURE:
<223> OTHER INFORMATION: primer

<400> SEQUENCE: 345
cacgtcccac agctcaggga atc 23

<210> SEQ ID NO 346
<211> LENGTH: 20
<212> TYPE: DNA
<213> ORGANISM: Artificial Sequence
<220> FEATURE:
<223> OTHER INFORMATION: primer

<400> SEQUENCE: 346
gccaactgct ttcatttgtg 20

<210> SEQ ID NO 347
<211> LENGTH: 20
<212> TYPE: DNA
<213> ORGANISM: Artificial Sequence
<220> FEATURE:
<223> OTHER INFORMATION: primer

<400> SEQUENCE: 347
actcaggccc atttcccttta 20

<210> SEQ ID NO 348
<211> LENGTH: 28
<212> TYPE: DNA
<213> ORGANISM: Artificial Sequence

```
<220> FEATURE:
<223> OTHER INFORMATION: primer

<400> SEQUENCE: 348
agggatctga accaatacag agcagaca                                          28

<210> SEQ ID NO 349
<211> LENGTH: 20
<212> TYPE: DNA
<213> ORGANISM: Artificial Sequence
<220> FEATURE:
<223> OTHER INFORMATION: primer

<400> SEQUENCE: 349
aacaccaatg ggttccatct                                                   20

<210> SEQ ID NO 350
<211> LENGTH: 20
<212> TYPE: DNA
<213> ORGANISM: Artificial Sequence
<220> FEATURE:
<223> OTHER INFORMATION: primer

<400> SEQUENCE: 350
cctcttcatc aggccaaact                                                   20

<210> SEQ ID NO 351
<211> LENGTH: 24
<212> TYPE: DNA
<213> ORGANISM: Artificial Sequence
<220> FEATURE:
<223> OTHER INFORMATION: primer

<400> SEQUENCE: 351
ttctgggctc ctgattgctc aagc                                              24

<210> SEQ ID NO 352
<211> LENGTH: 22
<212> TYPE: DNA
<213> ORGANISM: Artificial Sequence
<220> FEATURE:
<223> OTHER INFORMATION: primer

<400> SEQUENCE: 352
tcaccctctg tgacttcatc gt                                                22

<210> SEQ ID NO 353
<211> LENGTH: 22
<212> TYPE: DNA
<213> ORGANISM: Artificial Sequence
<220> FEATURE:
<223> OTHER INFORMATION: primer

<400> SEQUENCE: 353
tgtggttcag gctcttcttc tg                                                22

<210> SEQ ID NO 354
<211> LENGTH: 22
<212> TYPE: DNA
<213> ORGANISM: Artificial Sequence
<220> FEATURE:
<223> OTHER INFORMATION: primer

<400> SEQUENCE: 354
ccctgggaca ccctgagcac ca                                                22
```

```
<210> SEQ ID NO 355
<211> LENGTH: 22
<212> TYPE: DNA
<213> ORGANISM: Artificial Sequence
<220> FEATURE:
<223> OTHER INFORMATION: primer

<400> SEQUENCE: 355
cgactccgtt ctcagtgtct ga                                              22

<210> SEQ ID NO 356
<211> LENGTH: 19
<212> TYPE: DNA
<213> ORGANISM: Artificial Sequence
<220> FEATURE:
<223> OTHER INFORMATION: primer

<400> SEQUENCE: 356
ccctccatgc ccactttct                                                  19

<210> SEQ ID NO 357
<211> LENGTH: 24
<212> TYPE: DNA
<213> ORGANISM: Artificial Sequence
<220> FEATURE:
<223> OTHER INFORMATION: primer

<400> SEQUENCE: 357
atcttgagtc ccctggagga aagc                                            24

<210> SEQ ID NO 358
<211> LENGTH: 20
<212> TYPE: DNA
<213> ORGANISM: Artificial Sequence
<220> FEATURE:
<223> OTHER INFORMATION: primer

<400> SEQUENCE: 358
tgctgttgct gagtctgttg                                                 20

<210> SEQ ID NO 359
<211> LENGTH: 20
<212> TYPE: DNA
<213> ORGANISM: Artificial Sequence
<220> FEATURE:
<223> OTHER INFORMATION: primer

<400> SEQUENCE: 359
cttgcctggc ttcacagata                                                 20

<210> SEQ ID NO 360
<211> LENGTH: 24
<212> TYPE: DNA
<213> ORGANISM: Artificial Sequence
<220> FEATURE:
<223> OTHER INFORMATION: primer

<400> SEQUENCE: 360
ccagtcccca gaagaccatg tctg                                            24

<210> SEQ ID NO 361
<211> LENGTH: 19
<212> TYPE: DNA
<213> ORGANISM: Artificial Sequence
<220> FEATURE:
<223> OTHER INFORMATION: primer

<400> SEQUENCE: 361
```
gtggatgtgc cctgaagga 19

<210> SEQ ID NO 362
<211> LENGTH: 20
<212> TYPE: DNA
<213> ORGANISM: Artificial Sequence
<220> FEATURE:
<223> OTHER INFORMATION: primer

<400> SEQUENCE: 362
ctgcggatcc agggtaagaa 20

<210> SEQ ID NO 363
<211> LENGTH: 28
<212> TYPE: DNA
<213> ORGANISM: Artificial Sequence
<220> FEATURE:
<223> OTHER INFORMATION: primer

<400> SEQUENCE: 363
aagccaggcg tctacacgag agtctcac 28

<210> SEQ ID NO 364
<211> LENGTH: 25
<212> TYPE: DNA
<213> ORGANISM: Artificial Sequence
<220> FEATURE:
<223> OTHER INFORMATION: primer

<400> SEQUENCE: 364
cctcagcaag acgttatttg aaatt 25

<210> SEQ ID NO 365
<211> LENGTH: 24
<212> TYPE: DNA
<213> ORGANISM: Artificial Sequence
<220> FEATURE:
<223> OTHER INFORMATION: primer

<400> SEQUENCE: 365
aagtgtgatt ggcaaaactg attg 24

<210> SEQ ID NO 366
<211> LENGTH: 26
<212> TYPE: DNA
<213> ORGANISM: Artificial Sequence
<220> FEATURE:
<223> OTHER INFORMATION: primer

<400> SEQUENCE: 366
cctctctctc aaggccccaa accagt 26

<210> SEQ ID NO 367
<211> LENGTH: 23
<212> TYPE: DNA
<213> ORGANISM: Artificial Sequence
<220> FEATURE:
<223> OTHER INFORMATION: primer

<400> SEQUENCE: 367
gcagttggaa gacacaggaa agt 23

<210> SEQ ID NO 368
<211> LENGTH: 21
<212> TYPE: DNA
<213> ORGANISM: Artificial Sequence

```
<220> FEATURE:
<223> OTHER INFORMATION: primer

<400> SEQUENCE: 368
tgcgtggcac tattttcaag a                                              21

<210> SEQ ID NO 369
<211> LENGTH: 27
<212> TYPE: DNA
<213> ORGANISM: Artificial Sequence
<220> FEATURE:
<223> OTHER INFORMATION: primer

<400> SEQUENCE: 369
tccccaaatt gcagatttat caacggc                                        27

<210> SEQ ID NO 370
<211> LENGTH: 25
<212> TYPE: DNA
<213> ORGANISM: Artificial Sequence
<220> FEATURE:
<223> OTHER INFORMATION: primer

<400> SEQUENCE: 370
agactgtgga gtttgatgtt gttga                                          25

<210> SEQ ID NO 371
<211> LENGTH: 22
<212> TYPE: DNA
<213> ORGANISM: Artificial Sequence
<220> FEATURE:
<223> OTHER INFORMATION: primer

<400> SEQUENCE: 371
ggaacaccac caggacctgt aa                                             22

<210> SEQ ID NO 372
<211> LENGTH: 23
<212> TYPE: DNA
<213> ORGANISM: Artificial Sequence
<220> FEATURE:
<223> OTHER INFORMATION: primer

<400> SEQUENCE: 372
ttgctgcctc cgcacccttt tct                                            23
```

GENE EXPRESSION PROFILING OF EGFR POSITIVE CANCER

This application claims priority under 35 U.S.C. §119(e) to provisional application Ser. No. 60/427,090 filed on Nov. 15, 2002, the entire disclosure of which is hereby expressly incorporated by reference.

BACKGROUND OF THE INVENTION

1. Field of the Invention

The present invention concerns gene expression profiling of tissue samples obtained from EGFR-positive cancer. More specifically, the invention provides diagnostic, prognostic and predictive methods based on the molecular characterization of gene expression in paraffin-embedded, fixed tissue samples of EGFR-expressing cancer, which allow a physician to predict whether a patient is likely to respond well to treatment with an EGFR inhibitor. In addition, the present invention provides treatment methods based on such findings.

2. Description of the Related Art

Oncologists have a number of treatment options available to them, including different combinations of chemotherapeutic drugs that are characterized as "standard of care," and a number of drugs that do not carry a label claim for particular cancer, but for which there is evidence of efficacy in that cancer. Best likelihood of good treatment outcome requires that patients be assigned to optimal available cancer treatment, and that this assignment be made as quickly as possible following diagnosis.

Currently, diagnostic tests used in clinical practice are single analyte, and therefore do not capture the potential value of knowing relationships between dozens of different markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes (DNA or RNA) from small amounts of material. Thus, traditionally fixed tissue has been rarely used other than for immunohistochemistry detection of proteins.

Recently, several groups have published studies concerning the classification of various cancer types by microarray gene expression analysis (see, e.g. Golub et al., *Science* 286: 531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al., *Proc. Natl. Acad. Sci. USA* 98:15149-15154 (2001)). Certain classifications of human breast cancers based on gene expression patterns have also been reported (Martin et al., *Cancer Res.* 60:2232-2238 (2000); West et al., *Proc. Natl. Acad. Sci. USA* 98:11462-11467 (2001); Sorlie et al., *Proc. Natl. Acad. Sci. USA* 98:10869-10874 (2001); Yan et al., *Cancer Res.* 61:8375-8380 (2001)). However, these studies mostly focus on improving and refining the already established classification of various types of cancer, including breast cancer, and generally do not link the findings to treatment strategies in order to improve the clinical outcome of cancer therapy.

Although modern molecular biology and biochemistry have revealed more than 100 genes whose activities influence the behavior of tumor cells, state of their differentiation, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients to treatment with anti-estrogen drugs, such as tamoxifen. Another exceptional example is the use of ErbB2 (Her2) protein expression in breast carcinomas to select patients with the Her2 antagonist drug Herceptin® (Genentech, Inc., South San Francisco, Calif.).

Despite recent advances, the challenge of cancer treatment remains to target specific treatment regimens to pathogenically distinct tumor types, and ultimately personalize tumor treatment in order to optimize outcome. Hence, a need exists for tests that simultaneously provide predictive information about patient responses to the variety of treatment options.

SUMMARY OF THE INVENTION

The present invention is based on findings of Phase II clinical studies of gene expression in tissue samples obtained from EGFR-expressing head and neck cancer or colon cancer of human patients who responded well or did not respond to (showed resistance to) treatment with EGFR inhibitors.

Based upon such findings, in one-aspect the present invention concerns a method for predicting the likelihood that a patient diagnosed with an EGFR-expressing cancer will respond to treatment with an EGFR inhibitor, comprising determining the expression level of one or more prognostic RNA transcripts or their products in a sample comprising EGFR-expressing cancer cells-obtained from the patient, wherein the prognostic transcript is the transcript of one or more genes selected from the group consisting of: Bak; Bclx; BRAF; BRK; Cad17; CCND3; CD105; CD44s; CD82; CD9; CGA; CTSL; EGFRd27; ErbB3; EREG; GPC3; GUS; HGF; ID1; IGFBP3; ITGB3; ITGB3; p27; P53; PTPD1; RB1; RPLPO; STK15; SURV; TERC; TGFBR2; TIMP2; TITF1; XIAP; YB-1; A-Catenin; AKT1; AKT2; APC; Bax; B-Catenin; BTC; CA9; CCNA2; CCNE1; CCNE2; CD134; CD44E; CD44v3; CD44v6; CD68; CDC25B; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; P14ARF; PAI1; PDGFA; PDGFB; PGK1; PLAUR; PPARG; RANBP2; RASSF1; RIZ1; SPRY2; Src; TFRC; TP53BP1; UPA; and VEGFC, wherein (a) the patient is unlikely to benefit from treatment with an EGFR inhibitor if the normalized levels of any of the following genes A-Catenin; AKT1; AKT2; APC; Bax; B-Catenin; BTC; CA9; CCNA2; CCNE1; CCNE2; CD134; CD44E; CD44v3; CD44v6; CD68; CDC25B; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1, ITGA3; KRT17; LAMC2; MTA1; NMYC; P14ARF; PAI1; PDGFA; PDGFB; PGK1; PLAUR; PPARG; RANBP2; RASSF1; RIZ1; SPRY2; Src; TFRC; TP53BP1; upa; VEGFC, or their products are elevated above defined expression thresholds, and (b) the patient is likely to benefit from treatment with an EGFR inhibitor if the normalized levels of any of the following genes Bak; Bclx; BRAF; BRK; Cad17; CCND3; CD105; CD44s; CD82; CD9; CGA; CTSL; EGFRd27; ErbB3; EREG; GPC3; GUS; HGF; ID1; IGFBP3; ITGB3; ITGB3; p27; P53; PTPD1; RB1; RPLPO; STK15; SURV; TERC; TGFBR2; TIMP2; TITF1; XIAP; and YB-1, or their products are elevated above defined expression thresholds.

In another aspect, the present invention concerns a prognostic method comprising
  (a) subjecting a sample comprising EGFR-expressing cancer cells obtained from a patient to quantitative analysis of the expression level of at least one gene selected from the group consisting of CD44v3; CD44v6; DR5; GRO1; KRT17; and LAMC2 gene or their products, and
  (b) identifying the patient as likely to show resistance to treatment with an EGFR-inhibitor if the expression levels of such gene or genes, or their products, are elevated above a defined threshold. In a particular embodiment, the gene is LAMC2.

In yet another aspect, the invention concerns a method for predicting the likelihood that a patient diagnosed with an EGFR-expressing head or neck cancer will respond to treatment with an EGFR inhibitor, comprising determining the expression level of one or more prognostic RNA transcripts or their products in a sample comprising EGFR-expressing cancer cells obtained from such patient, wherein the prognostic transcript is the transcript of one or more genes selected from the group consisting of: CD44s; CD82; CGA; CTSL; EGFRd27; IGFBP3; p27; P53; RB1; TIMP2; YB-1; A-Catenin; AKT1; AKT2; APC; Bax; B-Catenin; BTC; CCNA2; CCNE1; CCNE2; CD105; CD44v3; CD44v6; CD68; CEACAM6; Chk2; cMet; COX2; cripto; DCR3; DLKBLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; PAI1; PDGFA; PGK1; PTPD1; RANBP2; SPRY2; TP53BP1; and VEGFC, wherein (a) normalized expression of one or more of A-Catenin; AKT1; AKT2; APC; Bax; B-Catenin; BTC; CCNA2; CCNE1; CCNE2; CD105; CD44v3; CD44v6; CD68; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; PAI1; PDGFA; PGK1; PTPD1; RANBP2; SPRY2; TP53BP1; VEGFC, or the corresponding gene product, above determined expression thresholds indicates that the patient is likely to show resistance to treatment with an EGFR inhibitor, and (b) normalized expression of one or more of CD44s; CD82; CGA; CTSL; EGFRd27; IGFBP3; p27; P53; RB1; TIMP2; YB-1, or the corresponding gene product, above defined expression thresholds indicates that the patient is likely to respond well to treatment with an EGFR inhibitor.

In a further aspect, the invention concerns a method for predicting the likelihood that a patient diagnosed with an EGFR-expressing colon cancer will respond to treatment with an EGFR inhibitor, comprising determining the expression level of one or more prognostic RNA transcripts or their products in a sample comprising EGFR-expressing cancer cells obtained from the patient, wherein the prognostic transcript is the transcript of one or more genes selected from the group consisting of Bak; Bclx; BRAF; BRK; Cad17; CCND3; CCNE1; CCNE2; CD105; CD9; COX2; DIABLO; ErbB3; EREG; FRP1; GPC3; GUS; HER2; HGF; ID1; ITGB3; PTPD1; RPLPO; STK15; SURV; TERC; TGFBR2; TITF1; XIAP; CA9; CD134; CD44E; CD44v3; CD44v6; CDC25B; CGA; DR5; GRO1; KRT17; LAMC2; P14ARF; PDGFB; PLAUR; PPARG; RASSF1; RIZ1; Src; TFRC; and UPA, wherein (a) elevated expression of one or more of CA9; CD134; CD44E; CD44v3; CD44v6; CDC25B; CGA; DR5; GRO1; KRT17; LAMC2; P14ARF; PDGFB; PLAUR; PPARG; RASSF1; RIZ1; Src; TFRC; and UPA, or the corresponding gene product, above defined expression thresholds indicates that the patient is likely to show resistance to treatment with an EGFR inhibitor, and normalized expression of one or more of Bak; Bclx; BRAF; BRK; Cad17; CCND3; CCNE1; CCNE2; CD105; CD9; COX2; DIABLO; ErbB3; EREG; FRP1; GPC3; GUS; HER2; HGF; ID1; ITGB3; PTPD1; RPLPO; STK15; SURV; TERC; TGFBR2; TITF1; XIAP, or the corresponding gene product, above certain expression thresholds indicates that the patient is likely to respond well to treatment with an EGFR inhibitor.

In another aspect, the invention concerns a method comprising treating a patient diagnosed with an EGFR-expressing cancer and determined to have elevated normalized levels of one or more of the RNA transcripts of Bak; Bclx; BRAF; BRK; Cad17; CCND3; CD105; CD44s; CD82; CD9; CGA; CTSL; EGFRd27; ErbB3; EREG; GPC3; GUS; HGF; ID1; IGFBP3; ITGB3; ITGB3; p27; P53; PTPD1; RB1; RPLPO; STK15; SURV; TERC; TGFBR2; TIMP2; TITF1; XIAP; YB-1; A-Catenin; AKT1; AKT2; APC; Bax; B-Catenin; BTC; CA9; CCNA2; CCNE1; CCNE2; CD134; CD44E; CD44v3; CD44v6; CD68; CDC25B; CEACAM6; Chk2; cMet; COX2; cripto; DCR3; DLKBLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; P14ARF; PAI1; PDGFA; PDGFB; PGK1; PLAUR; PPARG; RANBP2; RASSF1; RIZ1; SPRY2; Src; TFRC; TP53BP1; UPA; and VEGFC genes, or the corresponding gene products in the cancer, with an effective amount of an EGFR-inhibitor, wherein elevated RNA transcript level is defined by a defined expression threshold.

In yet another aspect, the invention concerns a method comprising treating a patient diagnosed with an EGFR-expressing head or neck cancer and determined to have elevated normalized expression of one or more of the RNA transcripts of CD44s; CD82; CGA; CTSL; EGFRd27; IGFBP3; p27; P53; RB1; TIMP2; YB-1; A-Catenin; AKT1; AKT2; APC; Bax; B-Catenin; BTC; CCNA2; CCNE1; CCNE2; CD105; CD44v3; CD44v6; CD68; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; PAI1; PDGFA; PGK1; PTPD1; RANBP2; SPRY2; TP53BP1; VEGFC genes, or the corresponding gene products in said cancer, with an effective amount of an EGFR-inhibitor, wherein elevated normalized RNA transcript level is defined by a defined expression threshold.

In a further aspect, the invention concerns a method comprising treating a patient diagnosed with an EGFR-expressing colon cancer and determined to have elevated normalized expression of one or more of the RNA transcripts of Bak; Bclx; BRAF; BRK; Cad17; CCND3; CCNE1; CCNE2; CD105; CD9; COX2; DLKBLO; ErbB3; EREG; FRP1; GPC3; GUS; HER2; HGF; ID1; ITGB3; PTPD1; RPLPO; STK15; SURV; TERC; TGFBR2; TITF1; XIAP; CA9; CD134; CD44E; CD44v3; CD44v6; CDC25B; CGA; DR5; GRO1; KRT17; LAMC2; P14ARF; PDGFB; PLAUR; PPARG; RASSF1; RIZ1; Src; TFRC; UPA genes, or the corresponding gene products in such cancer, with an effective amount of an EGFR-inhibitor, wherein elevated normalized RNA transcript level is defined by a defined expression threshold.

The invention further concerns an array comprising (a) polynucleotides hybridizing to the following genes: Bak; Bclx; BRAF; BRK; Cad17; CCND3; CD105; CD44s; CD82; CD9; CGA; CTSL; EGFRd27; ErbB3; EREG; GPC3; GUS; HGF; ID1; IGFBP3; ITGB3; ITGB3; p27; P53; PTPD1; RB1; RPLPO; STK15; SURV; TERC; TGFBR2; TIMP2; TITF1; XIAP; YB-1; A-Catenin; AKT1; AKT2; APC; Bax; B-Catenin; BTC; CA9; CCNA2; CCNE1; CCNE2; CD134; CD44E; CD44v3; CD44v6; CD68; CDC25B; CEACAM6;

Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; P14ARF; PAI1; PDGFA; PDGFB; PGK1; PLAUR; PPARG; RANBP2; RASSF1; RIZ1; SPRY2; Src; TFRC; TP53BP1; UPA; VEGFC; or (b) an array comprising polynucleotides hybridizing to the following genes: CD44v3; CD44v6; DR5; GRO1; KRT17; and LAMC2, immobilized on a solid surface; or (c) an array comprising polynucleotides hybridizing to the following genes: CD44s; CD82; CGA; CTSL; EGFRd27; IGFBP3; p27; P53; RB1; TIMP2; YB-1; A-Catenin; AKT1; AKT2; APC; Bax; B-Catenin; BTC; CCNA2; CCNE1; CCNE2; CD105; CD44v3; CD44v6; CD68; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; PAI1; PDGFA; PGK1; PTPD1; RANBP2; SPRY2; TP53BP1; and VEGFC, immobilized on a solid surface, or (d) an array comprising polynucleotides hybridizing to the following genes: Bak; Bclx; BRAF; BRK; Cad17; CCND3; CCNE1; CCNE2; CD105; CD9; COX2; DIABLO; ErbB3; EREG; FRP1; GPC3; GUS; HER2; HGF; ID1; ITGB3; PTPD1; RPLPO; STK15; SURV; TERC; TGFBR2; TITF1; XIAP; CA9; CD134; CD44E; CD44v3; CD44v6; CDC25B; CGA; DR5; GRO1; KRT17; LAMC2; P14ARF; PDGFB; PLAUR; PPARG; RASSF1; RIZ1; Src; TFRC; and UPA, immobilized on a solid surface.

In a further aspect, the invention concerns a method in which RNA is isolated from a fixed, paraffin-embedded tissue specimen by a procedure comprising:

(a) incubating a section of the fixed, paraffin-embedded tissue specimen at a temperature of about 56° C. to 70° C. in a lysis buffer, in the presence of a protease, without prior dewaxing, to form a lysis solution;

(b) cooling the lysis solution to a temperature where the wax solidifies; and (c) isolating the nucleic acid from the lysis solution.

In a different aspect, the invention concerns a kit comprising one or more of (1) extraction buffer/reagents and protocol; (2) reverse transcription buffer/reagents and protocol; and (3) qPCR buffer/reagents and protocol suitable for performing the gene expression analysis methods of the invention.

In a further aspect, the invention concerns a method for measuring levels of mRNA products of genes listed in Tables 5A and 5B by quantitative RT-PCR (qRT-PCR) reaction, by using an amplicon listed in Tables 5A and 5B and a corresponding primer-probe set listed in Tables 6A-6F.

DETAILED DESCRIPTION OF THE PREFERRED EMBODIMENT

A. Definitions

Figure 1:
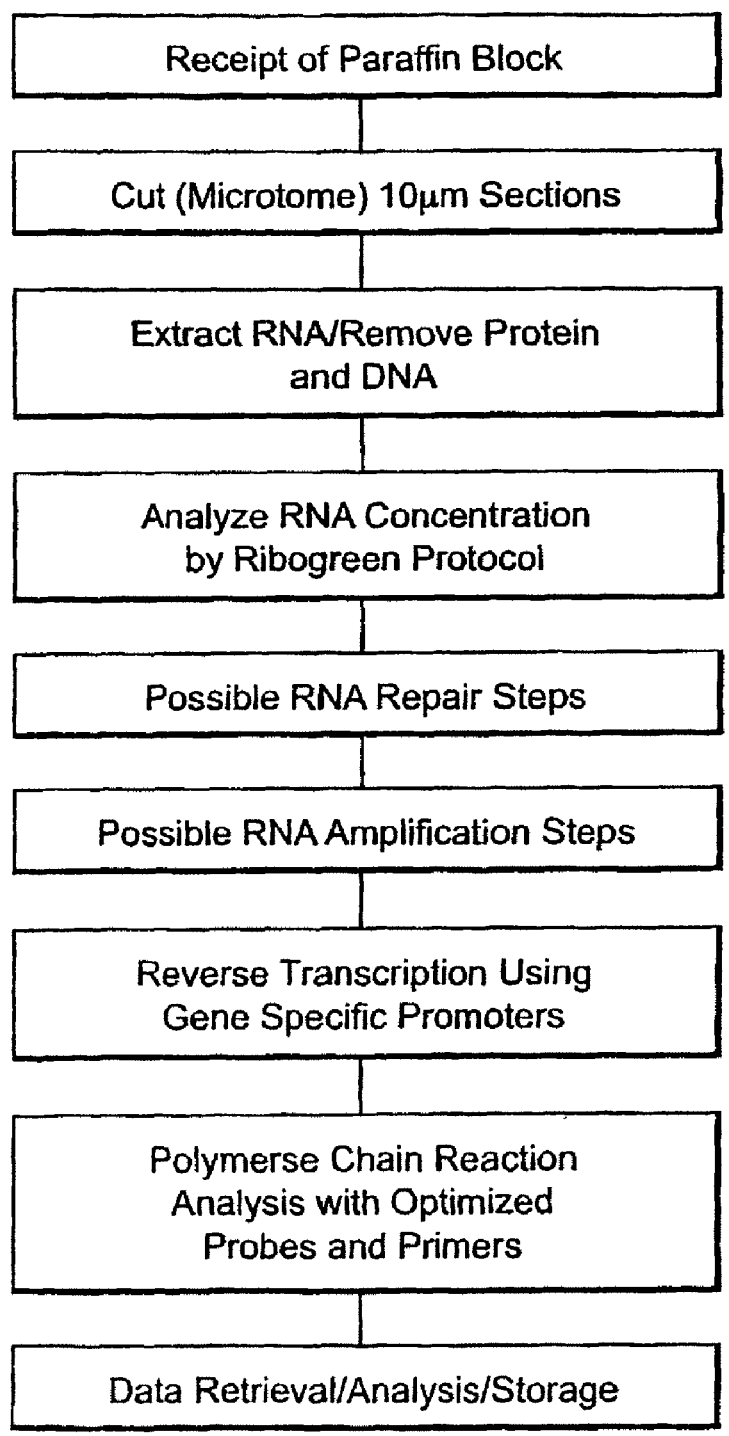
FIG. 1 is a chart illustrating the overall workflow of the process of the invention for measurement of gene expression. In the Figure, FPET stands for "fixed paraffin-embedded tissue," and "RT-PCR" stands for "reverse transcriptase PCR." RNA concentration is determined by using the commercial RiboGreen™ RNA Quantitation Reagent and Protocol.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The term "normalized" with regard to a gene transcript or a gene expression product refers to the level of the transcript or gene expression product relative to the mean levels of transcripts/products of a set of reference genes, wherein the reference genes are either selected based on their minimal variation across, patients, tissues or treatments ("housekeeping genes"), or the reference genes are the totality of tested genes. In the latter case, which is commonly referred to as "global normalization", it is important that the total number of tested genes be relatively large, preferably greater than 50. Specifically, the term 'normalized' with respect to an RNA transcript refers to the transcript level relative to the mean of transcript levels of a set of reference genes. More specifically, the mean level of an RNA transcript as measured by TaqMan® RT-PCR refers to the Ct value minus the mean Ct values of a set of reference gene transcripts.

The terms "expression threshold," and "defined expression threshold" are used interchangeably and refer to the level of a gene or gene product in question above which the gene or gene product serves as a predictive marker for patient response or resistance to a drug, in the present case an EGFR inhibitor drug. The threshold is defined experimentally from clinical studies such as those described in examples 1 and 2, below. The expression threshold can be selected either for maximum sensitivity (for example, to detect all responders to a drug), or for maximum selectivity (for example to detect only responders to a drug), or for minimum error.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "diagnosis" is used herein to refer to the identification of a molecular or pathological state, disease or condition, such as the identification of a molecular subtype of head and neck cancer, colon cancer, or other type of cancer. The term "prognosis" is used herein to refer to the prediction of the likelihood of cancer-attributable death or progression, including recurrence, metastatic spread, and drug resistance, of a neoplastic disease, such as breast cancer, or head and neck cancer. The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least 5 years, more preferably for at least 8 years, most preferably for at least 10 years following surgery or other treatment.

The term "increased resistance" to a particular drug or treatment option, when used in accordance with the present invention, means decreased response to a standard dose of the drug or to a standard treatment protocol.

The term "decreased sensitivity" to a particular drug or treatment option, when used in accordance with the present invention, means decreased response to a standard dose of the drug or to a standard treatment protocol, where decreased response can be compensated for (at least partially) by increasing the dose of drug, or the intensity of treatment.

"Patient response" can be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "EGFR inhibitor" as used herein refers to a molecule having the ability to inhibit a biological function of a native epidermal growth factor receptor (EGFR). Accordingly, the term "inhibitor" is defined in the context of the biological role of EGFR. While preferred inhibitors herein specifically interact with (e.g. bind to) an EGFR, molecules that inhibit an EGFR biological activity by interacting with other members of the EGFR signal transduction pathway are also specifically included within this definition. A preferred EGFR biological activity inhibited by an EGFR inhibitor is associated with the development, growth, or spread of a tumor.

The term "housekeeping gene" refers to a group of genes that codes for proteins whose activities are essential for the maintenance of cell function. These genes are typically similarly expressed in all cell types. Housekeeping genes include, without limitation, glyceraldehyde-3-phosphate dehydrogenase (GAPDH), Cypl, albumin, actins, e.g. β-actin, tubulins, cyclophilin, hypoxantine phsophoribosyltransferase (HRPT), L32. 28S, and 18S.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

1. Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and reverse transcription polymerase chain reaction (RT-PCR) (Weis et al., Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

2. Reverse Transcriptase PCR (RT-PCR)

Of the techniques listed above, the most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, head and neck, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., *Genome Research* 6:986-994 (1996).

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W. J., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386)

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

5. MassARRAY Technology

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dipensed on a chip array that is pre-loaded with the components needed for MALTI-TOF MS sample preparation. The various cDNAs present in the reaction are quantitated by analyzing the peak areas in the mass spectrum obtained.

6. Gene Expression Analysis by Massively Parallel Signature Sequencing (MPSS

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

7. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

8. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

9. Improved Method for Isolation of Nucleic Acid from Archived Tissue Specimens

In the first step of the method of the invention, total RNA is extracted from the source material of interest, including fixed, paraffin-embedded tissue specimens, and purified sufficiently to act as a substrate in an enzyme assay. While extration of total RNA can be performed by any method known in the art, in a particular embodiment, the invention relies on an improved method for the isolation of nucleic acid from archived, e.g. fixed, paraffin-embedded tissue specimens (FPET).

Measured levels of mRNA species are useful for defining the physiological or pathological status of cells and tissues. RT-PCR (which is discussed above) is one of the most sensitive, reproducible and quantitative methods for this "gene expression profiling". Paraffin-embedded, formalin-fixed tissue is the most widely available material for such studies. Several laboratories have demonstrated that it is possible to successfully use fixed-paraffin-embedded tissue (FPET) as a source of RNA for RT-PCR (Stanta et al., *Biotechniques* 11:304-308 (1991); Stanta et al., *Methods Mol. Biol.* 86:23-26 (1998); Jackson et al., *Lancet* 1:1391 (1989); Jackson et al., *J. Clin. Pathol.* 43:499-504 (1999); Finke et al., *Biotechniques* 14:448-453 (1993); Goldsworthy et al., *Mol. Carcinog.* 25:86-91 (1999); Stanta and Bonin, *Biotechniques* 24:271-276 (1998); Godfrey et al., *J. Mol. Diagnostics* 2:84 (2000); Specht et al., *J. Mol. Med.* 78:B27 (2000); Specht et al., *Am. J. Pathol.* 158:419-429 (2001)). This allows gene expression profiling to be carried out on the most commonly available source of human biopsy specimens, and therefore potentially to create new valuable diagnostic and therapeutic information.

The most widely used protocols utilize hazardous organic solvents, such as xylene, or octane (Finke et al., supra) to dewax the tissue in the paraffin blocks before nucleic acid (RNA and/or DNA) extraction. Obligatory organic solvent removal (e.g. with ethanol) and rehydration steps follow, which necessitate multiple manipulations, and addition of substantial total time to the protocol, which can take up to several days. Commercial kits and protocols for RNA extraction from FPET [MasterPure™ Complete DNA and RNA Purification Kit (EPICENTRE®, Madison, Wis.); Paraffin Block RNA Isolation Kit (Ambion, Inc.) and RNeasy™ Mini kit (Qiagen, Chatsworth, Calif.)] use xylene for deparaffinization, in procedures which typically require multiple centrifugations and ethanol buffer changes, and incubations following incubation with xylene.

The method that can be used in the present invention provides an improved nucleic acid extraction protocol that produces nucleic acid, in particular RNA, sufficiently intact for gene expression measurements. The key step in this improved nucleic acid extraction protocol is the performance of dewaxing without the use of any organic solvent, thereby eliminating the need for multiple manipulations associated with the removal of the organic solvent, and substantially reducing the total time to the protocol. According to the improved method, wax, e.g. paraffin is removed from wax-embedded tissue samples by incubation at 65-75° C. in a lysis buffer that solubilizes the tissue and hydrolyzes the protein, following by cooling to solidify the wax.

Figure 2:
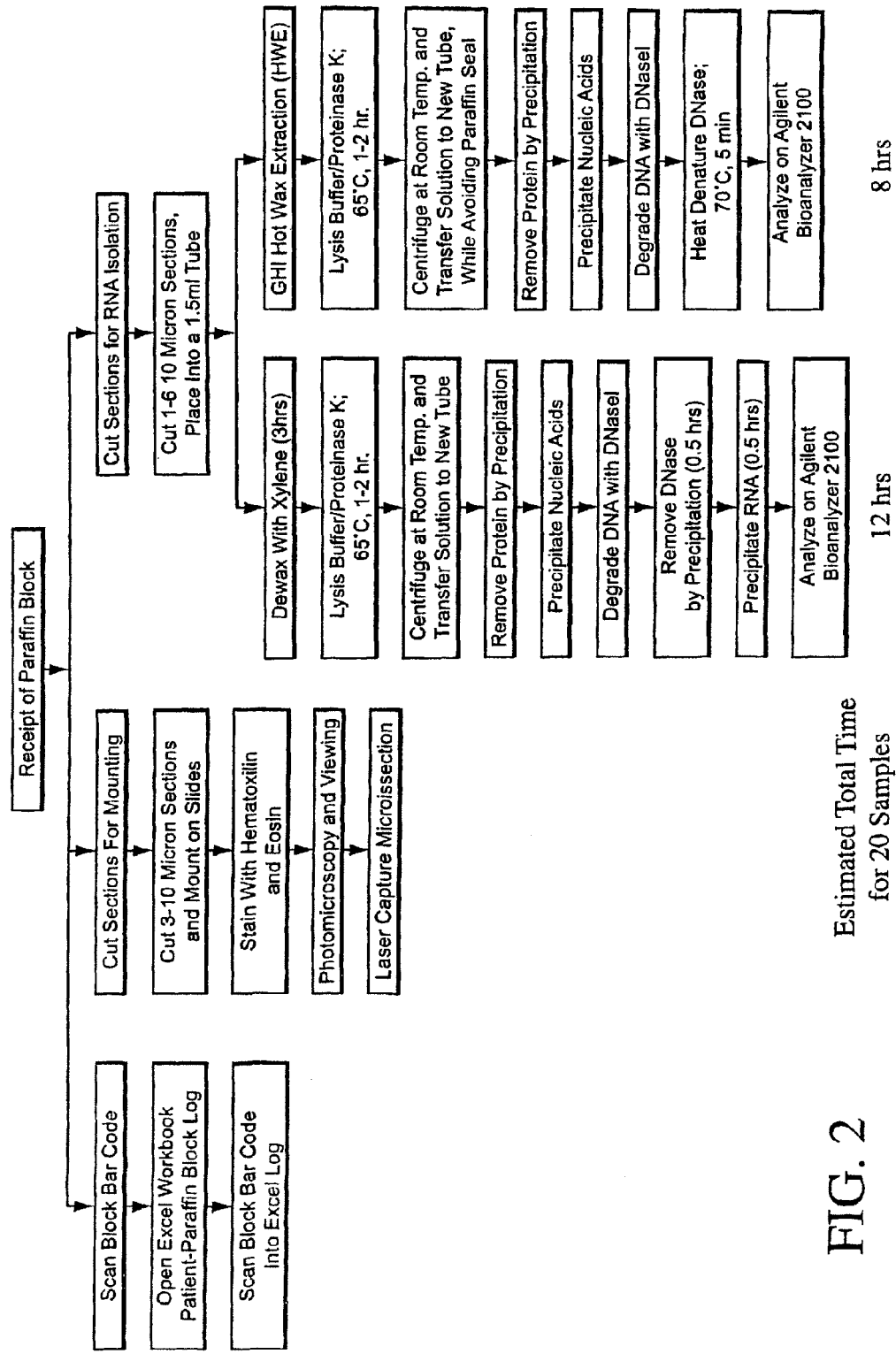
FIG. 2 is a flow chart showing the steps of an RNA extraction method according to the invention alongside a flow chart of a representative commercial method.

FIG. 2 shows a flow chart of the improved RNA extraction protocol used herein in comparison with a representative commercial method, using xylene to remove wax. The times required for individual steps in the processes and for the overall processes are shown in the chart. As shown, the commercial process requires approximately 50% more time than the improved process used in performing the methods of the invention.

The lysis buffer can be any buffer known for cell lysis. It is, however, preferred that oligo-dT-based methods of selectively purifying polyadenylated mRNA not be used to isolate RNA for the present invention, since the bulk of the mRNA molecules are expected to be fragmented and therefore will not have an intact polyadenylated tail, and will not be recovered or available for subsequent analytical assays. Otherwise, any number of standard nucleic acid purification schemes can be used. These include chaotrope and organic solvent extractions, extraction using glass beads or filters, salting out and precipitation based methods, or any of the purification methods known in the art to recover total RNA or total nucleic acids from a biological source.

Lysis buffers are commercially available, such as, for example, from Qiagen, Epicentre, or Ambion. A preferred group of lysis buffers typically contains urea, and Proteinase K or other protease. Proteinase K is very useful in the isolation of high quality, undamaged DNA or RNA, since most mammalian DNases and RNases are rapidly inactivated by this enzyme, especially in the presence of 0.5-1% sodium dodecyl sulfate (SDS). This is particularly important in the case of RNA, which is more susceptible to degradation than DNA. While DNases require metal ions for activity, and can therefore be easily inactivated by chelating agents, such as EDTA, there is no similar co-factor requirement for RNases.

Cooling and resultant solidification of the wax permits easy separation of the wax from the total nucleic acid, which can be conveniently precipitated, e.g. by isopropanol. Further processing depends on the intended purpose. If the proposed method of RNA analysis is subject to bias by contaminating DNA in an extract, the RNA extract can be further treated, e.g. by DNase, post purification to specifically remove DNA while preserving RNA. For example, if the goal is to isolate high quality RNA for subsequent RT-PCR amplification, nucleic acid precipitation is followed by the removal of DNA, usually by DNase treatment. However, DNA can be removed at various stages of nucleic acid isolation, by DNase or other techniques well known in the art.

While the advantages of the improved nucleic acid extraction discussed above are most apparent for the isolation of RNA from archived, paraffin embedded tissue samples, the wax removal step of the present invention, which does not involve the use of an organic solvent, can also be included in any conventional protocol for the extraction of total nucleic acid (RNA and DNA) or DNA only.

By using heat followed by cooling to remove paraffin, the improved process saves valuable processing time, and eliminates a series of manipulations, thereby potentially increasing the yield of nucleic acid.

10. 5'-Multiplexed Gene Specific Priming of Reverse Transcription

RT-PCR requires reverse transcription of the test RNA population as a first step. The most commonly used primer for reverse transcription is oligo-dT, which works well when RNA is intact. However, this primer will not be effective when RNA is highly fragmented as is the case in FPE tissues.

The present invention includes the use of gene specific primers, which are roughly 20 bases in length with a Tm optimum between about 58° C. and 60° C. These primers will also serve as the reverse primers that drive PCR DNA amplification.

An alternative approach is based on the use of random hexamers as primers for cDNA synthesis. However, we have experimentally demonstrated that the method of using a multiplicity of gene-specific primers is superior over the known approach using random hexamers.

11. Normalization Strategy

An important aspect of the present invention is to use the measured expression of certain genes by EGFR-expressing cancer tissue to provide information about the patient's likely response to treatment with an EGFR-inhibitor. For this purpose it is necessary to correct for (normalize away) both differences in the amount of RNA assayed and variability in the quality of the RNA used. Therefore, the assay typically measures and incorporates the expression of certain normalizing genes, including well known housekeeping genes, such as GAPDH and Cyp1. Alternatively or in addition, normalization can be based on the mean or median signal (Ct in the case of RT-PCR) of all of the assayed genes or a large subset thereof (global normalization approach). On a gene-by-gene basis, measured normalized amount of a patient tumor mRNA is compared to the amount found in a reference set of cancer tissue of the same type (e.g. head and neck cancer, colon cancer, etc.). The number (N) of cancer tissues in this reference set should be sufficiently high to ensure that different reference sets (as a whole) behave essentially the same way. If this condition is met, the identity of the individual cancer tissues present in a particular set will have no significant impact on the relative amounts of the genes assayed. Usually, the cancer tissue reference set consists of at least about 30, preferably at least about 40 different FPE cancer tissue specimens. Unless noted otherwise, normalized expression levels for each mRNA/tested tumor/patient will be expressed as a percentage of the expression level measured in the reference set. More specifically, the reference set of a sufficiently high number (e.g. 40) of tumors yields a distribution of normalized levels of each mRNA species. The level measured in a particular tumor sample to be analyzed falls at some percentile within this range, which can be determined by methods well known in the art. Below, unless noted otherwise, reference to expression levels of a gene assume normalized expression relative to the reference set although this is not always explicitly stated.

12. EGFR Inhibitors

The epidermal growth factor receptor (EGFR) family (which includes EGFR, erb-B2, erb-B3, and erb-B4) is a family of growth factor receptors that are frequently activated in epithelial malignancies. Thus, the epidermal growth factor receptor (EGFR) is known to be active in several tumor types, including, for example, ovarian cancer, pancreatic cancer, non-small cell lung cancer, breast cancer, colon cancer and head and neck cancer. Several EGFR inhibitors, such as ZD1839 (also known as gefitinib or Iressa); and OSI774 (Erlotinib, Tarceva™), are promising drug candidates for the treatment of EGFR-expressing cancer.

Iressa, a small synthetic quinazoline, competitively inhibits the ATP binding site of EGFR, a growth-promoting receptor tyrosine kinase, and has been in Phase III clinical trials for the treatment of non-small-cell lung carcinoma. Another EGFR inhibitor, [agr]cyano-[bgr]methyl-N-[(trifluoromethoxy)phenyl]-propenamide (LFM-A12), has been shown to inhibit the proliferation and invasiveness of EGFR positive human breast cancer cells.

Cetuximab is a monoclonal antibody that blocks the EGFR and EGFR-dependent cell growth. It is currently being tested in phase III clinical trials.

Tarceva™ has shown promising indications of anti-cancer activity in patients with advanced ovarian cancer, and non-small cell lung and head and neck carcinomas.

The present invention provides valuable tools to predict whether an EGFR-positive tumor is likely to respond to treatment with an EGFR-inhibitor.

Recent publications further confirm the involvement of EGFR in gastrointestinal (e.g. colon) cancer, and associate its expression with poor survival. See, e.g. Khorana et al., *Proc. Am. Soc. Clin. Oncol* 22:317 (2003).

While the listed examples of EGFR inhibitors a small organic molecules, the findings of the present invention are equally applicable to other EGFR inhibitors, including, without limitation, anti-EGFR antibodies, antisense molecules, small peptides, etc.

Further details of the invention will be apparent from the following non-limiting Examples.

EXAMPLE 1

A Phase II Study of Gene Expression in Head and Neck Tumors

A gene expression study was designed and conducted with the primary goal to molecularly characterize gene expression in paraffin-embedded, fixed tissue samples of head and neck cancer patients who responded or did not respond to treatment with an EGFR inhibitor. The results are based on the use of five different EGFR inhibitor drugs.

Study Design

Molecular assays were performed on paraffin-embedded, formalin-fixed head and neck tumor tissues obtained from 14 individual patients diagnosed with head and neck cancer. Patients were included in the study only if histopathologic assessment, performed as described in the Materials and Methods section, indicated adequate amounts of tumor tissue.

Materials and Methods

Each representative tumor block was characterized by standard histopathology for diagnosis, semi-quantitative assessment of amount of tumor, and tumor grade. A total of 6 sections (10 microns in thickness each) were prepared and placed in two Costar Brand Microcentrifuge Tubes (Polypropylene, 1.7 mL tubes, clear; 3 sections in each tube). If the tumor constituted less than 30% of the total specimen area, the sample may have been crudely dissected by the pathologist, using gross microdissection, putting the tumor tissue directly into the Costar tube.

If more than one tumor block was obtained as part of the surgical procedure, all tumor blocks were subjected to the same characterization, as described above, and the block most representative of the pathology was used for analysis.

Gene Expression Analysis mRNA was extracted and purified from fixed, paraffin-embedded tissue samples, and prepared for gene expression analysis as described above.

Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. During amplification, laser-induced fluorescent signal is collected in real-time through fiber optics cables for all 384 wells, and detected at the CCD. The system includes software for running the instrument and for analyzing the data.

Analysis and Results

Tumor tissue was analyzed for 185 cancer-related genes and 7 reference genes. The threshold cycle (CT) values for each patient were normalized based on the mean of all genes for that particular patient. Clinical outcome data were available for all patients.

Outcomes were classified as either response or no response. The results were analyzed in two different ways using two different criteria for response: partial response, or clinical benefit. The latter criterion combines partial or complete response with stable disease (minimum 3 months). In this study, there were no complete responses, four cases of partial response and two cases of disease stabilization.

We evaluated the relationship between gene expression and partial response by logistic regression and have identified the following genes as significant (p<0.15), as indicated in the attached Table 1. The logistic model provides a means of predicting the probability (Pr) of a subject as being either a partial responder or not. The following equation defined the expression threshold for response.

$$Pr(Response) = \frac{1}{1 + e^{Intercept + Slope \times Reference\ NormalizedCT}}$$

and $Pr(\text{No Response}) = 1 - Pr(\text{Response})$

In Table 1, the term "negative" indicates that greater expression of the gene decreased likelihood of response to treatment with EGFR inhibitor, and "positive" indicates that increased expression of the gene increased likelihood of response to EGFR inhibitor. Results from analysis of head and neck cancer patient data using clinical benefit criteria are shown in Table 2.

Overall increased expression of the following genes correlated with resistance of head and neck cancer to EGFR inhibitor treatment: A-Catenin; AKT1; AKT2; APC; Bax; B-Catenin; BTC; CCNA2; CCNE1; CCNE2; CD105; CD44v3; CD44v6; CD68; CEACAM6; Chk2; cMet; COX2; cripto; DCR3; DIABLO; DPYD; DR5; EDN1 endothelin; EGFR; EIF4E; ERBB4; ERK1; fas; FRP1; GRO1; HB-EGF; HER2; IGF1R; IRS1; ITGA3; KRT17; LAMC2; MTA1; NMYC; PAI1; PDGFA; PGK1; PTPD1; RANBP2; SPRY2; TP53BP1; and VEGFC; and increased expression of the following genes correlated with response of head and neck cancer to EGFR inhibitor treatment: CD44s; CD82; CGA; CTSL; EGFRd27; IGFBP3; p27; P53; RB1; TIMP2; and YB-1.

EXAMPLE 2

A Phase II Study of Gene Expression in Colon Cancer

In a study analogous to the study of head and neck cancer patients described in Example 1, gene expression markers were sought that correlate with increased or decreased likelihood of colon cancer response to EGFR inhibitors. Sample preparation and handling and gene expression and data analysis were performed as in Example 1.

Twenty-three colon adenocarcinoma patients in all were studied, using a 192 gene assay. 188 of the 192 genes were expressed above the limit of detection. Both pathological and clinical responses were evaluated. Following treatment with EGFR inhibitor, three patients were determined to have had a partial response, five to have stable disease and fifteen to have progressive disease.

Table 3 shows the results obtained using the partial response criterion.

Results from analysis of colon cancer patient data using clinical benefit criteria are shown in Table 4.

Overall, increased expression of the following genes correlated with resistance of colon cancer to EGFR inhibitor treatment: CA9; CD134; CD44E; CD44v3; CD44v6; CDC25B; CGA; DR5; GRO1; KRT17; LAMC2; P14ARF; PDGFB; PLAUR; PPARG; RASSF1; RIZ1; Src; TFRC; and UPA, and increased expression of the following genes correlated with sensitivity of colon cancer to EGFR inhibitor treatment: CD44s; CD82; CGA; CTSL; EGFRd27; IGFBP3; p27; P53; RB1; TIMP2; and YB-1.

Finally, it is noteworthy that increased expression of the following genes correlated with resistance to EGFR inhibitor treatment in both head and neck and colon cancer: CD44v3; CD44v6; DR5; GRO1; KRT17; LAMC2.

In similar experiments, the elevated expression of LAMC2, B-Catenin, Bax, GRO1, Fas, or ITGA3 in EGFR-positive head and neck cancer was determined to be an indication that the patient is not likely to respond well to treatment with an EGFR inhibitor. On the other hand, elevated expression of YB-1, PTEN, CTSL, P53, STAT3, ITGB3, IGFBP3, RPLPO or p27 in EGFR-positive head and neck cancer was found to be an indication that the patient is likely to respond to EGFR inhibitor treatment.

In another set of similar experiments, elevated expression of the following genes in EGFR-expressing colon cancer correlated with positive response to treatment: BAK; BCL2; BRAF; BRK; CCND3; CD9; ER2; ERBB4; EREG; ERK1; FRP1. Elevated expression of the following genes in EGFR-expressing colon cancer correlated with resistance to treatment: APN; CA9; CCND1; CDC25B; CD134; LAMC2; PDGFB; CD44v6; CYP1; DR5; GAPDH; IGFBP2; PLAUR; RASSF1; UPA.

All references cited throughout the specification are hereby expressly incorporated by reference.

Although the present invention is illustrated with reference to certain embodiments, it is not so limited. Modifications and variations are possible without diverting from the spirit of the invention. All such modifications and variations, which will be apparent to those skilled in the art, are specifically within the scope of the present invention. While the specific examples disclosed herein concern head and neck cancer and colon cancer, the methods of the present invention are generally applicable and can be extended to all EGFR-expressing cancers, and such general methods are specifically intended to be within the scope herein.

TABLE 1

Partial Response Genes for Head and Neck Study

| Gene Name | Response | Logistic Discriminat Function | | | Likelihood Ratio Test |
|---|---|---|---|---|---|
| | | Intercept | Slope | R2 | P Value |
| cMet | Negative | 26.5168713 | 4.57143179 | 0.6662 | 0.0011 |
| LAMC2 | Negative | 5.29706425 | 1.28137295 | 0.6155 | 0.0017 |
| ITGA3 | Negative | 22.6008544 | 3.17707499 | 0.5063 | 0.0044 |
| CD44v6 | Negative | 6.92255059 | 4.3069909 | 0.492 | 0.005 |
| B-Catenin | Negative | 7.85913706 | 2.52965454 | 0.4805 | 0.0055 |
| PDGFA | Negative | 6.0016358 | 1.10386463 | 0.4318 | 0.0085 |
| GRO1 | Negative | 8.37646635 | 1.74815793 | 0.4146 | 0.0099 |
| ERK1 | Negative | 6.14712633 | 1.64819007 | 0.4024 | 0.0111 |
| CD44v3 | Negative | 5.95094528 | 3.36594473 | 0.3451 | 0.0186 |
| Bax | Negative | 5.34006632 | 1.19383253 | 0.3361 | 0.0202 |
| CGA | Positive | −78.121148 | −10.503757 | 0.3266 | 0.0221 |
| fas | Negative | 7.27491015 | 1.38464586 | 0.3251 | 0.0224 |
| IGFBP3 | Positive | −2.1529531 | −2.7937517 | 0.3097 | 0.0258 |
| MTA1 | Negative | 6.07167277 | 1.23786874 | 0.3072 | 0.0264 |
| YB-1 | Positive | 1.73598983 | −4.0859174 | 0.2814 | 0.0336 |
| DR5 | Negative | 9.0550349 | 1.46349944 | 0.2703 | 0.0373 |
| APC | Negative | 5.775003 | 1.88324269 | 0.2512 | 0.0447 |
| ERBB4 | Negative | 11.9466285 | 1.58606697 | 0.2357 | 0.0518 |
| CD68 | Negative | 3.60605487 | 1.0645631 | 0.2319 | 0.0537 |
| cripto | Negative | 19.5004373 | 2.64909385 | 0.2251 | 0.0574 |
| P53 | Positive | −4.1976158 | −1.5541169 | 0.2208 | 0.0598 |
| VEGFC | Negative | 6.33634489 | 0.90613473 | 0.2208 | 0.0598 |
| A-Catenin | Negative | 4.41215235 | 1.7591194 | 0.2199 | 0.0603 |
| COX2 | Negative | 8.00968996 | 1.27597736 | 0.202 | 0.0718 |
| CD82 | Positive | −1.8999985 | −1.171157 | 0.1946 | 0.0772 |
| PAI1 | Negative | 2.94777884 | 0.97480364 | 0.1944 | 0.0774 |
| AKT2 | Negative | 2.45598587 | 1.64608189 | 0.1889 | 0.0817 |
| HER2 | Negative | 4.25059223 | 0.97748483 | 0.1845 | 0.0853 |
| DIABLO | Negative | 17.035069 | 2.93939741 | 0.1809 | 0.0884 |
| p27 | Positive | −1.9798519 | −1.9041142 | 0.1792 | 0.09 |
| RANBP2 | Negative | 2.85994976 | 0.41878666 | 0.1757 | 0.0931 |
| EIF4E | Negative | 2.91202768 | 0.56099402 | 0.1722 | 0.0965 |

TABLE 1-continued

Partial Response Genes for Head and Neck Study

| Gene Name | Response | Logistic Discriminat Function | | | Likelihood Ratio Test |
| | | Intercept | Slope | R2 | P Value |
| --- | --- | --- | --- | --- | --- |
| EDN1 endothelin | Negative | 6.06858911 | 0.87185553 | 0.1688 | 0.0998 |
| IGF1R | Negative | 6.14387144 | 1.68865744 | 0.1674 | 0.1012 |
| AKT1 | Negative | 5.02676228 | 1.50585593 | 0.1659 | 0.1028 |
| CCNA2 | Negative | 3.95684559 | 0.63089954 | 0.184 | 0.1033 |
| HB-EGF | Negative | 5.1019713 | 0.70368632 | 0.1627 | 0.1061 |
| TIMP2 | Positive | 2.58975885 | −1.0832648 | 0.1625 | 0.1064 |
| EGFRd27 | Positive | −38.789016 | −5.2513587 | 0.1607 | 0.1083 |
| Chk2 | Negative | 6.8797175 | 1.21671205 | 0.1581 | 0.1112 |
| IRS1 | Negative | 12.0545078 | 1.59632708 | 0.1578 | 0.1115 |
| FRP1 | Negative | 3.38233862 | 0.49053452 | 0.1569 | 0.1126 |
| CCNE2 | Negative | 5.78828731 | 1.11609099 | 0.1566 | 0.1129 |
| SPRY2 | Negative | 4.68447069 | 0.86747803 | 0.1552 | 0.1145 |
| KRT17 | Negative | 0.34280253 | 0.412313 | 0.151 | 0.1195 |
| DPYD | Negative | 2.78071456 | 0.78918833 | 0.1504 | 0.1202 |
| CD105 | Negative | 3.13613733 | 0.51406689 | 0.1391 | 0.1351 |
| TP53BP1 | Negative | 3.18676588 | 0.58622276 | 0.1361 | 0.1395 |
| PTPD1 | Negative | 5.85217342 | 1.08545385 | 0.1357 | 0.1401 |
| CTSL | Positive | −2.2283797 | −1.4833372 | 0.1354 | 0.1405 |

TABLE 2

Clinical Benefit Genes for Head and Neck Study

| Gene Name | Response | Logistic Discriminat Function | | | Likelihood Ratio Test |
| | | Intercept | Slope | $R^2$ | P Value |
| --- | --- | --- | --- | --- | --- |
| cMet.2 | Negative | 23.583252 | 4.4082875 | 0.6444 | 0.0007 |
| GRO1.2 | Negative | 10.10717 | 2.46904056 | 0.5388 | 0.0019 |
| A-Catenin.2 | Negative | 5.13298651 | 2.60834812 | 0.3628 | 0.0107 |
| AKT1.3 | Negative | 7.7652606 | 2.83068092 | 0.3044 | 0.0194 |
| DCR3.3 | Negative | 10.2957141 | 1.85012996 | 0.293 | 0.0219 |
| B-Catenin.3 | Negative | 4.21267279 | 1.5417788 | 0.2791 | 0.0252 |
| EDN1 endothelin.1 | Negative | 6.83022814 | 1.14550062 | 0.2758 | 0.0261 |
| CCNE1.1 | Negative | 7.43731399 | 1.21270723 | 0.2661 | 0.0289 |
| LAMC2.2 | Negative | 1.79659862 | 0.56623898 | 0.2498 | 0.0342 |
| CD44v6.1 | Negative | 2.55050577 | 1.87838162 | 0.2071 | 0.0539 |
| DIABLO.1 | Negative | 16.5051841 | 2.99910512 | 0.2066 | 0.0542 |
| CD44v3.2 | Negative | 3.02492619 | 2.05469571 | 0.2002 | 0.058 |
| NMYC.2 | Negative | 23.2010327 | 3.20767305 | 0.1955 | 0.061 |
| CD82.3 | Positive | 2.7521937 | −1.1692268 | 0.188 | 0.0662 |
| RANBP2.3 | Negative | 2.02076788 | 0.42173233 | 0.1807 | 0.0718 |
| RB1.1 | Positive | −5.7352964 | −1.7540651 | 0.1761 | 0.0754 |
| HER2.3 | Negative | 3.87564158 | 1.11486016 | 0.1732 | 0.0779 |
| MTA1.1 | Negative | 3.9020256 | 0.92255645 | 0.1628 | 0.0874 |
| CGA.3 | Positive | −41.909839 | −5.5686182 | 0.1619 | 0.0883 |
| CEACAM6.1 | Negative | 1.66596967 | 0.59307792 | 0.1602 | 0.0899 |
| PTPD1.2 | Negative | 5.51242763 | 1.18616068 | 0.1601 | 0.0901 |
| ERK1.3 | Negative | 2.4144706 | 0.72072834 | 0.154 | 0.0964 |
| Bax.1 | Negative | 2.91338256 | 0.76334619 | 0.152 | 0.0987 |
| STMY3.3 | Positive | −0.9946728 | −0.6053981 | 0.1483 | 0.1028 |
| COX2.1 | Negative | 5.79279616 | 1.0312018 | 0.1478 | 0.1034 |
| EIF4E.1 | Negative | 2.08005397 | 0.55985052 | 0.1468 | 0.1045 |
| YB-1.2 | Positive | 0.45158771 | −2.2935538 | 0.1426 | 0.1096 |
| fas.1 | Negative | 4.05538424 | 0.8686042 | 0.1397 | 0.1134 |
| PDGFA.3 | Negative | 2.43388275 | 0.53168307 | 0.1371 | 0.1168 |
| FRP1.3 | Negative | 2.17320245 | 0.41529609 | 0.137 | 0.1169 |
| PGK1.1 | Negative | 1.86416703 | 1.92395917 | 0.1338 | 0.1212 |
| AKT2.3 | Negative | 1.45131206 | 1.43341036 | 0.1281 | 0.1294 |
| BTC.3 | Negative | 12.1153734 | 1.67411928 | 0.1281 | 0.1294 |
| APC.4 | Negative | 2.50791938 | 0.92506412 | 0.128 | 0.1296 |
| CCNE2.2 | Negative | 3.98727145 | 0.89372321 | 0.1267 | 0.1315 |
| OPN, osteopontin.3 | Positive | −0.522697 | −0.5069258 | 0.1225 | 0.1382 |
| ITGA3.2 | Negative | 2.23381763 | 0.3800099 | 0.1203 | 0.1417 |
| KRT17.2 | Negative | −0.4861169 | 0.43917211 | 0.1184 | 0.1449 |
| CD44s.1 | Positive | −0.9768133 | −0.8896223 | 0.118 | 0.1456 |
| EGFR.2 | Negative | 0.43258354 | 0.46719029 | 0.1162 | 0.1487 |

TABLE 3

Partial Response Genes for Colon Study

| Gene Name | Response | Logistic Discriminat Function Intercept | Slope | $R^2$ | Likelihood Ratio Test P Value |
|---|---|---|---|---|---|
| Bclx_2 | Positive | 2.04896151 | −2.1025144 | 0.172 | 0.0801 |
| BRAF_2 | Positive | −2.5305788 | −3.0987684 | 0.2532 | 0.0337 |
| BRK_2 | Positive | −2.6096501 | −1.577388 | 0.2998 | 0.0209 |
| CA9_3 | Negative | 2.65287578 | 0.83720397 | 0.2758 | 0.0267 |
| Cad17_1 | Positive | −0.0419396 | −1.8773242 | 0.2096 | 0.0533 |
| CCND3_1 | Positive | −1.014844 | −5.1111617 | 0.348 | 0.0128 |
| CCNE1_1 | Positive | −6.5821701 | −0.8939912 | 0.1914 | 0.0648 |
| CCNE2_2 | Positive | 26.1675642 | −1.0709109 | 0.1707 | 0.0812 |
| CD105_1 | Positive | 5.85359096 | −1.2349006 | 0.1302 | 0.1278 |
| CD134_2 | Negative | −5.9286576 | 1.51119518 | 0.1212 | 0.1418 |
| CD44v3_2 | Negative | −1.8184898 | 1.12771829 | 0.2064 | 0.0552 |
| CDC25B_1 | Negative | 10.4351019 | 1.59196005 | 0.2455 | 0.0365 |
| DR5_2 | Negative | −1.7399226 | 1.60177588 | 0.1759 | 0.0767 |
| ErbB3_1 | Positive | 3.65681435 | −0.760436 | 0.1222 | 0.1401 |
| EREG_1 | Positive | −2.3409861 | −1.1217612 | 0.2542 | 0.0333 |
| GPC3_1 | Positive | 4.03889935 | −1.9097648 | 0.3752 | 0.0097 |
| GRO1.2 | Negative | 2.77545378 | 0.74734483 | 0.124 | 0.1359 |
| GUS_1 | Positive | 8.29578416 | −1.9015759 | 0.2105 | 0.0529 |
| HGF_4 | Positive | 5.10609383 | −1.1947949 | 0.2361 | 0.0403 |
| ID1_1 | Positive | 10.6703203 | −1.654146 | 0.216 | 0.0498 |
| ITGB3_1 | Positive | 0.79232612 | −0.827508 | 0.3321 | 0.015 |
| KRT17_2 | Negative | 5.93738146 | 0.93514633 | 0.2133 | 0.0513 |
| LAMC2_2 | Positive | −0.3325052 | 1.41542034 | 0.2475 | 0.0357 |
| P14ARF_1 | Negative | 4.36456658 | 4.10859002 | 0.2946 | 0.022 |
| PDGFB_3 | Negative | −4.7055966 | 1.96517114 | 0.3299 | 0.0154 |
| PLAUR_3 | Negative | 7.51817646 | 0.6862142 | 0.1534 | 0.0983 |
| PTPD1_2 | Positive | −11.659761 | −1.2559081 | 0.1247 | 0.1362 |
| RASSF1_3 | Negative | 6.60631474 | 0.9862129 | 0.1708 | 0.0811 |
| RIZ1_2 | Negative | 2.83817546 | 0.86281198 | 0.1255 | 0.1349 |
| Src_2 | Negative | 4.91364145 | 1.96089745 | 0.1324 | 0.1247 |
| TFRC_3 | Negative | −4.0754666 | 3.03617052 | 0.19 | 0.0658 |
| TITF1_1 | Positive | −1.8849815 | −2.1890987 | 0.1349 | 0.1211 |
| upa_3 | Negative | 4.1059421 | 1.14053848 | 0.1491 | 0.1032 |
| XIAP_1 | Positive | −16.296951 | −2.9502191 | 0.2661 | 0.0295 |

TABLE 4

Clinical Benefit Genes for Colon Study

| Gene Name | Response | Logistic Discriminat Function Intercept | Slope | $R^2$ | Likelihood Ratio Test P Value |
|---|---|---|---|---|---|
| Bak | Positive | −1.347937 | −0.993212 | 0.1189 | 0.0602 |
| BRK | Positive | −3.237705 | −1.1479379 | 0.2567 | 0.0057 |
| CD134 | Negative | 9.9358537 | 1.68440149 | 0.1927 | 0.0167 |
| CD44E | Negative | 3.188991 | 0.59091622 | 0.0958 | 0.0916 |
| CD44v6 | Negative | 5.7352464 | 1.77571293 | 0.2685 | 0.0047 |
| CDC25B | Negative | 2.0664209 | 0.67140598 | 0.0783 | 0.1272 |
| CGA | Negative | 2.7903424 | 0.43834476 | 0.1035 | 0.0794 |
| COX2 | Positive | −1.262804 | −0.4741852 | 0.0733 | 0.1398 |
| DIABLO | Positive | −2.514199 | −1.0753148 | 0.1028 | 0.0805 |
| FRP1 | Positive | −0.401936 | −0.3555899 | 0.0937 | 0.0952 |
| GPC3 | Positive | −7.875276 | −1.7437079 | 0.3085 | 0.0025 |
| HER2 | Positive | 0.1228609 | −0.5549133 | 0.073 | 0.1408 |
| ITGB3 | Positive | −1.593092 | −0.5249778 | 0.1352 | 0.045 |
| PPARG | Negative | 8.6479233 | 1.36115361 | 0.1049 | 0.0774 |
| PTPD1 | Positive | −3.203607 | −1.2049773 | 0.1356 | 0.0447 |
| RPLPO | Positive | 3.5110353 | −1.030518 | 0.0752 | 0.135 |
| STK15 | Positive | −0.664989 | −0.5936475 | 0.0873 | 0.1072 |
| SURV | Positive | −1.409619 | −0.6214924 | 0.074 | 0.1381 |
| TERC | Positive | 1.7755749 | −0.5180083 | 0.1073 | 0.0742 |
| TGFBR2 | Positive | 1.5172396 | −0.9288498 | 0.0934 | 0.0957 |

TABLES 5A–5B

| Gene | Accessin | Sequence | Seq. ID |
|---|---|---|---|
| A-Catenin | NM_00190 | CGTTCCGATCCTCTATACTGCATCCCAGGCATGCCTACAGCACCCTGATGTCGCAGCCTATAAGGCCAACAGGGACCT | 1 |
| AKT1 | NM_00516 | CGCTTCTATGGCGCTGAGATTGTGTCAGCCCTGGACTACCTGCACTCGGAGAAGAACGTGGTGTACCGGGA | 2 |
| AKT2 | NM_00162 | TGCTGCCACGCTTCAAACGTCAGGTCACGTCCGAGGTCGACACAAGGTACTTCGATGATGAATTTACCGCC | 3 |
| APC | NM_00003 | GGACAGCAGGAATGTGTTTCTCCATACAGGTCACGGGGAGCCAATGGTTCAGAAACAAATCGAGTGGGT | 4 |
| B-Catenin | NM_00190 | GGCTCTTGTGCGTACTGTCCTTCGGGCTGGTGACAGGGAAGACATCACTGAGCCTGCCATCTGTGCTCTTCGTCATCTGA | 5 |
| Bak | NM_00118 | CCATTCCCACCATTCTACCTGAGGCCAGGACGTCTGGGGTGTGGGATTGGTGGGTCTATGTTCCC | 6 |
| Bax | NM_00432 | CCGCCGTGGACACAGACTCCCCCCGAGAGGTCTTTTTCCGAGTGGCAGCTGACATGTTTTCTGACGGCAA | 7 |
| Bclx | NM_00119 | CTTTTGTGGAACTCTATGGGACAATGCAGCAGCCGAGAGCCGAAGGGCCAGGAACGCTTCAACCGCTG | 8 |
| BRAF | NM_00433 | CCTTCCGACCAGCAGATGAAGATCATCGAAATCAATTTGGGCAACGAGACCGATCCTCATCAGCTCCCAATGTGCATATAAA | 9 |
| BRK | NM_00597 | GTGCAGGAAAGGTTCACAAATGTGGAGTGTCTGCGTCCAATACACGCGTGTGCTCCTCTCCTTACTCCATCGTGTGTGC | 10 |
| BTC | NM_00172 | AGGGAGATGCCGCTTCGTGGTGGCCGAGCAGACGCCCTCCTGTGTCTGTGATGAAGGCTACATTGGAGCAAGGTGTGAGAG | 11 |
| CA9 | NM_00121 | ATCCTAGCCCTGGTTTTTGGCCTCCTTTTTGCTGTCACCAGCGTCGCGTTCCTTGTGCAGATGAGAAGGCAG | 12 |

TABLES 5A-5B-continued

| Gene | Accessin | Sequence | Seq. ID |
|---|---|---|---|
| Cad17 | NM_00406 | GAAGGCCAAGAACCGAGTCAATTATATTCCAGTTTAAGGCCAATCCTCCTGCTGTGACTTTTGAACTAACTGGGGA | 13 |
| CCNA2 | NM_00123 | CCATACCTCAAGTATTTGCCATCAGTTATTGCTGGAGCTGCCTTTCATTTAGCACTCTACACAGTCACGGGACAAAGCT | 14 |
| CCND3 | NM_00176 | CCTCTGTGCTACAGATTATACCTTTGCCATGTACCCGCCATCCATGATCGCCACGGGCAGCATTGGGCTGCAGTG | 15 |
| CCNE1 | NM_00123 | AAAGAAGATGATGACCGGGTTTACCCAAACTCAACGTGCAAGCCTCGGATTATTGCACCATCCAGAGGCTC | 16 |
| CCNE2 | NM_05774 | ATGCTGTGGCTCCTTCCTAACTGGGGCTTTCTTGACATGTAGGTTGCTTGGTAATAACCGTATATCACAATTTGGGT | 17 |
| CD105 | NM_00011 | GCAGGTGTCAGCAAGTATGATCAGCAATGAGGCGGTGGTCAATATCCTGTCGAGCTCATCACCACAGCGAAAAA | 18 |
| CD134 | NM_00332 | GCCCAGTGCGGAGAACAGGTCCAGCTTGATTCTCGTCTCTGCACTTAAGCTGTTCTCCAGGTGCGTGTGATT | 19 |
| CD44E | X55150 | ATCACCGACAGCACAGACAGAATCCCTGCTACCAATATGGACTCCAGTCATAGTACAACGCTTCAGCCTACTGCAAATCCAAACACAGGT | 20 |
| CD44s | M59040 | GACGAAGACAGTCCCTGGATCACCGACAGCACAGACAGAATCCCTGCTACCAGAGACCAAGACACATTCCACCCCAGT | 21 |
| CD44v3 | AJ251595\ | CACACAAAACAGAACCAGGACTGGACCCAGTGGAACCCAAGCCATTCAAATCCGGAAGTGCTACTTCAG | 22 |
| CD44v6 | AJ251595\ | CTCATACCAGCCATCCAATGCAAGGAAGGACAACACCAAGCCCAGAGGACAGTTCCTGGACTGATTTCTTCAACCCAA | 23 |
| CD68 | NM_00125 | TGGTTCCCAGCCCTGTGTCCACCTCCAAGCCCAGATTCAGATTGAGTCATGTACACAACCCAGGGTGGAGGAG | 24 |
| CD82 | NM_00223 | GTGCAGGCTCAGGTGAAGTGCTGCGGCTGGGTCAGCTTCTACAACTGGACAGACAACGCTGAGCTCATGAATCGCCCTGAGGTC | 25 |
| CD9 | NM_00176 | GGGCGTGGAACAGTTTATCTCAGACATCTGCCCCAAGAAGGACGTACTCGAAACCTTCACCGTG | 26 |
| CDC25B | NM_02187 | AAACGAGCAGTTTGCCATCAGACGCTTCCAGTCTATGCCGGTGAGGCTGCTGGGCCACAGCCCCGTGCTTCGGAACATCACCAAC | 27 |
| CEACAM6 | NM_00248 | CACAGCCTCACTTCTAACCTTCTGGAACCCACCCACCACTGCCAAGCTCACTATTGAATCCACGCCATTCAA | 28 |
| CGA | NM_00127 | CTGAAGGAGCTCCAAGACCTCGCTCTCCAAGGCGCCAAGGAGAGGGCACATCAGCAGAAGAAACACAGCGGTTTTG | 29 |
| Chk2 | NM_00719 | ATGTGGAACCCCCACCTACTTGTGCGCCTGAAGTTCTTGTTTCTGTTGGGACTGCTGGGTATAACCGTGCTGTGGACTG | 30 |
| cMet | NM_00024 | GACATTTCCAGTCCTGCAGTCAATGCCTCTCTGCCCCACCCTTTGTTCAGTGTGGCTGGTGCCACGACAAATGTGTGCGATCGGAG | 31 |
| COX2 | NM_00096 | TCTGCAGAGTTGGAAGCACTCTATGGTGACATCGATGCTGTGGAGCTGTATCCTGCCCTTCTGGTAGAAAAGCCTCGGC | 32 |
| cripto | NM_00321 | GGGTCTGTGCCCCATGACACCTGGCTGCCAAGAAGTGTTCCCTGTGTAAATGCTGGCACGGTCA | 33 |
| CTSL | NM_00191 | GGGAGGCTTATCTCACTGAGTGAGCAGAATCTGGTAGACTGCTCTGGGCCTCAAGGCAATGAAGGCTGCAATGG | 34 |
| DCR3 | NM_01643 | GACCAAGGTCCTGGAATGTCTGCAGCAGAAGGTGAATGGCATCCTGGAGAGCCCTACGGGTACAGGGAAGAC | 35 |
| DIABLO | NM_01988 | CACAATGGCGGCTCTGAAGAGTTGGCTGTCGCGCAGCGTAACTTCATTCTTCAGGTACAGACAGTGTTTGTGT | 36 |
| DPYD | NM_00011 | AGGACGCAAGGAGGGTTTGTCACTGGCAGACTCGAGACTGTAGGCACTGCCATGGCCCCTGTGCTCAGTAAGGACTCGGCGGACATC | 37 |
| DR5 | NM_00384 | CTCTGAGACAGTGCTTCGATGACTTTGCAGACTTGGTGCCCTTTGACTCCTGGGAGCCGCTCATGAGGAAGTTGGGCCTCATGG | 38 |
| EDN1 end | NM_00195 | TGCCACCTGGACATCATTTGGGTCAACACTCCCGAGCACGTTGTTCCGTATGGACTTGGAAGCCCTAGGTCCA | 39 |
| EGFR | NM_00522 | TGTCGATGGACTTCCAGAACCACCTGGGCAGCTGCCAAAAGTGTGATCCAAGCTGTCCCAAT | 40 |
| EGFRd27 | EGFRd27 | GAGTCGGGCTCTGGAGGAAAAGAAAGGTAATTATGTGGTGACAGATCACGGCTCGTGCGTCCGAGCCTGTGG | 41 |
| EIF4E | NM_00196 | GATCTAAGATGGCGACTGTCGAACCGGAAACCACCCCTACTCCTAATCCCCGACTACAGAAGAGGAGAAAACGGAATCTAA | 42 |
| ErbB3 | NM_00198 | CGGTTATGTCATGCCAGATACACACCTCAAAGGTACTCCCTCCTCCCGGGAAGGCACCCTTTCTTCAGTGGGTCTCAGTTC | 43 |

TABLES 5A-5B-continued

| Gene | Accession | Sequence | Seq. ID |
|---|---|---|---|
| ERBB4 | NM_00523 | TGGCTCTTAATCAGTTTCGTTACCTGCCTCTGGAGAATTTACGCATTATTCGTGGGACAAAACTTTATGAGGATCGATATGCCTTG | 44 |
| EREG | NM_00143 | ATAACAAAGTGTAGCTCTGACATGAATGGCTATTGTTTGCATGGACAGTGCATCTATCTGGTGGACATGAGTCAAACTACTGCAGGT | 45 |
| ERK1 | Z11696 | ACGGATCACAGTGGAGGAAGCGCTGGCTCACCCCTACCTGGAGCAGTACTATGACCCGACGGATGAG | 46 |
| fas | NM_00004 | GGATTGCTCAACAACCATGCTGGGCATCTGGACCCTCCTACCTCTGGTTCTTACGTCTGTTGCTAGATTATCGTCCAAAAGTGTTAATGCC | 47 |
| FRP1 | NM_00301 | TTGGTACCTGTGGGTTAGCATCAAGTTCTCCCCAGGGTAGAATTCAATCAGAGCTCCAGTTTGCATTTGGATGTG | 48 |
| GPC3 | NM_00448 | TGATGCGCCTGGAAACAGTCAGCAGGCAACTCCGAAGGACAACGAGATAAGCACCTTTCACAACCTCG | 49 |
| GRO1 | NM_00151 | CGAAAAGATGCTGAACAGTGACAAATCCAACTGACCAGAAGGGAGGAGGAAGCTCACTGGTGGCTGTTCCTGA | 50 |
| GUS | NM_00018 | CCCACTCAGTAGCCAAGTCACAATGTTTGGAAAACAGCCCGTTTACTTGAGCAAGACTGATACCACCTGCGTG | 51 |
| HB-EGF | NM_00194 | GACTCCTTCGTCCCCAGTTGCCGTCTAGGATTGGGCCTCGCATAATTGCTTTGCCAAAATACGAGAGCCTTCAAGTGCCA | 52 |
| HER2 | NM_00444 | CGGTGTGAGAAGTGCAGCAAGCCCTGTGCCCGAGTGTGCTATGGTCTGGGCATGGAGCACTTGCGAGAGG | 53 |
| HGF | M29145 | CCGAAATCCAGATGATGATGCTCATGGACCCTGGTGCTACACGGGAAATCCACTCATTCCTTGGG | 54 |
| ID1 | NM_00216 | AGAACCGCAAGGTGAGCAAGGTGGAGATTCTCCAGCACGTCATCGACTACATCAGGGACCTTCAGTTGGA | 55 |
| IGF1R | NM_00087 | GCATGGTAGCCGAAGATTTCACAGTCAAAATCGGAGATTTTGGTATGACGCGAGATATCTATGAGACAGACTATTACCGGAAA | 56 |
| IGFBP3 | NM_00059 | ACGCACCGGGTGTCTGATCCCAAGTTCCACCCCCTCCATTCAAAGATAATCATCATCAAGAAAGGGCA | 57 |
| IRS1 | NM_00554 | CCACAGCTCACCTTCTGTCAGGTGTCGATCCCAGCTCCAGCAGCTCCCAGAGAGGAAGAGACTGGCACTGAGG | 58 |
| ITGA3 | NM_00220 | CCATGATCCTCACTCTGCTGGTGGACTATACACTCCAGACCTCGCTTAGCATGGTAAATCACCGGCTACAAAGCTTC | 59 |
| ITGB3 | NM_00021 | ACCGGGAGCCCTACATGACCGAAAATACCTGCAACCGTTACTGCCGTGACGAGATTGAGTCAGTGAAAGAGCTTAAGG | 60 |
| KRT17 | NM_00042 | CGAGGATTGGTTCTTCAGCAAGACAGAGGAACTGAACCGCGAGGTGGCCACCAACAGTGAGCTGGTGGAGAGT | 61 |
| LAMC2 | NM_00556 | ACTCAAGCGGAAATTGAAGCAGATAGGTCTTATCAGCACAGTCTCCGCCTCCTGGATTCAGTGTCTCGGCTTCAGGGAGT | 62 |
| MTA1 | NM_00468 | CCGCCCTCACCTGAAGAGAAACGCGCTCCTTGGCGGACACTGGGGGAGGAGAGGAAGAAGCGCGGCTAACTTATTCC | 63 |
| NMYC | NM_00537 | TGAGCGTCGCAGAAACCACAACATCCTGGAGCGCCAGCGCCGCAACGACCTTCGGTCCAGCTTTCTCACGCTCAGGGA | 64 |
| p14ARF | NM_00007 | GCGGAAGGTCCCTCAGACATCCCCGATTGAAAGAACCAGAGAGGCTCTGAGAAACCTCGGGAAACTTAGA | 65 |
| p27 | NM_00406 | CGGTGGACCACGAAGAGTTAACCCGGGACTTGGAGAAGCACTGCAGAGACATGGAAGAGGCGAGCC | 66 |
| P53 | NM_00054 | CTTTGAACCCTTGCTTGCAATAGGTGTGCGTCAGAAGCACCCAGGACTTCCATTTGCTTTGTCCCGGG | 67 |
| PAI1 | NM_00060 | CCGCAACGTGGTTTTCTCACCCTATGGGGTGGCCTCGGTGTTGGCCATGCTCCAGCTGACAACAGGAGGAGAAACGCAGCA | 68 |
| PDGFA | NM_00260 | TTGTTGGTGTGCCCTGGTGCCGTGGTGGCGGTCACTCCCTCTGCTGCCAGTGTTGGACAGAACCCA | 69 |
| PDGFB | NM_00260 | ACTGAAGGAGACCCTTGGAGCCTAGGGGCATCGGCAGGAGAGTGTGTGGGCAGGGTTATTTA | 70 |
| PGK1 | NM_00029 | AGAGCCAGTTGCTGTAGAACTCAAATCTCTGGTGGGCAAGGATGTTCTGTTCTTGAAGGACTGTGTAGGCCCAG | 71 |
| PLAUR | NM_00265 | CCCATGGATGCTCCTCTGAAGAGACTTTCCTCATTGACTGCCGAGGCCCCATGAATCAATGTCTGGTAGCCACCGG | 72 |
| PPARG | NM_00503 | TGACTTTATGGAGCCCAAGTTTGAGTTTGCTGTGAAGTTCAATGCACTGGAATTAGATGACAGCGACTTGGC | 73 |
| PTPD1 | NM_00703 | CGCTTGCCTAACTCATACTTTCCCGTTGACACTTGATCCACGCAGCGTGGCACTGGGACGTAAGTGGCGCAGTCTGAATGG | 74 |
| RANBP2 | NM_00626 | TCCTTCAGCTTTCACACTGGGCTCAGAAATGAAGTTGCATGACTCTTCTGGAAGTCAGGTGGGAACAGGATTT | 75 |
| RASSF1 | NM_00718 | AGTGGGAGACACCTGACCTTTCTCAAGGTGAGATTGAGCAGAAGATCAAGGAGTACAATGCCCAGATCA | 76 |

TABLES 5A-5B-continued

| Gene | Accessin | Sequence | Seq. ID |
|---|---|---|---|
| RB1 | NM_00032 | CGAAGCCCTTACAAGTTTCCTAGTTCACCCTTACGGATTCCTGGAGGGAACATGTATATTTCACCCCTGAAGAGTCC | 77 |
| RIZ1 | NM_01223 | CCAGACGAGCGATTAGAAGCGGCAGCTTGTGAGGTGAATGATTTGGGGGAAGAGGAGGAGGAGGAAGAGGAGGA | 78 |
| RPLPO | NM_00100 | CCATTCTATCATCAACGGGTACAAACGAGTCCTGGCCTTGTCTGTGGAGACGGATTACACCTTCCCACTTGCTGA | 79 |
| SPRY2 | NM_00584 | TGTGGCAAGTGCAAATGTAAGGAGTGCACCTACCCAAGGCCTCTGCCATCAGACTGGATCTGCGAC | 80 |
| Src | NM_00438 | CCTGAACATGAACATGAAGGAGCTGAAGCTGCTGCAGACCATCGGGAAGGGGGAGTTCGGAGACGTGATG | 81 |
| STK15 | NM_00360 | CATCTTCCAGGAGGACCACTCTCTGTGGCACCCTGGACTACCTGCCCCCTGAAATGATTGAAGGTCGGA | 82 |
| SURV | NM_00116 | TGTTTTGATTCCCGGGCTTACCAGGTGAGAAGTGAGGGAGGAAGAAGGCAGTGTCCCTTTTGCTAGAGCTGACAGCTTTG | 83 |
| TERC | U86046 | AAGAGGAACGGAGCGAGTCCCCGCGCGCGGCGCGATTCCCTGAGCTGTGGGACGTGCACCCAGGACTCGGCTCACACAT | 84 |
| TFRC | NM_00323 | GCCAACTGCTTTCATTTGTGAGGGATCTGAACCAATACAGAGCAGACATAAAGGAAATGGGCCTGAGT | 85 |
| TGFBR2 | NM_00324 | AACACCAATGGGTTCCATCTTTCTGGGCTCCTGATTGCTCAAGCACAGTTTGGCCTGATGAAGAGG | 86 |
| TIMP2 | NM_00325 | TCACCCTCTGTGACTTCATCGTGCCCTGGGACACCCTGAGCACCACCCAGAAGAAGAGCCTGAACCACA | 87 |
| TITF1 | NM_00331 | CGACTCCGTTCTCAGTGTCTGACATCTTGAGTCCCCTGGAGGAAAGCTACAAGAAAGTGGGCATGGAGGG | 88 |
| TP53BP1 | NM_00565 | TGCTGTTGCTGAGTCTGTTGCCAGTCGCCAGAAGACGATGTCTGTGTTGAGCTGTATCTGTGAAGCCAGGCAAG | 89 |
| upa | NM_00265 | GTGGATGTGCCCTGAAGGACAAGCCAGGCGTCTACACGAGAGTCTCACACTTCTTACCCTGGATCCGCAG | 90 |
| VEGFC | NM_00542 | CCTCAGCAAGACGTTATTTGAAATTACAGTGCCTCTCTCAAGGCCCCAAACCAGTAACAATCAGTTTTGCCAATCACACTT | 91 |
| XIAP | NM_00116 | GCAGTTGGAAGACACAGGAAAGTATCCCCAAATTGCAGATTTATCAACGGCTTTTATCTTGAAAATAGTGCCACGCA | 92 |
| YB-1 | NM_00455 | AGACTGTGGAGTTTGATGTTGTTGAAGGAGAAAAGGGTGCGGAGGCAGCAAATGTTACAGGTCCTGGTGGTGTTCC | 93 |

TABLES 6A-6F

| Gene | Accession | Name | Sequence | Length | Seq ID. |
|---|---|---|---|---|---|
| A-Catenin | NM_001903 | S2138/A-Cate.f2 | CGTTCCGATCCTCTATACTGCAT | 23 | 94 |
| A-Catenin | NM_001903 | S2139/A-Cate.r2 | AGGTCCCTGTTGGCCTTATAGG | 22 | 95 |
| A-Catenin | NM_001903 | S4725/A-Cate.p2 | ATGCCTACAGCACCCTGATGTCGCA | 25 | 96 |
| AKT1 | NM_005163 | S0010/AKT1.f3 | CGCTTCTATGGCGCTGAGAT | 20 | 97 |
| AKT1 | NM_005163 | S0012/AKT1.r3 | TCCCGGTACACCACGTTCTT | 20 | 98 |
| AKT1 | NM_005163 | S4776/AKT1.p3 | CAGCCCTGGACTACCTGCACTCGG | 24 | 99 |
| AKT2 | NM_001626 | S0828/AKT2.f3 | TCCTGCCACCCTTCAAACC | 19 | 100 |
| AKT2 | NM_001626 | S0829/AKT2.r3 | GGCGGTAAATTCATCATCGAA | 21 | 101 |
| AKT2 | NM_001626 | S4727/AKT2.p3 | CAGGTCACGTCCGAGGTCGACACA | 24 | 102 |
| APC | NM_000038 | S0022/APC.f4 | GGACAGCAGGAATGTGTTTC | 20 | 103 |
| APC | NM_000038 | S0024/APC.r4 | ACCCACTCGATTTGTTCTG | 20 | 104 |
| APC | NM_000038 | S4888/APC.p4 | CATTGGCTCCCGTGACCTGTA | 22 | 105 |
| B-Catenin | NM_001904 | S2150/B-Cate.f3 | GGCTCTTGTGCGTACTGTCCTT | 22 | 106 |
| B-Catenin | NM_001904 | S2151/B-Cate.r3 | TCAGATGACGAAGAGCACAGATG | 23 | 107 |
| B-Catenin | NM_001904 | S5046/B-Cate.p3 | AGGCTCAGTGATGTCTTCCCTGTCACCAG | 29 | 108 |
| Bak | NM_001188 | S0037/Bak.f2 | CCATTCCCACCATTCTACCT | 20 | 109 |
| Bak | NM_001188 | S0039/Bak.r2 | GGGAACATAGACCCACCAAT | 20 | 110 |

TABLES 6A-6F-continued

| Gene | Accession | Name | Sequence | Length | Seq ID. |
|---|---|---|---|---|---|
| Bak | NM_001188 | S4724/Bak.p2 | ACACCCCAGACGTCCTGGCCT | 21 | 111 |
| Bax | NM_004324 | S0040/Bax.f1 | CCGCCGTGGACACAGACT | 18 | 112 |
| Bax | NM_004324 | S0042/Bax.r1 | TTGCCGTCAGAAAACATGTCA | 21 | 113 |
| Bax | NM_004324 | S4897/Bax.p1 | TGCCACTCGGAAAAAGACCTCTCGG | 25 | 114 |
| Bclx | NM_001191 | S0046/Bclx.f2 | CTTTTGTGGAACTCTATGGGAACA | 24 | 115 |
| Bclx | NM_001191 | S0048/Bclx.r2 | CAGCGGTTGAAGCGTTCCT | 19 | 116 |
| Bclx | NM_001191 | S4898/Bclx.p2 | TTCGGCTCTCGGCTGCTGCA | 20 | 117 |
| BRAF | NM_004333 | S3027/BRAF.f2 | CCTTCCGACCAGCAGATGAA | 20 | 118 |
| BRAF | NM_004333 | S3028/BRAF.r2 | TTTATATGCACATTGGGAGCTGAT | 24 | 119 |
| BRAF | NM_004333 | S4818/BRAF.p2 | CAATTTGGGCAACGAGACCGATCCT | 25 | 120 |
| BRK | NM_005975 | S0678/BRK.f2 | GTGCAGGAAAGGTTCACAAA | 20 | 121 |
| BRK | NM_005975 | S0679/BRK.r2 | GCACACGATGGAGTAAGG | 20 | 122 |
| BRK | NM_005975 | S4789/BRK.p2 | AGTGTCTGCGTCCAATACACGCGT | 24 | 123 |
| BTC | NM_001729 | S1216/BTC.f3 | AGGGAGATGCCGCTTCGT | 18 | 124 |
| BTC | NM_001729 | S1217/BTC.r3 | CTCTCACACCTTGCTCCAATGTA | 23 | 125 |
| BTC | NM_001729 | S4844/BTC.p3 | CCTTCATCACAGACACAGGAGGGCG | 25 | 126 |
| CA9 | NM_001216 | S1398/CA9.f3 | ATCCTAGCCCTGGTTTTTGG | 20 | 127 |
| CA9 | NM_001216 | S1399/CA9.r3 | CTGCCTTCTCATCTGCACAA | 20 | 128 |
| CA9 | NM_001216 | S4938/CA9.p3 | TTTGCTGTCACCAGCGTCGC | 20 | 129 |
| Cad17 | NM_004063 | S2186/Cad17.f1 | GAAGGCCAAGAACCGAGTCA | 20 | 130 |
| Cad17 | NM_004063 | S2187/Cad17.r1 | TCCCCAGTTAGTTCAAAAGTCACA | 24 | 131 |
| Cad17 | NM_004063 | S5038/Cad17.p1 | TTATATTCCAGTTTAAGGCCAATCCTC | 27 | 132 |
| CCNA2 | NM_001237 | S3039/CCNA2.f1 | CCATACCTCAAGTATTTGCCATCAG | 25 | 133 |
| CCNA2 | NM_001237 | S3040/CCNA2.r1 | AGCTTTGTCCCGTGACTGTGTA | 22 | 134 |
| CCNA2 | NM_001237 | S4820/CCNA2.p1 | ATTGCTGGAGCTGCCTTTCATTTAGCACT | 29 | 135 |
| CCND3 | NM_001760 | S2799/CCND3.f1 | CCTCTGTGCTACAGATTATACCTTTGC | 27 | 136 |
| CCND3 | NM_001760 | S2800/CCND3.r1 | CACTGCAGCCCCAATGCT | 18 | 137 |
| CCND3 | NM_001760 | S4966/CCND3.p1 | TACCCGCCATCCATGATCGCCA | 22 | 138 |
| CCNE1 | NM_001238 | S1446/CCNE1.f1 | AAAGAAGATGATGACCGGGTTTAC | 24 | 139 |
| CCNE1 | NM_001238 | S1447/CCNE1.r1 | GAGCCTCTGGATGGTGCAAT | 20 | 140 |
| CCNE1 | NM_001238 | S4944/CCNE1.p1 | CAAACTCAACGTGCAAGCCTCGGA | 24 | 141 |
| CCNE2 | NM_057749 | S1458/CCNE2.f2 | ATGCTGTGGCTCCTTCCTAACT | 22 | 142 |
| CCNE2 | NM_057749 | S1459/CCNE2.r2 | ACCCAAATTGTGATATACAAAAGGTT | 27 | 143 |
| CCNE2 | NM_057749 | S4945/CCNE2.p2 | TACCAAGCAACCTACATGTCAAGAAAGCCC | 30 | 144 |
| CD105 | NM_000118 | S1410/CD105.f1 | GCAGGTGTCAGCAAGTATGATCAG | 24 | 145 |
| CD105 | NM_000118 | S1411/CD105.r1 | TTTTTCCGCTGTGGTGATGA | 20 | 146 |
| CD105 | NM_000118 | S4940/CD105.p1 | CGACAGGATATTGACCACCGCCTCATT | 27 | 147 |
| CD134 | NM_003327 | S3138/CD134.f2 | GCCCAGTGCGGAGAACAG | 18 | 148 |
| CD134 | NM_003327 | S3139/CD134.r2 | AATCACACGCACCTGGAGAAC | 21 | 149 |

TABLES 6A-6F-continued

| Gene | Accession | Name | Sequence | Length | Seq ID. |
|---|---|---|---|---|---|
| CD134 | NM_003327 | S3241/CD134.p2 | CCAGCTTGATTCTCGTCTCTGCACTTAAGC | 30 | 150 |
| CD44E | X55150 | S3267/CD44E.f1 | ATCACCGACAGCACAGACA | 19 | 151 |
| CD44E | X55150 | S3268/CD44E.r1 | ACCTGTGTTTGGATTTGCAG | 20 | 152 |
| CD44E | X55150 | S4767/CD44E.p1 | CCCTGCTACCAATATGGACTCCAGTCA | 27 | 153 |
| CD44s | M59040 | S3102/CD44s.f1 | GACGAAGACAGTCCCTGGAT | 20 | 154 |
| CD44s | M59040 | S3103/CD44s.r1 | ACTGGGGTGGAATGTGTCTT | 20 | 155 |
| CD44s | M59040 | S4826/CD44s.p1 | CACCGACAGCACAGACAGAATCCC | 24 | 156 |
| CD44v3 | AJ251595v3 | S2997/CD44v3.f2 | CACACAAAACAGAACCAGGACT | 22 | 157 |
| CD44v3 | AJ251595v3 | S2998/CD44v3.r2 | CTGAAGTAGCACTTCCGGATT | 21 | 157 |
| CD44v3 | AJ251595v3 | S4814/CD44v3.p2 | ACCCAGTGGAACCCAAGCCATTC | 23 | 159 |
| CD44v6 | AJ251595v6 | S3003/CD44v6.f1 | CTCATACCAGCCATCCAATG | 20 | 160 |
| CD44v6 | AJ251595v6 | S3004/CD44v6.r1 | TTGGGTTGAAGAAATCAGTCC | 21 | 161 |
| CD44v6 | AJ251595v6 | S4815/CD44v6.p1 | CACCAAGCCCAGAGGACAGTTCCT | 24 | 162 |
| CD68 | NM_001251 | S0067/CD68.f2 | TGGTTCCCAGCCCTGTGT | 18 | 163 |
| CD68 | NM_001251 | S0069/CD68.r2 | CTCCTCCACCCTGGGTTGT | 19 | 164 |
| CD68 | NM_001251 | S4734/CD68.p2 | CTCCAAGCCCAGATTCAGATTCGAGTCA | 28 | 165 |
| CD82 | NM_002231 | S0684/CD82.f3 | GTGCAGGCTCAGGTGAAGTG | 20 | 166 |
| CD82 | NM_002231 | S0685/CD82.r3 | GACCTCAGGGCGATTCATGA | 20 | 167 |
| CD82 | NM_002231 | S4790/CD82.p3 | TCAGCTTCTACAACTGGACAGACAACGCTG | 30 | 168 |
| CD9 | NM_001769 | S0686/CD9.f1 | GGGCGTGGAACAGTTTATCT | 20 | 168 |
| CD9 | NM_001769 | S0687/CD9.r1 | CACGGTGAAGGTTTCGAGT | 19 | 170 |
| CD9 | NM_001769 | S4792/CD9.p1 | AGACATCTGCCCCAAGAAGGACGT | 24 | 171 |
| CDC25B | NM_021874 | S1160/CDC25B.f1 | AAACGAGCAGTTTGCCATCAG | 21 | 172 |
| CDC25B | NM_021874 | S1161/CDC25B.r1 | GTTGGTGATGTTCCGAAGCA | 20 | 176 |
| CDC25B | NM_021874 | S4842/CDC25B.p1 | CCTCACCGGCATAGACTGGAAGCG | 24 | 174 |
| CEACAM6 | NM_002483 | S3197/CEACAM.f1 | CACAGCCTCACTTCTAACCTTCTG | 24 | 175 |
| CEACAM6 | NM_002483 | S3198/CEACAM.r1 | TTGAATGGCGTGGATTCAATAG | 22 | 176 |
| CEACAM6 | NM_002483 | S3261/CEACAM.p1 | ACCCACCCACCACTGCCAAGCTC | 23 | 177 |
| CGA | NM_001275 | S3221/CGA.f3 | CTGAAGGAGCTCCAAGACCT | 20 | 178 |
| CGA | NM_001275 | S3222/CGA.r3 | CAAAACCGCTGTGTTTCTTC | 20 | 179 |
| CGA | NM_001275 | S3254/CGA.p3 | TGCTGATGTGCCCTCTCCTTGG | 22 | 180 |
| Chk2 | NM_007194 | S1434/Chk2.f3 | ATGTGGAACCCCCACCTACTT | 21 | 181 |
| Chk2 | NM_007194 | S1435/Chk2.r3 | CAGTCCACAGCACGGTTATACC | 22 | 182 |
| Chk2 | NM_007194 | S4942/Chk2.p3 | AGTCCCAACAGAAACAAGAACTTCAGGCG | 29 | 183 |
| cMet | NM_000245 | S0082/cMet.f2 | ACATTTCCAGTCCTGCAGTCA | 22 | 184 |
| cMet | NM_000245 | S0084/cMet.r2 | CTCCGATCGCACACATTTGT | 20 | 185 |
| cMet | NM_000245 | S4993/cMet.p2 | TGCCTCTCTGCCCCACCCTTTGT | 23 | 186 |
| COX2 | NM_000963 | S0088/COX2.f1 | TCTGCAGAGTTGGAAGCACTCTA | 23 | 187 |
| COX2 | NM_000963 | S0090/COX2.r1 | GCCGAGGCTTTTCTACCAGAA | 21 | 188 |

TABLES 6A-6F-continued

| Gene | Accession | Name | Sequence | Length | Seq ID. |
|---|---|---|---|---|---|
| COX2 | NM_000963 | S4995/COX2.p1 | CAGGATACAGCTCCACAGCATCGATGTC | 28 | 189 |
| cripto | NM_003212 | S3117/cripto.f1 | GGGTCTGTGCCCCATGAC | 18 | 190 |
| cripto | NM_003212 | S3118/cripto.r1 | TGACCGTGCCAGCATTTACA | 20 | 191 |
| cripto | NM_003212 | S3237/cripto.p1 | CCTGGCTGCCCAAGAAGTGTTCCCT | 25 | 192 |
| CTSL | NM_001912 | S1303/CTSL.f2 | GGGAGGCTTATCTCACTGAGTGA | 23 | 193 |
| CTSL | NM_001912 | S1304/CTSL.r2 | CCATTGCAGCCTTCATTGC | 19 | 194 |
| CTSL | NM_001912 | S4899/CTSL.p2 | TTGAGGCCCAGAGCAGTCTACCAGATTCT | 29 | 195 |
| DCR3 | NM_016434 | S1786/DCR3.f3 | GACCAAGGTCCTGGAATGTC | 20 | 196 |
| DCR3 | NM_016434 | S1787/DCR3.r3 | GTCTTCCCTGTACCCGTAGG | 20 | 197 |
| DCR3 | NM_016434 | S4982/DCR3.p3 | CAGGATGCCATTCACCTTCTGCTG | 24 | 198 |
| DIABLO | NM_019887 | S0808/DIABLO.f1 | CACAATGGCGGCTCTGAAG | 19 | 199 |
| DIABLO | NM_019887 | S0809/DIABLO.r1 | ACACAAACACTGTCTGTACCTGAAGA | 26 | 200 |
| DIABLO | NM_019887 | S4813/DIABLO.p1 | AAGTTACGCTGCGCGACAGCCAA | 23 | 201 |
| DPYD | NM_000110 | S0100/DPYD.f2 | AGGACGCAAGGAGGGTTTG | 19 | 202 |
| DPYD | NM_000110 | S0102/DPYD.r2 | GATGTCCGCCGAGTCCTTACT | 21 | 203 |
| DPYD | NM_000110 | S4998/DPYD.p2 | CAGTGCCTACAGTCTCGAGTCTGCCAGTG | 29 | 204 |
| DR5 | NM_003842 | S2551/DR5.f2 | CTCTGAGACAGTGCTTCGATGACT | 24 | 205 |
| DR5 | NM_003842 | S2552/DR5.r2 | CCATGAGGCCCAACTTCCT | 19 | 206 |
| DR5 | NM_003842 | S4979/DR5.p2 | CAGACTTGGTGCCCTTTGACTCC | 23 | 207 |
| EDN1 endothelin | NM_001955 | S0774/EDN1 e.f1 | TGCCACCTGGACATCATTTG | 20 | 208 |
| EDN1 endothelin | NM_001955 | S0775/EDN1 e.r1 | TGGACCTAGGGCTTCCAAGTC | 21 | 209 |
| EDN1 endothelin | NM_001955 | S4806/EDN1 e.p1 | CACTCCCGAGCACGTTGTTCCGT | 23 | 210 |
| EGFR | NM_005228 | S0103/EGFR.f2 | TGTCGATGGACTTCCAGAAC | 20 | 211 |
| EGFR | NM_005228 | S0105/EGFR.r2 | ATTGGGACAGCTTGGATCA | 19 | 212 |
| EGFR | NM_005228 | S4999/EGFR.p2 | CACCTGGGCAGCTGCCAA | 18 | 213 |
| EGFRd27 | EGFRd27 | S2484/EGFRd2.f2 | GAGTCGGGCTCTGGAGGAAAAG | 22 | 214 |
| EGFRd27 | EGFRd27 | S2485/EGFRd2.r2 | CCACAGGCTCGGACGCAC | 18 | 215 |
| EGFRd27 | EGFRd27 | S4935/EGFRd2.p2 | AGCCGTGATCTGTCACCACATAATTACC | 28 | 216 |
| EIF4E | NM_001968 | S0106/EIF4E.f1 | GATCTAAGATGGCGACTGTCGAA | 23 | 217 |
| EIF4E | NM_001968 | S0108/EIF4E.r1 | TTAGATTCCGTTTTCTCCTCTTCTG | 25 | 218 |
| EIF4E | NM_001968 | S5000/EIF4E.p1 | ACCACCCCTACTCCTAATCCCCGACT | 27 | 219 |
| ErbB3 | NM_001982 | S0112/ErbB3.f1 | CGGTTATGTCATGCCAGATACAC | 23 | 220 |
| ErbB3 | NM_001982 | S0114/ErbB3.r1 | GAACTGAGACCCACTGAAGAAAGG | 24 | 221 |
| ErbB3 | NM_001982 | S5002/ErbB3.p1 | CCTCAAAGGTACTCCCTCCTCCCGG | 25 | 222 |
| ERBB4 | NM_005235 | S1231/ERBB4.f3 | TGGCTCTTAATCAGTTTCGTTACCT | 25 | 223 |
| ERBB4 | NM_005235 | S1232/ERBB4.r3 | CAAGGCATATCGATCCTCATAAAGT | 25 | 224 |
| ERBB4 | NM_005235 | S4891/ERBB4.p3 | TGTCCCACGAATAATGCGTAAATTCTCCAG | 30 | 225 |

TABLES 6A-6F-continued

| Gene | Accession | Name | Sequence | Length | Seq ID. |
|---|---|---|---|---|---|
| EREG | NM_001432 | S0670/EREG.f1 | ATAACAAAGTGTAGCTCTGACATGAATG | 28 | 226 |
| EREG | NM_001432 | S0671/EREG.r1 | CACACCTGCAGTAGTTTTGACTCA | 24 | 227 |
| EREG | NM_001432 | S4772/EREG.p1 | TTGTTTGCATGGACAGTGCATCTATCTGGT | 30 | 228 |
| ERK1 | Z11696 | S1560/ERK1.f3 | ACGGATCACAGTGGAGGAAG | 20 | 229 |
| ERK1 | Z11696 | S1561/ERK1.r3 | CTCATCCGTCGGGTCATAGT | 20 | 230 |
| ERK1 | Z11696 | S4882/ERK1.p3 | CGCTGGCTCACCCCTACCTG | 20 | 231 |
| fas | NM_000043 | S0118/fas.f1 | GGATTGCTCAACAACCATGCT | 21 | 232 |
| fas | NM_000043 | S0120/fas.r1 | GGCATTAACACTTTTGGACGATAA | 24 | 233 |
| fas | NM_000043 | S5003/fas.p1 | TCTGGACCCTCCTACCTCTGGTTCTTACGT | 30 | 234 |
| FRP1 | NM_003012 | S1804/FRP1.f3 | TTGGTACCTGTGGGTTAGCA | 20 | 235 |
| FRP1 | NM_003012 | S1805/FRP1.r3 | CACATCCAAATGCAAACTGG | 20 | 236 |
| FRP1 | NM_003012 | S4983/FRP1.p3 | TCCCCAGGGTAGAATTCAATCAGAGC | 26 | 237 |
| GPC3 | NM_004484 | S1835/GPC3.f1 | TGATGCGCCTGGAAACAGT | 19 | 238 |
| GPC3 | NM_004484 | S1836/GPC3.r1 | CGAGGTTGTGAAAGGTGCTTATC | 23 | 239 |
| GPC3 | NM_004484 | S5036/GPC3.p1 | AGCAGGCAACTCCGAAGGACAACG | 24 | 240 |
| GRO1 | NM_001511 | S0133/GRO1.f2 | CGAAAAGATGCTGAACAGTGACA | 23 | 241 |
| GRO1 | NM_001511 | S0135/GRO1.r2 | TCAGGAACAGCCACCAGTGA | 20 | 242 |
| GRO1 | NM_001511 | S5006/GRO1.p2 | CTTCCTCCTCCCTTCTGGTCAGTTGGAT | 28 | 243 |
| GUS | NM_000181 | S0139/GUS.f1 | CCCACTCAGTAGCCAAGTCA | 20 | 244 |
| GUS | NM_000181 | S0141/GUS.r1 | CACGCAGGTGGTATCAGTCT | 20 | 245 |
| GUS | NM_000181 | S4740/GUS.p1 | TCAAGTAAACGGGCTGTTTTCCAAACA | 27 | 246 |
| HB-EGF | NM_001945 | S0662/HB-EGF.f1 | GACTCCTTCGTCCCCAGTTG | 20 | 247 |
| HB-EGF | NM_001945 | S0663/HB-EGF.r1 | TGGCACTTGAAGGCTCTGGTA | 21 | 248 |
| HB-EGF | NM_001945 | S4787/HB-EGF.p1 | TTGGGCCTCCCATAATTGCTTTGCC | 25 | 249 |
| HER2 | NM_004448 | S0142/HER2.f3 | CGGTGTGAGAAGTGCAGCAA | 20 | 250 |
| HER2 | NM_004448 | S0144/HER2.r3 | CCTCTCGCAAGTGCTCCAT | 19 | 251 |
| HER2 | NM_004448 | S4729/HER2.p3 | CCAGACCATAGCACACTCGGGCAC | 24 | 242 |
| HGF | M29145 | S1327/HGF.f4 | CCGAAATCCAGATGATGATG | 20 | 253 |
| HGF | M29145 | S1328/HGF.r4 | CCCAAGGAATGAGTGGATTT | 20 | 254 |
| HGF | M29145 | S4901/HGF.p4 | CTCATGGACCCTGGTGCTACACG | 23 | 255 |
| ID1 | NM_002165 | S0820/ID1.f1 | AGAACCGCAAGGTGAGCAA | 19 | 256 |
| ID1 | NM_002165 | S0821/ID1.r1 | TCCAACTGAAGGTCCCTGATG | 21 | 257 |
| ID1 | NM_002165 | S4832/ID1.p1 | TGGAGATTCTCCAGCACGTCATCGAC | 26 | 258 |
| IGF1R | NM_000875 | S1249/IGF1R.f3 | GCATGGTAGCCGAAGATTTCA | 21 | 259 |
| IGF1R | NM_000875 | S1250/IGF1R.r3 | TTTCCGGTAATAGTCTGTCTCATAGATATC | 30 | 260 |
| IGF1R | NM_000875 | S4895/IGF1R.p3 | CGCGTCATACCAAAATCTCCGATTTGA | 28 | 261 |
| IGFBP3 | NM_000598 | S0157/IGFBP3.f3 | ACGCACCGGGTGTCTGA | 17 | 262 |
| IGFBP3 | NM_000598 | S0159/IGFBP3.r3 | TGCCCTTTCTTGATGATGATTATC | 24 | 263 |
| IGFBP3 | NM_000598 | S5011/IGFBP3.p3 | CCCAAGTTCCACCCCCTCCATTCA | 24 | 264 |

TABLES 6A-6F-continued

| Gene | Accession | Name | Sequence | Length | Seq ID. |
|---|---|---|---|---|---|
| IRS1 | NM_005544 | S1943/IRS1.f3 | CCACAGCTCACCTTCTGTCA | 20 | 265 |
| IRS1 | NM_005544 | S1944/IRS1.r3 | CCTCAGTGCCAGTGTCTTCC | 20 | 266 |
| IRS1 | NM_005544 | S5050/IRS1.p3 | TCCATCCCAGCTCCAGCCAG | 20 | 267 |
| ITGA3 | NM_002204 | S2347/ITGA3.f2 | CCATGATCCTCACTCTGCTG | 20 | 268 |
| ITGA3 | NM_002204 | S2348/ITGA3.r2 | GAAGCTTTGTAGCCGGTGAT | 20 | 269 |
| ITGA3 | NM_002204 | S4852/ITGA3.p2 | CACTCCAGACCTCGCTTAGCATGG | 24 | 270 |
| ITGB3 | NM_000212 | S3126/ITGB3.f1 | ACCGGGAGCCCTACATGAC | 19 | 271 |
| ITGB3 | NM_000212 | S3127/ITGB3.r1 | CCTTAAGCTCTTTCACTGACTCAATCT | 27 | 272 |
| ITGB3 | NM_000212 | S3243/ITGB3.p1 | AAATACCTGCAACCGTTACTGCCGTGAC | 28 | 273 |
| KRT17 | NM_000422 | S0172/KRT17.f2 | CGAGGATTGGTTCTTCAGCAA | 21 | 274 |
| KRT17 | NM_000422 | S0174/KRT17.r2 | ACTCTGCACCAGCTCACTGTTG | 22 | 275 |
| KRT17 | NM_000422 | S5013/KRT17.p2 | CACCTCGCGGTTCAGTTCCTCTGT | 24 | 276 |
| LAMC2 | NM_005562 | S2826/LAMC2.f2 | ACTCAAGCGGAAATTGAAGCA | 21 | 277 |
| LAMC2 | NM_005562 | S2827/LAMC2.r2 | ACTCCCTGAAGCCGAGACACT | 21 | 278 |
| LAMC2 | NM_005562 | S4969/LAMC2.p2 | AGGTCTTATCAGCACAGTCTCCGCCTCC | 28 | 278 |
| MTA1 | NM_004689 | S2369/MTA1.f1 | CCGCCCTCACCTGAAGAGA | 19 | 280 |
| MTA1 | NM_004689 | S2370/MTA1.r1 | GGAATAAGTTAGCCGCGCTTCT | 22 | 281 |
| MTA1 | NM_004689 | S4855/MTA1.p1 | CCCAGTGTCCGCCAAGGAGCG | 21 | 282 |
| NMYC | NM_005378 | S2884/NMYC.f2 | TGAGCGTCGCAGAAACCA | 18 | 283 |
| NMYC | NM_005378 | S2885/NMYC.r2 | TCCCTGAGCGTGAGAAAGCT | 20 | 284 |
| NMYC | NM_005378 | S4976/NMYC.p2 | CCAGCGCCGCAACGACCTTC | 20 | 285 |
| p14ARF | NM_000077 | S0199/p14ARF.f3 | GCGGAAGGTCCCTCAGACA | 19 | 286 |
| p14ARF | NM_000077 | S0201/p14ARF.r3 | TCTAAGTTTCCCGAGGTTTCTCA | 23 | 297 |
| p14ARF | NM_000077 | S5068/p14ARF.p3 | CCCCGATTGAAAGAACCAGAGAGGCT | 26 | 288 |
| p27 | NM_004064 | S0205/p27.f3 | CGGTGGACCACGAAGAGTTAA | 21 | 289 |
| p27 | NM_004064 | S0207/p27.r3 | GGCTCGCCTCTTCCATGTC | 19 | 290 |
| p27 | NM_004064 | S4750/p27.p3 | CCGGGACTTGGAGAAGCACTGCA | 23 | 291 |
| P53 | NM_000546 | S0208/P53.f2 | CTTTGAACCCTTGCTTGCAA | 20 | 292 |
| P53 | NM_000546 | S0210/P53.r2 | CCCGGGACAAAGCAAATG | 18 | 293 |
| P53 | NM_000546 | S5065/P53.p2 | AAGTCCTGGGTGCTTCTGACGCACA | 25 | 294 |
| PAI1 | NM_000602 | S0211/PAI1.f3 | CCGCAACGTGGTTTTCTCA | 19 | 295 |
| PAI1 | NM_000602 | S0213/PAI1.r3 | TGCTGGGTTTCTCCTCCTGTT | 21 | 296 |
| PAI1 | NM_000602 | S5066/PAI1.p3 | CTCGGTGTTGGCCATGCTCCAG | 22 | 297 |
| PDGFA | NM_002607 | S0214/PDGFA.f3 | TTGTTGGTGTGCCCTGGTG | 19 | 298 |
| PDGFA | NM_002607 | S0216/PDGFA.r3 | TGGGTTCTGTCCAAACACTGG | 21 | 299 |
| PDGFA | NM_002607 | S5067/PDGFA.p3 | TGGTGGCGGTCACTCCCTCTGC | 22 | 300 |
| PDGFB | NM_002608 | S0217/PDGFB.f3 | ACTGAAGGAGACCCTTGGAG | 20 | 301 |
| PDGFB | NM_002608 | S0219/PDGFB.r3 | TAAATAACCCTGCCCACACA | 20 | 302 |
| PDGFB | NM_002608 | S5014/PDGFB.p3 | TCTCCTGCCGATGCCCCTAGG | 21 | 303 |

TABLES 6A-6F-continued

| Gene | Accession | Name | Sequence | Length | Seq ID. |
|---|---|---|---|---|---|
| PGK1 | NM_000291 | S0232/PGK1.f1 | AGAGCCAGTTGCTGTAGAACTCAA | 24 | 304 |
| PGK1 | NM_000291 | S0234/PGK1.r1 | CTGGGCCTACACAGTCCTTCA | 21 | 305 |
| PGK1 | NM_000291 | S5022/PGK1.p1 | TCTCTGCTGGGCAAGGATGTTCTGTTC | 27 | 306 |
| PLAUR | NM_002659 | S1976/PLAUR.f3 | CCCATGGATGCTCCTCTGAA | 20 | 307 |
| PLAUR | NM_002659 | S1977/PLAUR.r3 | CCGGTGGCTACCAGACATTG | 20 | 308 |
| PLAUR | NM_002659 | S5054/PLAUR.p3 | CATTGACTGCCGAGGCCCCATG | 22 | 309 |
| PPARG | NM_005037 | S3090/PPARG.f3 | TGACTTTATGGAGCCCAAGTT | 21 | 310 |
| PPARG | NM_005037 | S3091/PPARG.r3 | GCCAAGTCGCTGTCATCTAA | 20 | 311 |
| PPARG | NM_005037 | S4824/PPARG.p3 | TTCCAGTGCATTGAACTTCACAGCA | 25 | 312 |
| PTPD1 | NM_007039 | S3069/PTPD1.f2 | CGCTTGCCTAACTCATACTTTCC | 23 | 313 |
| PTPD1 | NM_007039 | S3070/PTPD1.r2 | CCATTCAGACTGCGCCACTT | 20 | 314 |
| PTPD1 | NM_007039 | S4822/PTPD1.p2 | TCCACGCAGCGTGGCACTG | 19 | 315 |
| RANBP2 | NM_006267 | S3081/RANBP2.f3 | TCCTTCAGCTTTCACACTGG | 20 | 316 |
| RANBP2 | NM_006267 | S3082/RANBP2.r3 | AAATCCTGTTCCCACCTGAC | 20 | 317 |
| RANBP2 | NM_006267 | S4823/RANBP2.p3 | TCCAGAAGAGTCATGCAACTTCATTTCTG | 29 | 318 |
| RASSF1 | NM_007182 | S2393/RASSF1.f3 | AGTGGGAGACACCTGACCTT | 20 | 319 |
| RASSF1 | NM_007182 | S2394/RASSF1.r3 | TGATCTGGGCATTGTACTGC | 20 | 320 |
| RASSF1 | NM_007182 | S4909/RASSF1.p3 | TTGATCTTCTGCTCAATCTCAGCTTGAGA | 29 | 321 |
| RB1 | NM_000321 | S2700/RB1.f1 | CGAAGCCCTTACAAGTTTCC | 20 | 322 |
| RB1 | NM_000321 | S2701/RB1.r1 | GGACTCTTCAGGGGTGAAAT | 20 | 323 |
| RB1 | NM_000321 | S4765/RB1.p1 | CCCTTACGGATTCCTGGAGGGAAC | 24 | 324 |
| RIZ1 | NM_012231 | S1320/RIZ1.f2 | CCAGACGAGCGATTAGAAGC | 20 | 325 |
| RIZ1 | NM_012231 | S1321/RIZ1.r2 | TCCTCCTCTTCCTCCTCCTC | 20 | 326 |
| RIZ1 | NM_012231 | S4761/RIZ1.p2 | TGTGAGGTGAATGATTTGGGGA | 23 | 327 |
| RPLPO | NM_001002 | S0256/RPLPO.f2 | CCATTCTATCATCAACGGGTACAA | 24 | 328 |
| RPLPO | NM_001002 | S0258/RPLPO.r2 | TCAGCAAGTGGGAAGGTGTAATC | 23 | 329 |
| RPLPO | NM_001002 | S4744/RPLPO.p2 | TCTCCACAGACAAGGCCAGGACTCG | 25 | 330 |
| SPRY2 | NM_005842 | S2985/SPRY2.f2 | TGTGGCAAGTGCAAATGTAA | 20 | 331 |
| SPRY2 | NM_005842 | S2986/SPRY2.r2 | GTCGCAGATCCAGTCTGATG | 20 | 332 |
| SPRY2 | NM_005842 | S4811/SPRY2.p2 | CAGAGGCCTTGGGTAGGTGCACTC | 24 | 333 |
| Src | NM_004383 | S1820/Src.f2 | CCTGAACATGAAGGAGCTGA | 20 | 334 |
| Src | NM_004383 | S1821/Src.r2 | CATCACGTCTCCGAACTCC | 19 | 335 |
| Src | NM_004383 | S5034/Src.p2 | TCCCGATGGTCTGCAGCAGCT | 21 | 336 |
| STK15 | NM_003600 | S0794/STK15.f2 | CATCTTCCAGGAGGACCACT | 20 | 337 |
| STK15 | NM_003600 | S0795/STK15.r2 | TCCGACCTTCAATCATTTCA | 20 | 338 |
| STK15 | NM_003600 | S4745/STK15.p2 | CTCTGTGGCACCCTGGACTACCTG | 24 | 339 |
| SURV | NM_001168 | S0259/SURV.f2 | TGTTTTGATTCCCGGGCTTA | 20 | 340 |
| SURV | NM_001168 | S0261/SURV.r2 | CAAAGCTGTCAGCTCTAGCAAAG | 24 | 341 |
| SURV | NM_001168 | S4747/SURV.p2 | TGCCTTCTTCCTCCCTCACTTCTCACCT | 28 | 342 |

TABLES 6A-6F-continued

| Gene | Accession | Name | Sequence | Length | Seq ID. |
|---|---|---|---|---|---|
| TERC | U86046 | S2709/TERC.f2 | AAGAGGAACGGAGCGAGTC | 19 | 343 |
| TERC | U86046 | S2710/TERC.r2 | ATGTGTGAGCCGAGTCCTG | 19 | 344 |
| TERC | U86046 | S4958/TERC.p2 | CACGTCCCACAGCTCAGGGAATC | 23 | 345 |
| TFRC | NM_003234 | S1352/TFRC.f3 | GCCAACTGCTTTCATTTGTG | 20 | 346 |
| TFRC | NM_003234 | S1353/TFRC.r3 | ACTCAGGCCCATTTCCTTTA | 20 | 347 |
| TFRC | NM_003234 | S4748/TFRC.p3 | AGGGATCTGAACCAATACAGAGCAGACA | 28 | 348 |
| TGFBR2 | NM_003242 | S2422/TGFBR2.f3 | AACACCAATGGGTTCCATCT | 20 | 349 |
| TGFBR2 | NM_003242 | S2423/TGFBR2.r3 | CCTCTTCATCAGGCCAAACT | 20 | 350 |
| TGFBR2 | NM_003242 | S4913/TGFBR2.p3 | TTCTGGGCTCCTGATTGCTCAAGC | 24 | 351 |
| TIMP2 | NM_003255 | S1680/TIMP2.f1 | TCACCCTCTGTGACTTCATCGT | 22 | 352 |
| TIMP2 | NM_003255 | S1681/TIMP2.r1 | TGTGGTTCAGGCTCTTCTTCTG | 22 | 353 |
| TIMP2 | NM_003255 | S4916/TIMP2.p1 | CCCTGGGACACCCTGAGCACCA | 22 | 354 |
| TITF1 | NM_003317 | S2224/TITF1.f1 | CGACTCCGTTCTCAGTGTCTGA | 22 | 355 |
| TITF1 | NM_003317 | S2225/TITF1.r1 | CCCTCCATGCCCACTTTCT | 19 | 356 |
| TITF1 | NM_003317 | S4829/TITF1.p1 | ATCTTGAGTCCCCTGGAGGAAAGC | 24 | 357 |
| TP53BP1 | NM_005657 | S1747/TP53BP.f2 | TGCTGTTGCTGAGTCTGTTG | 20 | 358 |
| TP53BP1 | NM_005657 | S1748/TP53BP.r2 | CTTGCCTGGCTTCACAGATA | 20 | 359 |
| TP53BP1 | NM_005657 | S4924/TP53BP.p2 | CCAGTCCCCAGAAGACCATGTCTG | 24 | 360 |
| upa | NM_002658 | S0283/upa.f3 | GTGGATGTGCCCTGAAGGA | 19 | 361 |
| upa | NM_002658 | S0285/upa.r3 | CTGCGGATCCAGGGTAAGAA | 20 | 362 |
| upa | NM_002658 | S4769/upa.p3 | AAGCCAGGCGTCTACACGAGAGTCTCAC | 28 | 363 |
| VEGFC | NM_005429 | S2251/VEGFC.f1 | CCTCAGCAAGACGTTATTTGAAATT | 25 | 364 |
| VEGFC | NM_005429 | S2252/VEGFC.r1 | AAGTGTGATTGGCAAAACTGATTG | 24 | 365 |
| VEGFC | NM_005429 | S4758/VEGFC.p1 | CCTCTCTCTCAAGGCCCCAAACCAGT | 26 | 366 |
| XIAP | NM_001167 | S0289/XIAP.f1 | GCAGTTGGAAGACACAGGAAAGT | 23 | 367 |
| XIAP | NM_001167 | S0291/XIAP.r1 | TGCGTGGCACTATTTTCAAGA | 21 | 368 |
| XIAP | NM_001167 | S4752/XIAP.p1 | TCCCCAAATTGCAGATTTATCAACGGC | 27 | 369 |
| YB-1 | NM_004559 | S1194/YB-1.f2 | AGACTGTGGAGTTTGATGTTGTTGA | 25 | 370 |
| YB-1 | NM_004559 | S1195/YB-1.r2 | GGAACACCACCAGGACCTGTAA | 22 | 371 |
| YB-1 | NM_004559 | S4843/YB-1.p2 | TTGCTGCCTCCGCACCCTTTCT | 23 | 372 |

What is claimed is:

1. A method for predicting the likelihood that a human colon cancer patient will exhibit a clinically beneficial patient response to treatment with cetuximab, the method comprising:
   a) assaying a normalized level of a predictive RNA transcript in a sample comprising ErbB1-expressing colon cancer cells obtained from said patient, wherein the predictive RNA transcript is the transcript of laminin gamma 2 (LAMC2);
   b) analyzing the normalized level of the LAMC2 transcript; and
   c) predicting the likelihood of response of the patient to treatment with cetuximab by comparing the normalized level of the LAMC2 transcript to gene expression data obtained from reference samples derived from patients with colon cancer, wherein an increased normalized level of LAMC2 RNA transcript correlates with a decreased likelihood of response to treatment with cetuximab.

2. The method of claim 1, wherein said sample is a tissue sample.

3. The method of claim 2, wherein the tissue sample is fixed, paraffin-embedded, or fresh, or frozen.

4. The method of claim 2, wherein the tissue sample is derived from fine needle, core, or other types of biopsy.

5. The method of claim 1, further comprising the step of preparing a report comprising a statement whether the patient is likely to respond to treatment with cetuximab.

6. The method of claim 1, wherein the normalized level of the LAMC2 RNA transcript is determined using an array comprising polynucleotides hybridizing to a LAMC2 gene immobilized on a solid surface.

7. The method of claim 6, wherein said polynucleotides are cDNAs.

8. The method of claim 7, wherein said cDNAs are about 500 to about 5000 bases.

9. The method of claim 6, wherein said polynucleotides are oligonucleotides.

10. The method of claim 9, wherein said oligonucleotides are about 20 to 80 bases long.

11. The method of claim 6, wherein the array comprises about 330,000 oligonucleotides.

12. The method of claim 6 wherein said solid surface is glass.

13. The method of claim 2, wherein RNA is isolated from colon cancer cells present in a fixed, paraffin-embedded tissue by a procedure comprising:
   (a) incubating one or more sections of said fixed, paraffin-embedded tissue at a temperature of about 56° C. to 70° C. in a lysis buffer, in the presence of a protease, without prior dewaxing, to form a lysis solution;
   (b) cooling the lysis solution to a temperature where the paraffin solidifies, thereby generating a cooled lysis solution; and
   (c) isolating the RNA from said cooled lysis solution.

14. The method of claim 1, further comprising the use of a kit comprising one or more of (1) extraction buffer/reagents for extracting mRNA from a sample and protocol; (2) reverse transcription buffer/reagents and protocol; and (3) quantitative polymerase chain reaction (qPCR) buffer/reagents and protocol suitable for performing the method of claim 1.

15. The method of claim 6, wherein said polynucleotides comprise modified and unmodified polynucleotides.

* * * * *